US011364310B2

(12) United States Patent
Kamrud

(10) Patent No.: US 11,364,310 B2
(45) Date of Patent: Jun. 21, 2022

(54) RECOMBINANT VIRUS REPLICON SYSTEMS AND USES THEREOF

(71) Applicant: Janssen Pharmaceuticals, Inc., Titusville, NJ (US)

(72) Inventor: Kurt Iver Kamrud, San Diego, CA (US)

(73) Assignee: JANSSEN PHARMACEUTICALS, INC., Titusville, NJ (US)

( * ) Notice: Subject to any disclaimer, the term of this patent is extended or adjusted under 35 U.S.C. 154(b) by 506 days.

(21) Appl. No.: 15/723,658

(22) Filed: Oct. 3, 2017

(65) Prior Publication Data

US 2018/0104359 A1    Apr. 19, 2018

Related U.S. Application Data

(60) Provisional application No. 62/409,228, filed on Oct. 17, 2016.

(51) Int. Cl.
| | | |
|---|---|---|
| *C12N 15/86* | (2006.01) | |
| *C12N 7/01* | (2006.01) | |
| *C12N 5/10* | (2006.01) | |
| *A61K 48/00* | (2006.01) | |
| *C12N 15/67* | (2006.01) | |
| *A61K 39/00* | (2006.01) | |

(52) U.S. Cl.
CPC .......... *A61K 48/0066* (2013.01); *C12N 15/67* (2013.01); *C12N 15/86* (2013.01); *A61K 2039/53* (2013.01); *C12N 2770/36143* (2013.01)

(58) Field of Classification Search
None
See application file for complete search history.

(56) References Cited

U.S. PATENT DOCUMENTS

| | | | |
|---|---|---|---|
| 4,727,138 A | 2/1988 | Goeddel et al. | |
| 4,738,927 A | 4/1988 | Taniguchi et al. | |
| 4,762,791 A | 4/1988 | Goeddel et al. | |
| 4,810,643 A | 3/1989 | Souza | |
| 4,892,743 A | 1/1990 | Leibowitz et al. | |
| 4,966,843 A | 10/1990 | McCormick et al. | |
| 4,999,291 A | 3/1991 | Souza | |
| 5,017,691 A | 5/1991 | Lee et al. | |
| 5,116,742 A | 5/1992 | Cech et al. | |
| 5,225,337 A | 7/1993 | Robertson et al. | |
| 5,246,921 A | 9/1993 | Reddy et al. | |
| 5,780,036 A | 7/1998 | Chisari | |
| 5,958,060 A | 9/1999 | Premerlani | |
| 6,041,252 A | 3/2000 | Walker | |
| 6,110,161 A | 8/2000 | Mathiesen | |
| 6,117,660 A | 9/2000 | Walters | |
| 6,224,879 B1 | 5/2001 | Sjoberg et al. | |
| 6,261,281 B1 | 7/2001 | Mathiesen | |
| 6,273,525 B1 | 8/2001 | Erban | |
| 6,278,895 B1 | 8/2001 | Bernard | |
| 6,319,901 B1 | 11/2001 | Bernard | |
| 6,697,669 B2 | 2/2004 | Dev | |
| 6,873,549 B2 | 3/2005 | Khalid | |
| 6,873,849 B2 | 3/2005 | De La Red | |
| 6,912,417 B1 | 6/2005 | Bernard | |
| 6,939,862 B2 | 9/2005 | Bureau | |
| 6,958,060 B2 | 10/2005 | Mathiesen | |
| 6,982,087 B2 | 1/2006 | Johnston et al. | |
| 7,328,064 B2 | 2/2008 | Mathiesen | |
| 7,419,674 B2 | 9/2008 | Chulay et al. | |
| 7,664,545 B2 | 2/2010 | Westersten | |
| 7,850,977 B2 | 12/2010 | Kamrud | |
| 8,080,255 B2 | 12/2011 | Smith | |
| 8,187,249 B2 | 5/2012 | Bernard | |
| 8,209,006 B2 | 6/2012 | Smith | |
| 8,216,589 B2 | 7/2012 | Yum | |
| 8,859,198 B2 | 10/2014 | Bartholomeusz | |
| 8,961,995 B2 | 2/2015 | Frolov | |
| 9,364,664 B2 | 6/2016 | Masterson | |
| 9,452,285 B2 | 9/2016 | Draghia-Akli | |
| 9,801,897 B2 | 10/2017 | Geall et al. | |
| 9,802,035 B2 | 10/2017 | Masterson | |
| 10,538,786 B2 | 1/2020 | Kamrud | |
| 2004/0213805 A1 | 10/2004 | Verheije | |
| 2004/0235133 A1 | 11/2004 | Frolov | |

(Continued)

FOREIGN PATENT DOCUMENTS

| | | |
|---|---|---|
| JP | H10500017 | 1/1998 |
| WO | WO 1985/02862 | 7/1985 |

(Continued)

OTHER PUBLICATIONS

Petrakova et al., Noncytopathic Replication of Venezuelan Equine Encephalitis Virus and Eastern Equine Encephalitis Virus Replicons in Mammalian Cells, Journal of Virology, Jun. 2005, p. 7597-7608.*
Agapov et al., Noncytopathic Sindbis Virus RNA Vectors for Heterologous Gene Expression, Proc. Natl. Acad. Sci., 1998, pp. 12989-12994, vol. 95.
Altmann et al., Cotransfection of ICAM-1 and HLA-DR Reconstitutes Human Antigen-Presenting Cell Function in Mouse L Cells, Nature, 1989, pp. 512-514, vol. 338.
Altschul SF et al., "Basic Local Alignment Search Tool"; J. Mol. Biol. 215:403-410, 1990.
Atkins, G, et al. Theraputic and Prophylatic Applications of Alphavurus Vectors, Expert Reviews in Molecular Medi, Cambridge University Press, vol. 10, No. 1, pp. 1-18, (2008).
Attwood, T. The Abel of Bionofrmatics, vol. 290, No. 5491, pp. 471-473, (2000).

(Continued)

*Primary Examiner* — Maria Marvich
(74) *Attorney, Agent, or Firm* — Ice Miller LLP

(57) ABSTRACT

The present disclosure generally relates to viral-based expression systems suitable for the production of molecules of interest. The disclosure relates to nucleic acid constructs, such as expression vectors, containing a modified replicon RNA which includes a modified 5'-unstranslated region (5'-UTR) and, optionally, at least some of its original viral sequence encoding structural proteins having been deleted. Also disclosed are methods for producing polypeptides of interest.

18 Claims, 8 Drawing Sheets

Specification includes a Sequence Listing.

(56) References Cited

U.S. PATENT DOCUMENTS

| | | | |
|---|---|---|---|
| 2005/0070700 A1 | 3/2005 | Giese | |
| 2005/0277605 A1 | 12/2005 | Wu | |
| 2009/0018031 A1 | 1/2009 | Trinklein et al. | |
| 2009/0075384 A1* | 3/2009 | Kamrud | A61K 39/285 435/465 |
| 2011/0110974 A1 | 5/2011 | Depla | |
| 2012/0078161 A1 | 3/2012 | Masterson | |
| 2012/0121650 A1* | 5/2012 | Johnston | A61K 39/21 424/278.1 |
| 2014/0079734 A1 | 3/2014 | Ilya et al. | |
| 2014/0222105 A1 | 8/2014 | Broderick | |
| 2015/0328404 A1 | 11/2015 | Murakami | |
| 2016/0074500 A1 | 3/2016 | Pushko | |
| 2016/0166678 A1 | 6/2016 | Kallen et al. | |
| 2016/0362472 A1 | 12/2016 | Bitter | |
| 2017/0314043 A1 | 11/2017 | Kamrud et al. | |
| 2018/0104359 A1 | 4/2018 | Kamrud | |
| 2018/0171340 A1 | 6/2018 | Kamrud et al. | |

FOREIGN PATENT DOCUMENTS

| | | |
|---|---|---|
| WO | WO 1985/04188 | 9/1985 |
| WO | WO 1990/06370 | 6/1990 |
| WO | 9503777 A1 | 2/1995 |
| WO | WO 1995/31565 A1 | 11/1995 |
| WO | WO 1996/37616 A1 | 11/1996 |
| WO | 200224224 A2 | 3/2002 |
| WO | 2002042480 A2 | 5/2002 |
| WO | WO 2004/055161 A2 | 7/2004 |
| WO | 2005087311 A1 | 9/2005 |
| WO | 2008093976 A1 | 8/2008 |
| WO | 2011015656 A2 | 2/2011 |
| WO | WO 2012/087983 A1 | 6/2012 |
| WO | 2012109668 A1 | 8/2012 |
| WO | 2013007772 A1 | 1/2013 |
| WO | WO 2014/170493 A2 | 10/2014 |
| WO | 2016020538 A1 | 2/2016 |
| WO | 2016054003 A1 | 4/2016 |
| WO | WO 2016/184822 A1 | 9/2016 |
| WO | WO 2017/024000 A1 | 2/2017 |
| WO | 2017172838 A1 | 10/2017 |
| WO | 2017176319 A1 | 10/2017 |
| WO | WO 2017/180770 A1 | 10/2017 |
| WO | WO 2018/075235 A1 | 4/2018 |
| WO | WO 2018/106615 A1 | 6/2018 |
| WO | 2018225731 A1 | 12/2018 |
| WO | 2019099624 A1 | 5/2019 |
| WO | 2019123252 A1 | 6/2019 |

OTHER PUBLICATIONS

Baker et al, Proten Structure Prediction and Structual Genomics, Science, vol. 294, pp. 93-93, (2011).

Barbieri et al., Purification and partial characterization of another form of the antiviral protein from the seeds of *Phytolacca americana* L. (pokeweed), Biochem. J., 1982, pp. 55-59, vol. 203.

Barrette-Ng et al., Structure of Arterivirus nsp-4, J. Biol. Chem., 2002, pp. 39960-39966, vol. 277, Issue 42.

Beerens & Snijder, An RNA Pseudoknot in the 3' End of the Arterivirus Genome Has a Critical Role in Regulating Viral RNA Synthesis, J. Virol., 2007, pp. 9426-9436, vol. 81, Issue 17.

Berglund, P. et al., Enhancing Immune Response Using Suicidal DNA Vaccines,, Nature Biotechnology, vol. 16, pp. 562-565, (1998).

Besnard et al., Selection against expression of the *Escherichia coli* gene gpt in hprt+ mouse teratocarcinoma and hybrid cells, Mol. Cell. Biol., 1987, pp. 4139-4141, vol. 7.

Brakenhof et al., Molecular cloning and expression of hybridoma growth factor in *Escherichia coli*, J. Immunol., Dec. 15, 1987, pp. 4116-4121, vol. 139, Issue 12.

Bzik et al., Molecular cloning and sequence analysis of the Plasmodium falciparum dihydrofolate reductase-thymidylate synthase gene, Proc. Natl. Acad. Sci. USA, Dec. 1987, pp. 8360-8364, vol. 84.

Calderwood et al., Nucleotide sequence of the Shiga-like toxin genes of *Escherichia coli*, Proc. Natl. Acad. Sci. USA, Jul. 1987, pp. 4364-4368, vol. 84.

Carroll and Collier, Active Site of Pseudomonas aeruginosa Exotoxin A, J. Biol. Chem., 1987, pp. 8707-8711, vol. 262.

Castillo-Olivares et al., Generation of a Candidate Live Marker Vaccine for Equine Arteritis Virus by Deletion of the Major Virus Neutralization Domain, J. Virol., 2003, pp. 8470-8480, vol. 77, Issue 15.

Chen et al., The complete primary structure of abrin-a B chain. FEBS Letters, 1992, pp. 115-118, vol. 309.

Cheng, W. et al. Enhancement of Sindbis Virus Self-Replicating RNA Vaccine Potency by Linkage of Mycobacterium tuberculosis Heat Shock Protein 70 Gene to an Antigen Gene, Journal of Immunology, vol. 166, pp. 6218-6226, (2001).

Chin et al., Tissue-specific Expression of Hepatic Functions Genetic Aspects, Ann. N.Y. Acad. Sci., Oct. 1986, pp. 120-130, vol. 478.

Collins et al., Primary Amino Acid Sequence of a-Trichosanthin and Molecular Models for Abrin A-chain and α-Trichosanthin, J. Biol. Chem., 1990, pp. 8665-8669, vol. 265.

Coussens et al., Tyrosine kinase receptor with extensive homology to EGF receptor shares chromosomal location with neu oncogene, Science, 1985, pp. 1132-1139, vol. 230.

Davis, N. et al., In Vitro Synthesis of Infectious Venezuelan Equine Encephalitis Virus RNA from cDNA Clone: Analysis of a Viable Deletion Mutant' Virology, vol. 171, pp. 189-204, (1989).

De Vries et al., Genetic Manipulation of Equine Arteritis Virus Using Full-Length cDNA Clones: Separation of Overlapping Genes and Expression of a Foreign Epitope. Virology, 2000, pp. 84-97, vol. 270.

De Vries et al., Recombinant Equine Arteritis Virus Expression Vector, Virology, Jun. 5, 2001, pp. 259-276, vol. 284, Issue 2.

De Wilde et al., Cyclophilin Inhibitors Block Arterivirus Replication by Interfering with Viral RNA Synthesis, J. Virol., 2013, pp. 1454-1464, vol. 87, Issue 3.

Den Boon et al., Equine Arteritis Virus Subgenomic RNA Transcription: UV Inactivation and Translation Inhibition Studies, Virology, 1995, pp. 364-372, vol. 213.

Deng et al., Structural Basis for the Regulatory Function of a Complex Zinc-binding Domain in a Replicative Arterivirus Helicase Resembling a Nonsense-Mediated mRNA Decay Helicase, Nucl. Acids Res., 2013, pp. 3464-3477, vol. 42, Issue 5.

Ding et al., In Vivo Genome-Wide Profiling of RNA Secondary Structure Reveals Novel Regulatory Features, Nature, 2014, pp. 696-700 (and Methods), vol. 505.

Dowdy et al., Efficient Generation of Human iPSCs by a Synthetic Self-Replicative RNA, Cell Stem Cell, 2013, pp. 246-254, vol. 13.

Dubensky, T. et al. Sindbis Virus DNA-Based Expression Vectors: Utility for In Vitro and In Vivo Gene Transfer, Journal of Virology, vol. 70, No. 1, pp. 508-519, (1996).

Evensen et al., Direct Molecular Cloning and Expression of Two Distinct Abrin A-chains, J. Biol. Chem., Apr. 15, 1991, pp. 6848-6852, vol. 266, Issue 11.

Fainstein et al., Nucleotide sequence analysis of human abl and bcr-abl cDNAs, Oncogene, Dec. 1, 1989, pp. 1477-1481, vol. 4. Issue 12.

Faktor et al., The identification of hepatitis B virus X gene responsive elements reveals functional similarity of X and HTLV-I tax, Oncogene, Jun. 1, 1990, pp. 867-872, vol. 5, Issue 6.

Familletti et al., A convenient and rapid cytopathic effect inhibition assay for interferon, Methods in Enz., 1981, pp. 387-394, vol. 78.

Fang et al., Efficient -2 Frameshifting by Mammalian Ribosomes to Synthesize an Additional Arterivirus Protein, PNAS, 2012, pp. E2920-E2928.

Field et al., Isolation and Characterization of Acyclovir-Resistant Mutants of Herpes Simplex Virus, J. Genl. Virol., 1980, pp. 115-124, vol. 49.

Finter et al., The Use of Interferon-α in Virus Infections, Drugs, 1991, pp. 749-765, vol. 42.

Firth et al., Discovery of a Small Arterivirus Gene that Overlaps the GP5 Coding Sequence and is Important for Virus Production, J. Genl. Virol., 2011, pp. 1097-1106, vol. 92.

(56) References Cited

OTHER PUBLICATIONS

Frolov, I. et al. Cis-acting RNA elements at the 5' end of Sindbis virus genome RNA regulate minus-and plus-strand RNA synthesis, RNO, vol. 7, pp. 1638-1651, (2001).
Frolov, I et al., Translation of Sindbis Virus mRNA: Effects of Sequences Downstream of the Initiating Codon Journal of Virology, Vo. 70, No. 2 , pp. 1182-1190 (1996).
Frolov, I et al.Translation of Sindbis Virus mRNA: Effects of Sequences Downstream of the Initiating Codon, Journal of Virology, vol. 68, No. 12, pp. 8111-8117, (1994).
Gansbacher et al., Retroviral Vector-mediated γ-Interferon Gene Transfer into Tumor Cells Generates Potent and Long Lasting Antitumor Immunity, Cancer Res., Dec. 15, 1999, pp. 7820-7825, vol. 50.
Gansbacher et al., Interleukin 2 Gene Transfer into Tumor Cells Abrogates Tumorigenicity and Includes Protective Immunity, J. Ex. Med., The Rockefeller University Press, Oct. 1990, pp. 1217-1224, vol. 172.
Gibson et al., Enzymatic Assembly of DNA Molecules up to Several Hundred Kilbases, Nature Methods 6:343-45, 2009.
Giulietta et al. 2013. Engineered alphavirus replicon vaccines based on known attenuated viral mutants show limited effects on immunogenicity. *Virology*, 447(1):254-264.
Glaser Al et al., An infectious cDNA clone of equine arteritis virus: a tool for future fundamental studies and vaccine development. Proceedings of the 8th International Conference on Equine Infectious Diseases, Dubai 1998; 1999, pp. 166-176.
Golumbek et al., Treatment of established renal cancer by tumor cells engineered to secrete interleukin-4, Science, Nov. 1, 1991, pp. 713-716, vol. 254.
Gorchakov, R. et al., Selection of Functional 5 cis-Acting Elements Promoting Efficient Sindbis Virus Genome Replication, Journal of Virology, vol. 78, No. 1, pp. 61-75, (2004).
Grabstein et al., Cloning of a T cell growth factor that interacts with the beta chain of the interleukin-2 receptor. Science, 1994, pp. 965-968, vol. 264.
Hardy, R. et al. Requirements at the 3 End of the Sindbis Virus Genome for Efficient Synthesis of Minus-Strand RNA, Journal of Virology, pp. 4630-4639, (2005).
Hooper et al., Molecular Smallpox Vaccine Delivered by Alphavirus Replicons Elicits Protective Immunity in Mice and Non-Human Primates, Vaccine, 2009, pp. 494-511, vol. 28, Issue 2.
Horikawa et al., Molecular cloning and nucleotide sequence of cDNA encoding the human liver S-adenosylmethionine synthetase, Biochem. Intl., Sep. 1, 1991, pp. 81-90, vol. 25, Issue 1.
Hyde, J. et al., The 5' and 3' ends of alphavirus RNAs—non-coding is not non-functional, Virus Res., vol. 206, pp. 99-107, (2015).
Huang, Q. et a l. Development of a Vaccine Vector Based on a Subgeonomic Replication of Porcine Reproductive and Respitory Syndrome Virus, Journal of Virological Methods, vol. 160, pp. 22-28, (2009).
Irvin JD, Purification and partial characterization of the antiviral protein from Phytolacca americana which inhibits eukaryotic protein synthesis, Arch. Biochem & Biophys, Aug. 1975, pp. 522-528, vol. 169, Issue 2.
Irvin JD, Pokeweed antiviral protein, Pharmac. Ther., 1983, pp. 371-387, vol. 21, Issue 3.
Irvin JD et al., Purification and properties of a second antiviral protein from Phytolacca americana which inactivates eukaryotic ribosomes, Arch. Biochem. & Biophys., Apr. 1, 1980, pp. 418-425, vol. 200, Issue 2.
Jackson et al., Nucleotide sequence analysis of the structural genes for Shiga-like toxin I encoded by bacteriophage 933J from *Escherichia coli*. Microb. Path., Feb. 1987, pp. 147-153, vol. 2, Issue 2.
Jayaraman et al., Enhancement of in vivo cell-mediated immune responses by three distinct cytokines, J. Immunol., 1990, pp. 942-951, vol. 144.
Kamrud et al., Alphavirus Replicon Approach to Promoterless Analysis of IRES Elements, Virology, 2007, pp. 376-387, vol. 360.

Karlin & Altschul, Applications and statistics for multiple high-scoring segments in molecular sequences Proc. Nat'l. Acad. Sci. USA 90:5873-87, 1993).
Karupiah et al., Elevated natural killer cell responses in mice infected with recombinant vaccinia virus encoding murine IL-2, J. Immunol., Jan. 1, 1990, pp. 290-298, vol. 144, Issue 1.
Kasteren PB et al., 2013. Deubiquitinase function of arterivirus papain-like protease 2 suppresses the innate immune response in infected host cells. Proc. Natl. Acad. Sci. USA, Feb. 2013, E838-E847.
Kelley, B. et al. Potential of Alphavirus Vecotrs in the Treament of Advanced Solid Tumors, Recent Patents on Anti-Drug Discovery, vol. 2, No. 2, pp. 159-166, (2007).
Kerr et al., Anti-penicillin-V-amidase conjugates kill antigen-positive tumor cells when combined with doxorubicin phenoxyacetamide, Cancer. Immunol. Immunother.,1990, pp. 202-206, vol. 31, Issue 4.
Kim et al. 2014. Enhancement of protein expression by alphavirus replicons by designing self-replicating subgenomic RNAs. *Proceedings National Academy of Sciences*, 111 (29):10708-10713.
Klimstra et al.. Adaptation of Sindbis Virus to BHK Cells Selects for Use of Heparan Sulfate as an Attachment Receptor. J. Virol. 72: pp. 7357, 1988.
Kinney, R. et al., Attenuation of Venezuelan Equine Encephalitis Virus Strain TC-83 Is Encoded by the 5'-Noncoding Region and the E2 Envelope Glycoprotein, Journal of Virology, vol. 67, No. 3, pp. 1269-1277, (1993).
Knoops et al., Ultrastructural Characterization of Arterivirus Replication Structures: Reshaping the Endoplasmic Reticulum to Accommodate Viral RNA Synthesis, J. Virol., 2011, pp. 2474-2487, vol. 86, Issue 5.
Kofler R et al., Mimicking live flavivirus immunization with a noninfectious RNA vaccine, PNAS, vol. 101, No. 7, pp. 1951-1956, (2004).
Kulasegaran-Shylini et al., Structural and Functional Elements of Promoter Encoded by the 5' Untranslated Region of the Venezuelan Equine Encephalitis Virus Genome J. Virol. 83:17 p. 8327-8339, 2009.
Kulasegaran-Shylini et al., The 5'UTR-specific mutation in VEEV TC-83 genome has a strong effect on RNA replication and subgenomic RNA synthesis, but not on translation of the encoded proteins. Virology. 2009, 387(1):211-221.
Lamb et al.., Nucleotide sequence of cloned cDNA coding for preproricin, Eur. J. Biochem.,1985, pp. 265-270, vol. 148.
Lee et al., Multiagent Vaccines Vectored by Venezuelan Equine Encephalitis Virus Replicon Elicits Immune Responses to Marburg Virus and Protection against Anthrax and Botulinum Neurotoxin in Mice, Vaccine, 2006, pp. 6886-6892, vol. 24.
Lehmann et al., Arterivirus nsp12 Versus the Coronavirus nsp16 2'-0-Methyltransferase: Comparison of the C-terminal Cleavage Products of Two Nidovirus pp1ab Polyproteins, J. Genl. Virol., 2015, pp. 2643-2655, vol. 96.
Lehmann et al., Arterivirus RNA-Dependent RNA Polymerase: Vital Enzymatic Activity remains Elusive, Virology, 2016, pp. 68-74, vol. 487.
Linsley et al., Binding of the B Cell activation antigen B7 to CD28 costimulates T cell proliferation and Interleukin 2 mRNA accumulation, J. Exp. Med., Mar. 1991, pp. 721-730, vol. 173.
Linsley et al., CTLA-4 Is a second receptor for the B Cell activation antigen B7, J. Exp. Med., Sep. 1991, pp. 561-570, vol. 174.
Luo, R., et al., Antiviral activity of type I and type III interferons against porcine reproductive and respiratory syndrome virus (PRRSV), Antiviral Resarch, vol. 91, pp. 99-101 (2011).
Maher and Dolinick, Specific hybridization arrest of dihydrofolate reductase mRNA in vitro using anti-sense RNA or anti-sense oligonucleotides, Arch. Biochem & Biophys., Feb. 15, 1987, pp. 214-220, vol. 253, Issue 1.
Maio, et al., Modulation by cytokines of HLA antigens, intercellular adhesion molecule 1 and high molecular weight melanoma associated antigen expression and of immune lysis of clones derived from the melanoma cell line MeM 50-10. Can. Immunol. Immunother., Jan. 1989, pp. 34-42, vol. 30, Issue 1.

(56) References Cited

OTHER PUBLICATIONS

Manolaridis, et al., Structure and Genetic Analysis of the Arterivirus Nonstructural Protein 7α, J. Virol., 2011, pp. 7449-7453, vol. 85, Issue 14.
McKnight et al., Deduced consensus sequence of Sindbis virus strain AR339: mutations contained in laboratory strains which affect cell culture and in vivo phenotypes. Virol. 70:1981, 1996.
McLoughlin, M. et al. Alphavirus infections in salmonids—a review, Journal of Fish Diseases, vol. 30, pp. 511-531, (2007).
Mekalanos et al., Cholera toxin genes: nucleotide sequence, deletion analysis and vaccine development, Nature, 1983, pp. 551-557, vol. 306.
Mogler, M. et al., RNA-based viral vectors, Expert Rev. Vaccines, pp. 1-30, (2014.
Molenkamp R et al., The arterivirus replicase is the only viral protein required for genome replication and subgenomic mRNA transcription, J. Genl. Virol., 2000, pp. 2491-2496, vol. 81.
Molenkamp et al., Isolation and Characterization of an Arterivirus Defective Interfering RNA Genome, J. Virol., 2000, pp. 3156-3165, vol. 74, Issue 7.
Molenkamp et al., Characterization of an Arterivirus Defective Interfering RNA, 2001, pp. 519-525. In The Nidoviruses (Coronaviruses and Arteriviruses), Ehud Lavi et al. (ed.), Kluwer Academic/Plenum Publishers.
Mullen, Transfer of the bacterial gene for cytosine deaminase to mammalian cells confers lethal sensitivity to 5-fluorocytosine: A negative selection system, Proc. Natl. Acad. Sci. USA, Jan. 1992, pp. 33-37, vol. 89.
Muraggi, G et al. Engineered Alphavirus Replicon Vaccines Based on Known Attenuated Viral Mutants Show Limited Effects on Immunogenicity, Virology, vol. 44, pp. 254-264, 2013.
Nagata, et al., Synthesis in *E. coli* of a polypeptide with human leukocyte interferon activity, Nature, 1980, pp. 316-320, vol. 284.
Nedialkova, et al., Biochemical Characterization of Arterivirus Nonstructural Protein 11 Reveals the Nidovirus-Wide Conservation of a Replicative Endoribonuclease, J. Virol., 2009, pp. 5671-5682, vol. 83, Issue 11.
Nedialkova et al., Arterivirus Nsp1 Modulates the Accumulation of Minus-Strand Templates to Control the Relative Abundance of Viral mRNAs, PLoS Pathogens, 2010, e1000772, pp. 1-15, vol. 6, Issue 2.
Needleman, S. et al., A general method applicable to the search for similarities in the amino acid sequence of two proteins J. Mol. Biol. 48:443-53, 1970.
Nolz, J et al. Strategies and Implications for Prime-Boost Vaccination to Generate Memory CD8 T Cells, Advances in Experimental Medicine and Biology, pp. 69-83, (2011).
Pasternak, Genetic Manipulation of Arterivirus Alternative mRNA Leader-Body Junction Sites Reveals Tight Regulation of Structural Protein Expression, J. Virol., Dec. 2000, pp. 11642-11653, vol. 74, Issue 24.
Pasternak, Sequence requirements for RNA strand transfer during nidovirus discontinuous subgenomic RNA synthesis, EMBO J., 2001, pp. 7220-7228, vol. 20, Issue 24.
Pasternak, The stability of the duplex between sense and antisense transcription-regulating sequences is a crucial factor in arterivirus subgenomic mRNA synthesis, J. Virol., 2003, pp. 1175-1183, vol. 77, Issue 2.
Pasternak, Regulation of Relative Abundance of Arterivirus Subgenomic mRNAs, J. Virol., Aug. 2004, pp. 8102-8113, vol. 78, Issue 15.
Pearson, W et al., Improved tools for biological sequence comparison, Proc. Natl. Acad. Sci Us, vol. 85, pp. 2444-2448, (1988).
Pedersen et al., Open Reading Frame 1a-Encoded Subunits of the Arterivirus Replicase induce Endoplasmic Reticulum-Derived Double-Membrane Vesicles which carry the Viral Replication Complex, J. Virol., 1999, pp. 2016-2026, vol. 73, Issue 3.
Perri et al., Replicon Vectors Derived from Sindbis Virus and Semliki Forest Virus that Establish Persistent Replication in Host Cells, J. Virol., 2000, pp. 9802-9807, vol. 74, Issue 20.
Pijlman, G. et al., Kunjin virus replicons: an RNA-based, noncytopathic viral vector system for protein production, vaccine and gene therapy applications, Expert Opin. Biol. Ther, vol. 6, No. 2, pp. 135-145, (2006).
Posthuma et al., Site-Directed Mutagenesis of the Nidovirus Replicative Endoribonuclease NendoU Exerts Pleiotropic Effects on the Arterivirus Life Cycle, J. Virol., 2006, pp. 1653-1661, vol. 80, Issue 4.
Posthuma et al., Formation of the Arterivirus Replication/Transcription Complex: a Key Role for Nonstructural Protein 3 in the Remodeling of Intracellular Membranes, J. Virol., 2008, pp. 4480-4491, vol. 82, Issue 9.
Pushko et al., Individual and Bivalent Vaccines Based on Alphavirus Replicons Protect Guinea Pigs against Infection with Lassa and Ebola Viruses, J. Virol., 2001, pp. 11677-11685, vol. 75, Issue 23.
Pushko et al., Replicon-Helper Systems from Attenuated Venezuelan Equine Encephalitis Virus: Expression of Heterologous Genes In Vitro and Immunization against Heterologous Pathogens In Vivo, Virology, Dec. 22, 1997, pp. 389-401, vol. 239, Issue 2.
Radford et al., Cell-Type Specificity of Interferon-γ-Mediated HLA Class I Gene Transcription in Human Hematopoietic Tumor Cells. American Society of Hepatology, 1991, pp. 2008-2015,.
Rice, C. et al., Production of Infectious RNA Transcripts from Sindbis Virus cDNA Clones: Mapping of Lethal Mutations, Rescue of a Temperature-Sensitive Marker, and In Vitro Mutagenesis To Generate Defined Mutants, Journal of Virology, vol. 61, No. 12, pp. 3809-3819, (1987).
Rogne et al., The isolation and characterisation of a cDNA clone for human lecithin:cholesterol acyl transferase and its use to analyze the genes in patients with LCAT deficiency and fish eye disease, Biochem, Biophys. Res. Commun., 1987, pp. 161-169, vol. 148, Issue 1.
Sanchez and Holmgren, Recombinant system for overexpression of cholera toxin B subunit in Vibrio cholerae as a basis for vaccine development, Proc. Natl. Acad. Sci. USA, Jan. 1989, pp. 481-485, vol. 86, Issue 2.
Seif et al., Stable Antiviral Expression in BALB/c 3T3 Cells Carrying a Beta Interferon Sequence behind a Major Histocompatibility Complex Promoter Fragment, J. Virol., Oct. 1991, pp. 664-671, vol. 65, Issue 2.
Seybert et al., Biochemical Characterization of the Equine Arteritis Virus Helicase Suggests a Close Functional Relationship Between Arterivirus and Coronavirus Helicases, J. Virol., 2000, pp. 9586-9593, vol. 74, Issue 20.
Shylini, R Structure-Function Studies of The Venezuelanequine Encephalitis Virus 5'utr Promoter Element And Its Role In Attenuation of The Virus, Dissertation for Doctor of Philosophy, The University of Texas Medical Branch (2009).
Sjoberg,E et al., ASignificantly Improved Semliki Forest Virus Expression System Based on Translation Enhancer Segments from the Viral Capsid Gene, Biotechnology, Vo,. 12, pp. 1127-1131, (1994).
Smith et all, "Comparison of Biosequences", Adv. Appl. Math., 2:482-89 (1981).
Snijder, E.J., The Arterivirus Replicase, The Road from RNA to Protein(s), and Back Again, 1998, pp. 97-108. In Coronaviruses and Arteriviruses, Enjuanes et al. (ed.), Plenum Press, NY.
Snijder, E.J., Arterivirus RNA Synthesis Dissected, 2001, pp. 241-253. In The Nidoviruses (Coronaviruses and Arteriviruses), Ehud Lavi et al. (ed.), Kluwer Academic/Plenum Publishers.
Snijder et al., Proteolytic Processing of the Arterivirus Replicase, 1995, pp. 443-451. In Corona-and Related Viruses, P.J. Talbot and G.A. Levy (ed.), Plenum Press, NY.
Snijder et al., The Arterivirus Nsp2 Protease, J. Biol. Chem., 1995, p. 16671-16676, vol. 270, Issue 28.
Snijder et al., Heterodimerization of the Two Major Envelope Proteins is Essential for Arterivirus Infectivity, J. Virol., 2003, pp. 97-104, vol. 77, Issue 1.
Snijder et al., 2005. The order *Nidovirales*, pp. 390-404, In Topley and Wilson's microbiology and microbial infections, B. W. Mahy and V. ter Meulen (ed.), Hodder Arnold, London, United Kingdom.
Snijder EJ et al., "Identification of a Novel Structural Protein of Arteriviruses," J. Virol, Aug. 1999, pp. 6335-6345, vol. 37, Issue 8.

(56) References Cited

OTHER PUBLICATIONS

Stanton et al., Nucleotide sequence comparison of normal and translocated murine c-myc genes, Nature, Aug. 1984, pp. 423-425, vol. 310.
Strauss et al., The AlpahViruses: Gene Expression, Replication and Evolution, Microbiological Reviews, pp. 491-562, Sep. 1994.
Stirpe et al., Gelonin, a New Inhibitor of Protein Synthesis, Non-toxic to Intact Cells, J. Biol. Chem., Jul. 25, 1980, pp. 6947-6953, vol. 255.
Te Velthuis, et al., $Zn^{2+}$Inhibits Coronavirus and Arterivirus RNA Polymerase Activity In Vitro and Zinc Ionophores Block the Replication of these Viruses in Cell Culture, PLoS Pathogens, 2010, e1001176, pp. 1-10, vol. 6, Issue 11.
Tepper et al., Murine interleukin-4 displays potent anti-tumor activity in vivo, Cell, May 5, 1989, pp. 503-512, vol. 57.
Thaa et al., Myristoylation of the Arterivirus E Protein: The Fatty Acid Modification is not Essential for Membrane Association but Contributes Significantly to Virus Infectivity, J. Genl. Virol., 2009, pp. 2704-2712, vol. 90.
Tian et al., Arterivirus Minor Envelope Proteins Are a Major Determinant of Viral Tropism in Cell Culture, J. Virol., 2017, pp. 3701-3712, vol. 86, Issue 7.
Tijerina et al., DMS Footprinting of Structured RNAs and RNA-Protein Complexes, Nat. Protoc., 2007, pp. 2608-2623, vol. 2, Issue 10.
Tijms et al., A zinc finger-containing papain-like protease couples subgenomic mRNA synthesis to genome translation in a positive-stranded RNA virus, Proc. Natl. Acad. Sci. USA, 2001, pp. 1889-1894, vol. 98, Issue 4.
Tijms et al., Arterivirus Subgenomic mRNA Synthesis and Virion Biogenesis Depend on the Multifunctional nsp1 Autoprotease, J. Virol., Oct. 2007, pp. 10496-10505, vol. 81, Issue 19.
Toribio et al., Ilnhibition of host translation by virus infection in vivo, PNAS, vol. 107, No. 21, pp. 9837-9842, (2010).
Toribio et al., An RNA Trapping Mechanism in Alphavirus MRNA Promotes Translation and Initiation Nucleic Acids Res. 19; 44(9): pp. 4368-4380, (2016).
Tweten et al., Diphtheria toxin. Effect of substituting aspartic acid for glutamic acid 148 on ADP-ribosyltransferase activity., J. Biol. Chem., Jun. 3, 1985, pp. 10392-10394, vol. 260.
Twu et al., Hepatitis B virus X gene can transactivate heterologous viral sequences, Proc Natl. Acad. Sci. USA, Mar. 1989, pp. 2046-2050, vol. 86.
Van Aken et al., Expression, Purification, and In Vitro Activity of an Arterivirus Main Proteinase, Virus Res., 2006, pp. 97-106, vol. 120.
Van Aken et al., Mutagenesis Analysis of the nsp4 Main Proteinase Reveals Determinants of Arterivirus Replicase Polyprotein Autoprocessing, J. Virol., 2006, pp. 3428-3437, vol. 80, Issue 7.
Van Den Born et al., Discontinuous Subgenomic RNA Synthesis in Arteriviruses is Guided by an RNA Hairpin Structure Located in the Genomic Leader Region, J. Virol., 2005, pp. 6312-6324, vol. 79, Issue 10.
Van Den Born, Value of routine funduscopy in patients with hypertension: systematic review, BMJ, Jul. 9, 2005, pp. 1-5, vol. 331.
Van Den Born, et al., "An infectious recombinant equine arteritis virus expressing green fluorescent protein from its replicase gene," J. Genl. Virol., Apr. 2007, pp. 1196-1205, vol. 88.
Van Der Meer et al., ORF1a-Encoded Replicase Subunits are Involved in the Membrane Association of the Arterivirus Replication Complex, J. Virol., 1998, pp. 6689-6698, vol. 72, Issue 8.
Van Dinten, An infectious arterivirus cDNA clone: Identification of a replicase point mutation that abolishes discontinuous mRNA transcription, Proc. Natl. Acad. Sci. USA, Feb. 1997, pp. 991-996, vol. 94, Issue 3.
Van Dinten et al., Proteolytic Processing of the Open Reading Framer 1b-Encoded Part of Arterivirus Replicase is Mediated by nsp4 Serine Protease and is Essential for Virus Replication, J. Virol., 1999, pp. 2027-2037, vol. 73, Issue 3.
Van Dinten et al., The Predicted Metal-Binding Region of the Arterivirus Helicase Protein is Involved in Subgenomic mRNA Synthesis, Genome Replication, and Virion Biogenesis, J. Virol., 2000, pp. 5213-5223, vol. 74, Issue 11.
Van Hemert et al., The In Vitro RNA Synthesizing Activity of the Isolated Arterivirus Replication/Transcription Complex is Dependent on a Host Factor, J. Biol. Chem., 2008, pp. 16525-16536, vol. 283, Issue 24.
Van Kasteren et al., Arterivirus and Nairovirus Ovarian Tumor Domain-Containing Deubiquitinases Target Activated RIG-I to Control Innate Immune Signaling, J. Virol., 2011, pp. 773-785, vol. 82, Issue 2.
Van Kasteren et al., Deubiquitinase Function of Arterivirus Papain-Like Protease 2 Suppresses the Innate Immune Response in Infected Host Cells, PNAS, 2013, pp. E838-E847.
Van Marle, et al., Characterization of an Equine Arteritis Virus Replicase Mutant Defective in Subgenomic mRNA Synthesis, J. Virol., 1999, pp. 5274-5281, vol. 73, Issue 7.
Van Marle et al., Arterivirus discontinuous mRNA transcription is guided by base pairing between sense and antisense transcription-regulating sequences, Pro. Natl. Acad. Sci. USA, Aug. 6, 1999, pp. 12056-12061, vol. 96, Issue 21.
Ventoso, I., Adaptive Changes in Alphavirus mRNA Translation Allowed Colonization of Vertebrate Hosts, Journal of Virology, vol. 86, No. 17, pp. 9484-9494, (2012).
Ventoso, I. et al. Translational resistance of late alphavirus mRNA to eIF2 phosphorylation: a strategy to overcome the antiviral effect of protein kinase PKR, Genes and Development, vol. 20, pp. 87-100, (2006).
Vrudhula et al., Prodrugs of doxorubicin and melphalan and their activation by a monoclonal antibody-penicillin-G amidase conjugate, J. Med. Chem., 1993, pp. 919-923, vol. 36, Issue 7.
Ward, S. et al., Generation of CTL responses using Kunjin replicon RNA, Immunology and Cell Biology, vol. 81 , pp. 73-78, (2003).
Warner et al. Induction of the HIV-Specific and Antibody Responses in Mice Using Retroviral Vector-Transduced Cells, AIDS Res, and Human Retroviruses, vol. 7, No. 8, pp. 645-655 (1991).
Wassenaar, et al., Alternative Proteolytic Processing of the Arterivirus Replicase ORF1a Polyprotein: Evidence that NSP2 Acts as a Cofactor for the NSP4 Serine Protease, J. Virol., 1997, pp. 9313-9322, vol. 71, Issue 12.
Watanabe, et al., Exogenous expression of mouse interferon gamma cDNA in mouse neuroblastoma C1300 cells results in reduced tumorigenicity by augmented anti-tumor immunity, Proc. Natl. Acad. Sci. USA, Dec. 1989, pp. 9456-9460, vol. 86.
Weber et al., Immunotherapy of a murine tumor with interleukin 2. J. Exp. Med., 1987, pp. 1716-1733, vol. 166.
White, L. et al., Role of Alpha/Beta Interferon in Venezuelan Equine Encephalitis Virus Pathogenesis: Effect of an Attenuating Mutation in the 59 Untranslated Region, Journal of Virology, vol. 75, No. 8, pp. 3706-3718, (2001).
Wilson et al., Prospects for gene therapy of familial hypercholesterolemia, Mol. Biol. Med., Jun. 1, 1990, pp. 223-232, vol. 7, Issue 3.
Wood et al., Preproabrin: genomic cloning, characterisation and the expression of the A-chain in *Escherichia coli*, Eur. J. Biochem., 1991, pp. 723-732, vol. 198.
Yamamoto et al., The human LDL receptor: a cysteine-rich protein with multiple Alu sequences in its mRNA, Cell, Nov. 1984, pp. 27-38, vol. 39, Issue 1.
Zhou, X. et al. Self-replicating Semliki Forest virus RNA as recombinant vaccine, Vaccine, vol. 12, No. 16, pp. 1510-1514, (1994).
GenBank/NCBI accession No. J02363, dated Oct. 25, 2000; accessed Jul. 16, 2018.
GenBank accession # JX473847, dated Dec. 22, 2012; accessed Apr. 17, 2019.
GenBank/NCBI accession No. L01443.1., dated Nov. 17, 2014; accessed Oct. 3, 2016.
GenBank/NCBI accession No. L04653, dated Jun. 1, 2001; accessed Jul. 16, 2018.
GenBank/NCBI accession No. NC_001449, dated Feb. 10, 2015; accessed Jul. 16, 2018.

(56) References Cited

OTHER PUBLICATIONS

GenBank/NCBI accession No. NC_003215, dated Feb. 10, 2015; accessed Jul. 16, 2018.
GenBank/NCBI accession No. U38304; dated Feb. 10, 2015; accessed Jul. 16, 2018.
GenBank/NCBI accession No. U38305, dated Jan. 30, 2016, accessed Jul. 16, 2018.
GenBank/NCBI accession No. X04129, dated Mar. 13, 2001; accessed Jul. 16, 2018.
Boukhebza et al., "Comparative analysis of immunization schedules using a novel adenovirus-based immunotherapeutic targeting hepatitis B in naive and tolerant mouse models" Vaccine, 32(26), pp. 3258-3263, 2014.
Jones et al., "Hepatitis B virus reverse transcriptase: diverse functions as classical and emerging targets for antiviral intervention", Emerging Microbes and Infections, 2(9), e56, 9 pages, 2013.
Obeng-Adjei et al. "DNA vaccine cocktail expressing genotype A and C HBV surface and consensus core antigens generates robust cytotoxic and antibody responses and mice and Rhesus macaques" Cancer Gene Therapy, 20, 352-662, 2013.
Cohen et al. "Is chronic hepatitis B being undertreated in the United States?" J. Viral Hepat., 18(6), 377-83,2011.
Belloni et al. "IFN-a inhibits HBV transcription and replication in cell culture and in humanized mice by targeting the epigenetic regulation of the nuclear cccDNA minichromosome" J. Clin. Invest., 122(2), 529-537, 2012.
World Health Organization, Hepatitis B: Fact sheet No. 204 [Internet] Mar. 2015. Available from https://www.who.int/news-room/fact-sheets/detail/hepatitis-b, 6 pages.
Michel et al. "Therapeutic vaccines and immune-based therapies for the treatment of chronic hepatitis B: perspectives and challenges." J. Hepatol., 54(6), 1286-1296, 2011.
Reyes-Sandoval Arturo et al., "Prime-Boost Immunization with Adenoviral and Modified Vaccinia Virus Ankara Vectors Enhances the Durability and Polyfunctionality of Protective Malaria CD8(+) T-Cell Responses", Infection and Immunity, (201001), vol. 78, No. 1, pp. 145-153, XP002778539.
Perrine Martin et al., "TG1050, an immunotherapeutic to treat chronic hepatitis B, induces robust T cells and exerts an antiviral effect in HBV-persistent mice", GUT, UK, (20141126), vol. 64, No. 12, doi:10.1136/gutjnl-2014-308041, ISSN 0017-5749, pp. 1961-1971, XP055453477.
Bartenschlager et al., "Expression of the p. protein of the human hepatitis B virus in a vaccinia virus system and detection of the nucleocapsid-associated P-gene product by radiolabelling at newly introduced phosphorylation sites", Nucleic Acids Research, vol. 20, No. 2, pp. 195-202,1992.
RAMIREZ et at., "Biology of Attenuated Modified Vaccinia Virus Ankara Recombinant Vector in Mice: Virus Fate and Activation of B- and T- Cell Immune Responses in Comparision with the Western Reserve Strain and advantages as a Vaccine", Journal of Virology, Vo. 74, No. 2, pp. 923-933, 2000.

Kim, et al., "New World and Old World Alphaviruses Have Evolved to Exploit Different Components of Stress Granules, FXR and G3BP Proteins, for Assembly of Viral Replication Complexes", PLOS Pathogens, vol. 12, No. 8, p. 1-31, (Aug. 2016).
Foy, et al., "Hypervariable domains of nsP3 proteins of New World and Old World alphaviruses mediate formation of distinct, virus-specific protein complexes", J. Virol., vol. 87, No. 4, p. 1997-2010, (Dec. 2012).
Gotte, et al., "The Enigmatic Alphavirus Non-Structural Protein 3 (nsP3) Revealing Its Secrets at Last", Viruses, vol. 10, No. 3, p. 105, 1/26 to 26/26, (Feb. 2018).
Meshram, et al., "Multiple Host Factors Interact with the Hypervariable Domain of Chikungunya Virus nsP3 and Determine Viral Replication in Cell-Specific Mode", J. Virol., vol. 92, No. 16, p. 1-24, (Aug. 2018).
Frolov et al., (Journal of Virology, 1999, p. 3854-3865).
Bolz et al.: "Use of Recombinant Virus Replicon Particles for Vaccination against Mycobacterium ulcerans Disease"; PLoS Negl Trop Dis,, Aug. 14, 2015, vol. 9(8):e0004011., PDF File: p. 1-18.
Lundstrom, Kenneth L: "Replicon RNA Viral Vectors as Vaccines"; Vaccines, 2016, vol. 4(4). pii: E39. PDF File: p. 1-23.
Uematsu et al.: "Lack of Interference with Immunogenicity of a Chimeric Alphavirus Replicon Particle-Based Influenza Vaccine by Preexisting Antivector Immunity"; Clin Vaccine Immunol., Jul. 2012, vol. 19(7), p. 991-998.
Xu et al.: "Type-specific and cross-reactive antibodies induced by human papillomavirus 31 L1/L2 virus-like particle";, J Med Microbiol. 2007, vol. 56(Pt 7), p. 907-13.
Yin et. al. Similarities and Differences in Antagonism of Neuron Alpha/Beta and Sindbis Alphaviruses 2009. Journal of Virology. 83 (19) p. 10036-10047 (Year: 2009).
Mir et. al. A Multicistronic DNA Vaccine Induces Significant Protection against Tuberculosis in Mice and Offers Flexibility in the Expressed Antigen Repertoire. 2009. Clinical and Vaccine Immunology. vol. 16, No. 10. p. 1467-1475 (Year: 2009).
Araujo et al., "Expression of Hepatitis B virus surface antigen (HBsAg) from genotypes A, D and F and influence of amino acid variations related or not to genotypes on HBsAg detection," Brazilian Journal of Infectious Diseases, 20090101, vol. 13, Nr: 4.
GenBank: KT121715.1: Accession KT121715, Version KT121715. 1.2015, Sindbis virus isolate Treatmant1_population9, complete genome (Year: 2015).
GenBank: L01443.1 Accession No. L01443, 2004, Venezuelan equine encephalitis virus strain TC-83, complete genome (Year: 2004).
Jeeva S, Lee JA, Park SY, Song CS, Choi IS, Lee JB. Development of porcine respiratory and reproductive syndrome virus replicon vector for foot-and-mouth disease vaccine. Clin Exp Vaccine Res. Jan. 2014;3(1):100-9. doi: 10.7774/cevr.2014.3.1.100. Epub Dec. 18, 2013. PMID: 24427767; PMCID: PMC3890444. (Year: 2014).
Obeng-Adjei et al., "Synthetic DNA immunogen encoding hepatitis B core antigen drives immune response in liver," Cancer Gene Therapy, Nov. 5, 2012 Appleton & Lange, New York, vol. 19, Nr: 11, pp. 779-787.

* cited by examiner

FIG. 1A

```
SEQ ID NO:  2 (AURAV)  ATAGCGGACGGACTAGTACTTGTACTACAGAATTAAC-TGCCGTGTGCCGC-------------------
SEQ ID NO:  3 (CHIKV)  ATGGCTG-CGTGAGA------------CACACGTAGCCTACCAGTTCTTACTGCTCTACTCT--------
SEQ ID NO:  4 (ONNV)   ATAGCTG--CGTGATA-----------CACACACGAGCCTACGGTTTCATACTGCTCTACT---------
SEQ ID NO:  5 (RRV)    ATAGCGGGCGTGTGTGA--CACACGAGACCGTCGATTCAA-CCTTCTTGTCTCCT---------------
SEQ ID NO:  6 (SFV)    ATGGCCGGATGTGTGA--CATACACGAGACGCCAAAAGATT-TTGTTCCAGTCCT---------------
SEQ ID NO:  7 (MAYV)   ATGGCGGACAAGTGA-CACTTGTTCCGCGTCGTCGTCT-----CTAAGTCTTCCTC--------------
SEQ ID NO:  8 (GETV)   ATGGCGGACGTGTGACATCACCGTTCCGTCCTCTTTCTAG-GATCCTTTGCTAC----------------
SEQ ID NO:  9 (SAGV)   ATGGCGGACGTGTGACATCACCGTCCCTCTTTCTAG--GATCCTTTGCTAC-------------------
SEQ ID NO: 10 (NDUV)   ATGG---TGCGGAGTT-GA---GAGACGA-AGCACCAA-ACAACTACGGGCTCACC-AT-----------
SEQ ID NO: 11 (MIDV)   ATTGGTGGTTACGTA----CACGTGCCACCACCCCCA-CCCTCCAAGCGATCCA----------------
SEQ ID NO: 12 (EEEV)   ATAGGGTACGGTGTA------GAGGCAACACCACCCTAT----TTCCACTTATCCAAAATGG--------
SEQ ID NO: 13 (FMV)    ATAGGTATGGTTTA-------GAGGCGGCCTACCCTAC----TTAACGATCCAAACATGG----------
SEQ ID NO: 14 (Buggy)  ATAGGTATGGTTTA-------GAGGCGGCCTACCCTAC----TTAACGATCCAAACATGG----------
SEQ ID NO: 15 (VEEV)   ATGGCGGCCAAGA--------GAGAAGCCCAAACCAA-----TTACTACCCAAAATGGAG----------
SEQ ID NO: 16 (WHAV)   ATTGCGGGCATAGTA------CATACTATAAAGAAACAGCGACCAATTGCAC------------------
SEQ ID NO: 17 (SINV)   ATTGACGCGTAGTA-------CACACTAT-TGAATCAAACAGCAGCGACCAATTGCACT-----------
SEQ ID NO: 18 (BABV)   ATTGCGGGCGTAGTA------CACACTAT-TGAATCAAACAGCGACCAATTGCACT--------------
                       * **
```

FIG. 1B

SEQUENCE LISTING

```
<160> NUMBER OF SEQ ID NOS: 24

<210> SEQ ID NO 1
<211> LENGTH: 8364
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Rep-Alpha replicon
<220> FEATURE:
<221> NAME/KEY: misc_feature
<223> OTHER INFORMATION: T7 promoter, modified VEEV 5'UTR and
      nonstructural genes

<400> SEQUENCE: 1
taatacgact cactatagag aggcggcgca tgagagaagc ccagaccaat tacctaccca        60
aaatggagaa agttcacgtt gacatcgagg aagacagccc attcctcaga gctttgcagc       120
ggagcttccc gcagtttgag gtagaagcca agcaggtcac tgataatgac catgctaatg       180
ccagagcgtt ttcgcatctg gcttcaaaac tgatcgaaac ggaggtggac ccatccgaca       240
cgatccttga cattggaagt gcgcccgccc gcagaatgta ttctaagcac aagtatcatt       300
gtatctgtcc gatgagatgt gcggaagatc cggacagatt gtataagtat gcaactaagc       360
```

```
tgaagaaaaa ctgtaaggaa ataactgata aggaattgga caagaaaatg aaggagctcg      420
ccgccgtcat gagcgaccct gacctggaaa ctgagactat gtgcctccac gacgacgagt      480
cgtgtcgcta cgaagggcaa gtcgctgttt accaggatgt atacgcggtt gacggaccga      540
caagtctcta tcaccaagcc aataagggag ttagagtcgc ctactggata ggctttgaca      600 ccacccettt tatgtttaag aacttggctg gagcatatcc atcatactct accaactggg      660
ccgacgaaac cgtgttaacg gctcgtaaca taggcctatg cagctctgac gttatggagc      720
ggtcacgtag agggatgtcc attcttagaa agaagtattt gaaaccatcc aacaatgttc      780
tattctctgt tggctcgacc atctaccacg agaagaggga cttactgagg agctggcacc      840
tgccgtctgt atttcactta cgtggcaagc aaaattacac atgtcggtgt gagactatag      900
ttagttgcga cgggtacgtc gttaaaagaa tagctatcag tccaggcctg tatgggaagc      960
cttcaggcta tgctgctacg atgcaccgcg agggattctt gtgctgcaaa gtgacagaca     1020
cattgaacgg ggagagggtc tcttttcccg tgtgcacgta tgtgccagct acattgtgtg     1080
accaaatgac tggcatactg gcaacagatg tcagtgcgga cgacgcgcaa aaactgctgg     1140
ttgggctcaa ccagcgtata gtcgtcaacg gtcgcaccca gagaaacacc aataccatga     1200
aaaattacct tttgcccgta gtggcccagg catttgctag gtgggcaaag gaatataagg     1260
aagatcaaga agatgaaagg ccactaggac tacgagatag acagttagtc atggggtgtt     1320
gttgggcttt tagaaggcac aagataacat ctatttataa gcgcccggat acccaaacca     1380
tcatcaaagt gaacagcgat ttccactcat tcgtgctgcc caggataggc agtaacacat     1440
tggagatcgg gctgagaaca agaatcagga aaatgttaga ggagcacaag gagccgtcac     1500
ctctcattac cgccgaggac gtacaagaag ctaagtgcgc agccgatgag gctaaggagg     1560
tgcgtgaagc cgaggagttg cgcgcagctc taccaccttt ggcagctgat gttgaggagc     1620
ccactctgga agccgatgtc gacttgatgt tacaagaggc tggggccggc tcagtggaga     1680
cacctcgtgg cttgataaag gttaccagct acgatggcga ggacaagatc ggctcttacg     1740
ctgtgctttc tccgcaggct gtactcaaga gtgaaaaatt atcttgcatc caccctctcg     1800
ctgaacaagt catagtgata acacactctg gccgaaaagg gcgttatgcc gtggaaccat     1860
accatggtaa agtagtggtg ccagagggac atgcaatacc cgtccaggac tttcaagctc     1920
tgagtgaaag tgccaccatt gtgtacaacg aacgtgagtt cgtaaacagg tacctgcacc     1980
atattgccac acatggagga gcgctgaaca ctgatgaaga atattacaaa actgtcaagc     2040
ccagcgagca cgacggcgaa tacctgtacg acatcgacag gaaacagtgc gtcaagaaag     2100
aactagtcac tgggctaggg ctcacaggcg agctggtgga tcctcccttc catgaattcg     2160
cctacgagag tctgagaaca cgaccagccg ctccttacca gtaccaacc ataggggtgt     2220 atggcgtgcc aggatcaggc aagtctggca tcattaaaag cgcagtcacc aaaaaagatc     2280
tagtggtgag cgccaagaaa gaaaactgtg cagaaattat aagggacgtc aagaaaatga     2340
aagggctgga cgtcaatgcc agaactgtgg actcagtgct cttgaatgga tgcaaacacc     2400
ccgtagagac cctgtatatt gacgaagctt ttgcttgtca tgcaggtact ctcagagcgc     2460
tcatagccat tataagacct aaaaaggcag tgctctgcgg ggatcccaaa cagtgcggtt     2520 ttttaacat gatgtgcctg aaagtgcatt ttaaccacga gatttgcaca caagtcttcc     2580
acaaaagcat ctctcgccgt tgcactaaat ctgtgacttc ggtcgtctca accttgtttt     2640
acgacaaaaa aatgagaacg acgaatccga aagagactaa gattgtgatt gacactaccg     2700
```

```
gcagtaccaa acctaagcag gacgatctca ttctcacttg tttcagaggg tgggtgaagc    2760
agttgcaaat agattacaaa ggcaacgaaa taatgacggc agctgcctct caagggctga    2820
cccgtaaagg tgtgtatgcc gttcggtaca aggtgaatga aaatcctctg tacgcaccca    2880
cctctgaaca tgtgaacgtc ctactgaccc gcacggagga ccgcatcgtg tggaaaacac    2940
tagccggcga cccatggata aaaacactga ctgccaagta ccctgggaat ttcactgcca    3000
cgatagagga gtggcaagca gagcatgatg ccatcatgag gcacatcttg gagagaccgg    3060
accctaccga cgtcttccag aataaggcaa acgtgtgttg ggccaaggct ttagtgccgg    3120
tgctgaagac cgctggcata gacatgacca ctgaacaatg gaacactgtg gattattttg    3180
aaacggacaa agctcactca gcagagatag tattgaacca actatgcgtg aggttctttg    3240
gactcgatct ggactccggt ctattttctg cacccactgt tccgttatcc attaggaata    3300
atcactggga taactccccg tcgcctaaca tgtacgggct gaataaagaa gtggtccgtc    3360
agctctctcg caggtaccca caactgcctc gggcagttgc cactggaaga gtctatgaca    3420
tgaacactgg tacactgcgc aattatgatc cgcgcataaa cctagtacct gtaaacagaa    3480
gactgcctca tgctttagtc ctccaccata atgaacaccc acagagtgac ttttcttcat    3540
tcgtcagcaa attgaagggc agaactgtcc tggtggtcgg ggaaaagttg tccgtcccag    3600
gcaaaatggt tgactggttg tcagaccggc ctgaggctac cttcagagct cggctggatt    3660
taggcatccc aggtgatgtg cccaaatatg acataatatt tgttaatgtg aggaccccat    3720
ataaatacca tcactatcag cagtgtgaag accatgccat taagcttagc atgttgacca    3780
agaaagcttg tctgcatctg aatcccggcg gaacctgtgt cagcataggt tatggttacg    3840
ctgacagggc cagcgaaagc atcattggtg ctatagcgcg gcagttcaag ttttcccggg    3900
tatgcaaacc gaaatcctca cttgaagaga cggaagttct gtttgtattc attgggtacg    3960
atcgcaaggc ccgtacgcac aatccttaca agctttcatc aaccttgacc aacatttata    4020
caggttccag actccacgaa gccggatgtg caccctcata tcatgtggtg cgaggggata    4080
ttgccacggc caccgaagga gtgattataa atgctgctaa cagcaaagga caacctggcg    4140
gagggtgtg cggagcgctg tataagaaat tcccggaaag cttcgattta cagccgatcg    4200
aagtaggaaa agcgcgactg gtcaaaggtg cagctaaaca tatcattcat gccgtaggac    4260
caaacttcaa caaagtttcg gaggttgaag gtgacaaaca gttggcagag cttatgagt    4320
ccatcgctaa gattgtcaac gataacaatt acaagtcagt agcgattcca ctgttgtcca    4380
ccggcatctt ttccgggaac aaagatcgac taacccaatc attgaaccat ttgctgacag    4440
ctttagacac cactgatgca gatgtagcca tatactgcag ggacaagaaa tgggaaatga    4500
ctctcaagga agcagtggct aggagagaag cagtggagga gatatgcata tccgacgact    4560
cttcagtgac agaacctgat gcagagctgg tgagggtgca tccgaagagt tctttggctg    4620
gaaggaaggg ctacagcaca agcgatggca aaactttctc atatttggaa gggaccaagt    4680
ttcaccaggc ggccaaggat atagcagaaa ttaatgccat gtggcccgtt gcaacggagg    4740
ccaatgagca ggtatgcatg tatatcctcg gagaaagcat gagcagtatt aggtcgaaat    4800
gccccgtcga gagtcggaa gcctccacac cacctagcac gctgcccttgc ttgtgcatcc    4860
atgccatgac tccagaaaga gtacagcgcc taaaagcctc acgtccagaa caaattactg    4920
tgtgctcatc cttccattg ccgaagtata gaatcactgg tgtgcagaag atccaatgct    4980
cccagcctat attgttctca ccgaaagtgc ctgcgtatat tcatccaagg aagtatctcg    5040
tggaaacacc accggtagac gagactccgg agccatcggc agagaaccaa tccacagagg    5100
```

-continued

```
ggacacctga acaaccacca cttataaccg aggatgagac caggactaga acgcctgagc    5160
cgatcatcat cgaagaggaa gaagaggata gcataagttt gctgtcagat ggcccgaccc    5220
accaggtgct gcaagtcgag gcagacattc acgggccgcc ctctgtatct agctcatcct    5280
ggtccattcc tcatgcatcc gactttgatg tggacagttt atccatactt gacaccctgg    5340
agggagctag cgtgaccagc ggggcaacgt cagccgagac taactcttac ttcgcaaaga    5400
gtatggagtt tctggcgcga ccggtgcctg cgcctcgaac agtattcagg aaccctccac    5460
atcccgctcc gcgcacaaga acaccgtcac ttgcacccag cagggcctgc tcgagaacca    5520
gcctagtttc caccccgcca ggcgtgaata gggtgatcac tagagaggag ctcgaggcgc    5580
ttaccccgtc acgcactcct agcaggtcgg tctcgagaac cagcctggtc tccaacccgc    5640
caggcgtaaa tagggtgatt acaagagagg agtttgaggc gttcgtagca caacaacaat    5700
gacggtttga tgcgggtgca tacatctttt cctccgacac cggtcaaggg catttacaac    5760
aaaaatcagt aaggcaaacg gtgctatccg aagtggtgtt ggagaggacc gaattggaga    5820
tttcgtatgc cccgcgcctc gaccaagaaa aagaagaatt actacgcaag aaattacagt    5880
taaatcccac acctgctaac agaagcagat accagtccag gaaggtggag aacatgaaag    5940
ccataacagc tagacgtatt ctgcaaggcc tagggcatta tttgaaggca gaaggaaaag    6000
tggagtgcta ccgaaccctg catcctgttc ctttgtattc atctagtgtg aaccgtgcct    6060
tttcaagccc caaggtcgca gtggaagcct gtaacgccat gttgaaagag aactttccga    6120
ctgtggcttc ttactgtatt attccagagt acgatgccta tttggacatg gttgacggag    6180
cttcatgctg cttagacact gccagttttt gccctgcaaa gctgcgcagc tttccaaaga    6240
aacactccta tttggaaccc acaatacgat cggcagtgcc ttcagcgatc cagaacacgc    6300
tccagaacgt cctggcagct gccacaaaaa gaaattgcaa tgtcacgcaa atgagagaat    6360
tgcccgtatt ggattcggcg gcctttaatg tggaatgctt caagaaatat gcgtgtaata    6420
atgaatattg ggaaacgttt aaagaaaacc ccatcaggct tactgaagaa aacgtggtaa    6480
attacattac caaattaaaa ggaccaaaag ctgctgctct ttttgcgaag acacataatt    6540
tgaatatgtt gcaggacata ccaatggaca ggtttgtaat ggacttaaag agagacgtga    6600
aagtgactcc aggaacaaaa catactgaag aacggcccaa ggtacaggtg atccaggctg    6660
ccgatccgct agcaacagcg tatctgtgcg gaatccaccg agagctggtt aggagattaa    6720
atgcggtcct gcttccgaac attcatacac tgtttgatat gtcggctgaa gactttgacg    6780
ctattatagc cgagcacttc cagcctgggg attgtgttct ggaaactgac atcgcgtcgt    6840
ttgataaaag tgaggacgac gccatggctc tgaccgcgtt aatgattctg gaagacttag    6900
gtgtggacgc agagctgttg acgctgattg aggcggcttt cggcgaaatt tcatcaatac    6960
atttgcccac taaaactaaa tttaaattcg gagccatgat gaaatctgga atgttcctca    7020
cactgtttgt gaacacagtc attaacattg taatcgcaag cagagtgttg agagaacggc    7080
taaccggatc accatgtgca gcattcattg gagatgacaa tatcgtgaaa ggagtcaaat    7140
cggacaaatt aatggcagac aggtgcgcca cctggttgaa tatggaagtc aagattatag    7200
atgctgtggt gggcgagaaa gcgccttatt ctctgtgagg gtttatttg tgtgactccg    7260 tgaccggcac agcgtgccgt gtggcagacc ccctaaaaag gctgtttaag cttggcaaac    7320
ctctggcagc agacgatgaa catgatgatg acaggagaag gcattgcat gaagagtcaa    7380 cacgctggaa ccgagtgggt attctttcag agctgtgcaa ggcagtagaa tcaaggtatg    7440
```

```
aaaccgtagg aacttccatc atagttatgg ccatgactac tctagctagc agtgttaaat    7500
cattcagcta cctgagaggg gcccctataa ctctctacgg ctaacctgaa tggactacga    7560
catagtctag tccgccaaga tatcatcgat acagcagcaa ttggcaagct gcttacatag    7620
aaggcgcgcc gtttaaacgg ccggccttaa ttaagtaacg atacagcagc aattggcaag    7680
ctgcttacat agaactcgcg gcgattggca tgccgcttta aaattttat tttatttttc      7740 ttttcttttc cgaatcggat tttgtttta atatttcaaa aaaaaaaaaa aaaaaaaaa       7800 aaaaaaaaa aaaaaaccc ctctctaaac ggaggggttt ttttcagcgt aactggactg       7860
gccacagtta ggcggccgcg catgttcatc atcagtaacc cgtatcgtga gcatcctctc    7920
tcgtttcatc ggtatcatta cctccatgaa cagaaatccc ccttacacgg aggcatcagt    7980
gaccaaacag gaaaaaaccg cccttaacat ggcccgcttt atcagaagcc agacattaac    8040
gcttctggag aaactcaacg agctggacgc ggatgaacag gcagacatct gtgaatcgct    8100
tcacgaccac gctgatgagc tttaccgcag ctgcctcgcg cgtttcggtg atgacggtga    8160
aaacctctga cacatgcagc tcccggagac ggtcacagct tgtctgtaag cggatgccgg    8220
gagcagacaa gcccgtcagg gcgcgtcagc gggtgttggc gggtgtcggg gcgcagccat    8280
gacccagtca cgtagcgata gcggagtgta tactggctta actatgcggc atcagagcag    8340
attgtactga gagtgcacca tatg                                           8364

<210> SEQ ID NO 2
<211> LENGTH: 50
<212> TYPE: DNA
<213> ORGANISM: Aura virus
<220> FEATURE:
<221> NAME/KEY: misc_feature
<223> OTHER INFORMATION: 5'UTR

<400> SEQUENCE: 2
atagcggacg gactagtact tgtactacag aattaactgc cgtgtgccgc                50

<210> SEQ ID NO 3
<211> LENGTH: 50
<212> TYPE: DNA
<213> ORGANISM: Chikungunya virus
<220> FEATURE:
<221> NAME/KEY: misc_feature
<223> OTHER INFORMATION: 5'UTR

<400> SEQUENCE: 3
atggctgcgt gagacacacg tagcctacca gtttcttact gctctactct                50

<210> SEQ ID NO 4
<211> LENGTH: 50
<212> TYPE: DNA
<213> ORGANISM: O'Nyong-Nyong virus
<220> FEATURE:
<221> NAME/KEY: misc_feature
<223> OTHER INFORMATION: 5'UTR

<400> SEQUENCE: 4
atagctgcgt gatacacaca cgcagcttac gggtttcata ctgctctact                50

<210> SEQ ID NO 5
<211> LENGTH: 50
<212> TYPE: DNA
<213> ORGANISM: Bebaru virus
<220> FEATURE:
<221> NAME/KEY: misc_feature
<223> OTHER INFORMATION: 5'UTR
```

```
<400> SEQUENCE: 5
atggcggctg tgtgacacac gagccgtcga tttcaacctt cttgctccct             50

<210> SEQ ID NO 6
<211> LENGTH: 50
<212> TYPE: DNA
<213> ORGANISM: Semliki Forest virus
<220> FEATURE:
<221> NAME/KEY: misc_feature
<223> OTHER INFORMATION: 5'UTR

<400> SEQUENCE: 6
atggcggatg tgtgacatac acgacgccaa aagatttttgt tccagctcct            50

<210> SEQ ID NO 7
<211> LENGTH: 50
<212> TYPE: DNA
<213> ORGANISM: Mayaro virus
<220> FEATURE:
<221> NAME/KEY: misc_feature
<223> OTHER INFORMATION: 5'UTR

<400> SEQUENCE: 7
atggcgggca agtgacactt gttccgccgg tcgtctctaa gctcttcctc             50

<210> SEQ ID NO 8
<211> LENGTH: 50
<212> TYPE: DNA
<213> ORGANISM: Getah virus
<220> FEATURE:
<221> NAME/KEY: misc_feature
<223> OTHER INFORMATION: 5'UTR

<400> SEQUENCE: 8
atggcggacg tgtgacatca ccgttcgctc tttctaggat cctttgctac             50

<210> SEQ ID NO 9
<211> LENGTH: 50
<212> TYPE: DNA
<213> ORGANISM: Sagiyama virus
<220> FEATURE:
<221> NAME/KEY: misc_feature
<223> OTHER INFORMATION: 5'UTR

<400> SEQUENCE: 9
atggcggacg tgtgacatca ccgttcgctc tttctaggat cctttgctac             50

<210> SEQ ID NO 10
<211> LENGTH: 50
<212> TYPE: DNA
<213> ORGANISM: Ndumu virus
<220> FEATURE:
<221> NAME/KEY: misc_feature
<223> OTHER INFORMATION: 5'UTR

<400> SEQUENCE: 10
atggtgcgga gttgagagac gaagcaccaa acaactacgc ggctcaccat             50

<210> SEQ ID NO 11
<211> LENGTH: 50
<212> TYPE: DNA
<213> ORGANISM: Middleburg virus
<220> FEATURE:
<221> NAME/KEY: misc_feature
<223> OTHER INFORMATION: 5'UTR
```

<400> SEQUENCE: 11
attggtggtt acgtacacgt gccaccaccc cccaccctcc aagcgatcca        50

<210> SEQ ID NO 12
<211> LENGTH: 50
<212> TYPE: DNA
<213> ORGANISM: Eastern equine encephalitis virus
<220> FEATURE:
<221> NAME/KEY: misc_feature
<223> OTHER INFORMATION: 5'UTR

<400> SEQUENCE: 12
atagggtacg gtgtagaggc aaccaccta tttccaccta tccaaaatgg         50

<210> SEQ ID NO 13
<211> LENGTH: 50
<212> TYPE: DNA
<213> ORGANISM: Fort Morgan virus
<220> FEATURE:
<221> NAME/KEY: misc_feature
<223> OTHER INFORMATION: 5'UTR

<400> SEQUENCE: 13
atagggtatg gtttagaggc gcctacccta cttaaccgat ccaaacatgg        50

<210> SEQ ID NO 14
<211> LENGTH: 50
<212> TYPE: DNA
<213> ORGANISM: Buggy Creek virus
<220> FEATURE:
<221> NAME/KEY: misc_feature
<223> OTHER INFORMATION: 5'UTR

<400> SEQUENCE: 14
atagggtatg gtttagaggc gcctacccta cttaaccgat ccaaacatgg        50

<210> SEQ ID NO 15
<211> LENGTH: 50
<212> TYPE: DNA
<213> ORGANISM: Venezuelan equine encephalitis virus
<220> FEATURE:
<221> NAME/KEY: misc_feature
<223> OTHER INFORMATION: 5'UTR

<400> SEQUENCE: 15
atgggcggcg caagagagaa gcccaaacca attacctacc caaaatggag        50

<210> SEQ ID NO 16
<211> LENGTH: 50
<212> TYPE: DNA
<213> ORGANISM: Whataroa virus
<220> FEATURE:
<221> NAME/KEY: misc_feature
<223> OTHER INFORMATION: 5'UTR

<400> SEQUENCE: 16
attggcggca tagtacatac tatataaaag aaacagccga ccaattgcac        50

<210> SEQ ID NO 17
<211> LENGTH: 50
<212> TYPE: DNA
<213> ORGANISM: Sindbis virus
<220> FEATURE:
<221> NAME/KEY: misc_feature
<223> OTHER INFORMATION: 5'UTR

<400> SEQUENCE: 17

```
attgacggcg tagtacacac tattgaatca acagccgac caattgcact              50
```

<210> SEQ ID NO 18
<211> LENGTH: 50
<212> TYPE: DNA
<213> ORGANISM: Bebaru virus
<220> F

```
aagatcaaga agatgaaagg ccactaggac tacgagatag acagttagtc atggggtgtt    1320
gttgggcttt tagaaggcac aagataacat ctatttataa gcgcccggat acccaaacca    1380
tcatcaaagt gaacagcgat ttccactcat tcgtgctgcc caggataggc agtaacacat    1440
tggagatcgg gctgagaaca agaatcagga aaatgttaga ggagcacaag gagccgtcac    1500
ctctcattac cgccgaggac gtacaagaag ctaagtgcgc agccgatgag gctaaggagg    1560
tgcgtgaagc cgaggagttg cgcgcagctc taccacctt ggcagctgat gttgaggagc     1620
ccactctgga agccgatgtc gacttgatgt tacaagaggc tggggccggc tcagtggaga    1680
cacctcgtgg cttgataaag gttaccagct acgatgcga ggacaagatc ggctcttacg      1740
ctgtgctttc tccgcaggct gtactcaaga gtgaaaaatt atcttgcatc caccctctcg    1800
ctgaacaagt catagtgata acacactctg gccgaaaagg gcgttatgcc gtggaaccat    1860
accatggtaa agtagtggtg ccagagggac atgcaatacc cgtccaggac tttcaagctc    1920
tgagtgaaag tgccaccatt gtgtacaacg aacgtgagtt cgtaaacagg tacctgcacc    1980
atattgccac acatggagga gcgctgaaca ctgatgaaga atattacaaa actgtcaagc    2040
ccagcgagca cgacggcgaa tacctgtacg acatcgacag gaaacagtgc gtcaagaaag    2100
aactagtcac tgggctaggg ctcacaggcg agctggtgga tcctcccttc catgaattcg    2160
cctacgagag tctgagaaca cgaccagccg ctccttacca agtaccaacc ataggggtgt    2220
atggcgtgcc aggatcaggc aagtctggca tcattaaaag cgcagtcacc aaaaaagatc    2280
tagtggtgag cgccaagaaa gaaaactgtg cagaaattat aagggacgtc aagaaaatga    2340
aagggctgga cgtcaatgcc agaactgtgg actcagtgct cttgaatgga tgcaaacacc    2400
ccgtagagac cctgtatatt gacgaagctt ttgcttgtca tgcaggtact ctcagagcgc    2460
tcatagccat tataagacct aaaaaggcag tgctctgcgg ggatcccaaa cagtgcggtt    2520
tttttaacat gatgtgcctg aaagtgcatt ttaaccacga gatttgcaca caagtcttcc    2580
acaaaagcat ctctcgccgt tgcactaaat ctgtgacttc ggtcgtctca accttgtttt    2640
acgacaaaaa aatgagaacg acgaatccga aagagactaa gattgtgatt gacactaccg    2700
gcagtaccaa acctaagcag gacgatctca ttctcacttg tttcagaggg tgggtgaagc    2760
agttgcaaat agattacaaa ggcaacgaaa taatgacggc agctgcctct caagggctga    2820
cccgtaaagg tgtgtatgcc gttcggtaca aggtgaatga aaatcctctg tacgcaccca    2880
cctctgaaca tgtgaacgtc ctactgaccc gcacggagga ccgcatcgtg tggaaaacac    2940
tagccggcga cccatggata aaaacactga ctgccaagta ccctgggaat ttcactgcca    3000
cgatagagga gtggcaagca gagcatgatg ccatcatgag gcacatcttg gagagaccgg    3060
accctaccga cgtcttccag aataaggcaa acgtgtgttg ggccaaggct ttagtgccgg    3120
tgctgaagac cgctggcata gacatgacca ctgaacaatg gaacactgtg gattattttg    3180
aaacggacaa agctcactca gcagagatag tattgaacca actatgcgtg aggttctttg    3240
gactcgatct ggactccggt ctatttttctg cacccactgt tccgttatcc attaggaata    3300
atcactggga taactccccg tcgcctaaca tgtacgggct gaataaagaa gtggtccgtc    3360
agctctctcg caggtaccca caactgcctc gggcagttgc cactggaaga gtctatgaca    3420
tgaacactgg tacactgcgc aattatgatc cgcgcataaa cctagtacct gtaaacagaa    3480
gactgcctca tgctttagtc ctccaccata tgaacaccc acagagtgac ttttcttcat     3540
tcgtcagcaa attgaagggc agaactgtcc tggtggtcgg ggaaaagttg tccgtcccag    3600
```

```
gcaaaatggt tgactggttg tcagaccggc ctgaggctac cttcagagct cggctggatt    3660
taggcatccc aggtgatgtg cccaaatatg acataatatt tgttaatgtg aggacccat     3720 ataaatacca tcactatcag cagtgtgaag accatgccat taagcttagc atgttgacca    3780
agaaagcttg tctgcatctg aatcccggcg gaacctgtgt cagcataggt tatggttacg    3840
ctgacagggc cagcgaaagc atcattggtg ctatagcgcg gcagttcaag ttttcccggg    3900
tatgcaaacc gaaatcctca cttgaagaga cggaagttct gtttgtattc attgggtacg    3960
atcgcaaggc ccgtacgcac aatccttaca agctttcatc aaccttgacc aacatttata    4020
caggttccag actccacgaa gccggatgtg caccctcata tcatgtggtg cgaggggata    4080
ttgccacggc caccgaagga gtgattataa atgctgctaa cagcaaagga caacctggcg    4140
gaggggtgtg cggagcgctg tataagaaat cccggaaag cttcgattta cagccgatcg     4200
aagtaggaaa agcgcgactg gtcaaaggtg cagctaaaca tatcattcat gccgtaggac    4260
caaacttcaa caaagtttcg gaggttgaag gtgacaaaca gttggcagag cttatgagt     4320 ccatcgctaa gattgtcaac gataacaatt acaagtcagt agcgattcca ctgttgtcca    4380
ccggcatctt ttccgggaac aaagatcgac taacccaatc attgaaccat tgctgacag     4440 ctttagacac cactgatgca gatgtagcca tatactgcag ggacaagaaa tgggaaatga    4500
ctctcaagga agcagtggct aggagagaag cagtggagga gatatgcata tccgacgact    4560
cttcagtgac agaacctgat gcagagctgg tgagggtgca tccgaagagt tctttggctg    4620
gaaggaaggg ctacagcaca agcgatggca aactttctc atatttggaa gggaccaagt     4680
ttcaccaggc ggccaaggat atagcagaaa ttaatgccat gtggcccgtt gcaacggagg    4740
ccaatgagca ggtatgcatg tatatcctcg gagaaagcat gagcagtatt aggtcgaaat    4800
gccccgtcga agagtcggaa gcctccacac cacctagcac gctgccttgc ttgtgcatcc    4860
atgccatgac tccagaaaga gtacagcgcc taaaagcctc acgtccagaa caaattactg    4920
tgtgctcatc ctttccattg ccgaagtata gaatcactgg tgtgcagaag atccaatgct    4980
cccagcctat attgttctca ccgaaagtgc ctgcgtatat tcatccaagg aagtatctcg    5040
tggaaacacc accggtagac gagactccgg agccatcggc agagaaccaa tccacagagg    5100
ggacacctga acaaccacca cttataaccg aggatgagac caggactaga acgcctgagc    5160
cgatcatcat cgaagaggaa gaagaggata gcataagttt gctgtcagat ggcccgaccc    5220
accaggtgct gcaagtcgag gcagacattc acgggccgcc ctctgtatct agctcatcct    5280
ggtccattcc tcatgcatcc gactttgatg tggacagttt atccatactt gacacccctgg   5340 agggagctag cgtgaccagc ggggcaacgt cagccgagac taactcttac ttcgcaaaga    5400
gtatggagtt tctggcgcga ccggtgcctg cgcctcgaac agtattcagg aaccctccac    5460
atcccgctcc gcgcacaaga acaccgtcac ttgcacccag cagggcctgc tcgagaacca    5520
gcctagtttc caccccgcca ggcgtgaata gggtgatcac tagagaggag ctcgaggcgc    5580
ttaccccgtc acgcactcct agcaggtcgg tctcgagaac cagcctggtc tccaacccgc    5640
caggcgtaaa tagggtgatt acaagagagg agtttgaggc gttcgtagca caacaacaat    5700
gacggtttga tgcgggtgca tacatctttt cctccgacac cggtcaaggg catttacaac    5760
aaaaatcagt aaggcaaacg gtgctatccg aagtggtgtt ggagaggacc gaattggaga    5820
tttcgtatgc cccgcgcctc gaccaagaaa aagaagaatt actacgcaag aaattacagt    5880
taaatcccac acctgctaac agaagcagat accagtccag gaaggtggag aacatgaaag    5940
ccataacagc tagacgtatt ctgcaaggcc tagggcatta tttgaaggca gaaggaaaag    6000
```

```
tggagtgcta ccgaaccctg catcctgttc ctttgtattc atctagtgtg aaccgtgcct    6060
tttcaagccc caaggtcgca gtggaagcct gtaacgccat gttgaaagag aacttccga    6120 ctgtggcttc ttactgtatt attccagagt acgatgccta tttggacatg gttgacggag    6180
cttcatgctg cttagacact gccagttttt gccctgcaaa gctgcgcagc tttccaaaga    6240
aacactccta tttggaaccc acaatacgat cggcagtgcc ttcagcgatc cagaacacgc    6300
tccagaacgt cctggcagct gccacaaaaa gaaattgcaa tgtcacgcaa atgagagaat    6360
tgcccgtatt ggattcggcg gcctttaatg tggaatgctt caagaaatat gcgtgtaata    6420
atgaatattg ggaaacgttt aaagaaaacc ccatcaggct tactgaagaa aacgtggtaa    6480
attacattac caaattaaaa ggaccaaaag ctgctgctct ttttgcgaag acacataatt    6540
tgaatatgtt gcaggacata ccaatggaca ggtttgtaat ggacttaaag agagacgtga    6600
aagtgactcc aggaacaaaa catactgaag aacggcccaa ggtacaggtg atccaggctg    6660
ccgatccgct agcaacagcg tatctgtgcg gaatccaccg agagctggtt aggagattaa    6720
atgcggtcct gcttccgaac attcatacac tgtttgatat gtcggctgaa gactttgacg    6780
ctattatagc cgagcacttc cagcctgggg attgtgttct ggaaactgac atcgcgtcgt    6840
ttgataaaag tgaggacgac gccatggctc tgaccgcgtt aatgattctg gaagacttag    6900
gtgtggacgc agagctgttg acgctgattg aggcggcttt cggcgaaatt tcatcaatac    6960
atttgcccac taaaactaaa tttaaattcg gagccatgat gaaatctgga atgttcctca    7020
cactgtttgt gaacacagtc attaacattg taatcgcaag cagagtgttg agagaacggc    7080
taaccggatc accatgtgca gcattcattg gagatgacaa tatcgtgaaa ggagtcaaat    7140
cggacaaatt aatggcagac aggtgcgcca cctggttgaa tatggaagtc aagattatag    7200
atgctgtggt gggcgagaaa gcgccttatt tctgtggagg gtttattttg tgtgactccg    7260
tgaccggcac agcgtgccgt gtggcagacc ccctaaaaag gctgtttaag cttggcaaac    7320
ctctggcagc agacgatgaa catgatgatg acaggagaag ggcattgcat gaagagtcaa    7380
cacgctggaa ccgagtgggt attctttcag agctgtgcaa ggcagtagaa tcaaggtatg    7440
aaaccgtagg aacttccatc atagttatgg ccatgactac tctagctagc agtgttaaat    7500
cattcagcta cctgagaggg gccccctataa ctctctacgg ctaacctgaa tggactacga    7560
catagtctag tccgccaaga tatcgcacca tggaaaatat ggaaacgac gagaacatcg    7620 tggtgggccc caagcccttc taccccatcg aggaaggcag cgccggcacc cagctgcgga    7680
agtacatgga aagatacgcc aagctgggcg ccattgcctt caccaacgcc gtgaccggcg    7740
tggactacag ctacgccgag tacctggaaa agagctgctg cctgggcaag gctctgcaga    7800 actacgcct ggtggtggac ggccggatcg ccctgtgcag cgagaactgc gaggaattct    7860
tcatccccgt gatcgccggc ctgttcatcg gcgtgggcgt ggctcccacc aacgagatct    7920 acacctgcg ggagctggtg cacagcctgg gcatcagcaa gccaccatc gtgttcagca    7980 gcaagaaggg cctggacaaa gtcatcaccg tgcagaaaac cgtgaccacc atcaagacca    8040
tcgtgatcct ggacagcaag gtggactacc ggggctacca gtgcctggac accttcatca    8100
agcggaacac ccccctggc ttccaggcca gcagcttcaa gaccgtggag gtggaccgga    8160
aagaacaggt ggccctgatc atgaacagca gcggcagcac cggcctgccc aagggcgtgc    8220
agctgaccca cgagaacacc gtgacccggt tcagccacgc cagggacccc atctacggca    8280
accaggtgtc ccccggcacc gccgtgctga ccgtggtgcc cttccaccac ggcttcggca    8340
```

```
tgttcaccac cctgggctac ctgatctgcg gcttccgggt ggtgatgctg accaagttcg    8400
acgaggaaac cttcctgaaa accctgcagg actacaagtg cacctacgtg attctggtgc    8460
ccaccctgtt cgccatcctg aacaagagcg agctgctgaa caagtacgac ctgagcaacc    8520
tggtggagat cgccagcggc ggagcccccc tgagcaaaga agtgggagag gccgtcgcca    8580
ggcggttcaa tctgcccggc gtgcggcagg gctacggcct gaccgagaca accagcgcca    8640
tcatcatcac ccccgagggc gacgacaagc tggagccag cggcaaggtg gtgcccctgt     8700
tcaaggccaa agtgatcgac ctggacacca agaagagcct gggccccaac agacggggcg    8760
aagtgtgcgt gaagggcccc atgctgatga agggctacgt gaacaacccc gaggccacca    8820
agagctgat cgacgaagag ggctggctgc acaccggcga catcggctac tacgacgaag     8880
agaagcactt cttcatcgtg gaccggctga gagcctgat caagtacaag gctatcagg     8940
tgcccctgc cgagctggaa agcgtcctgc tgcagcaccc cagcatcttc gacgccggcg     9000
tggccggggt gccagatcct gtggccggcg agctgcctgg cgccgtggtg gtgctggaat    9060
ccggcaagaa catgaccgag aaagaagtga tggactacgt cgccagccag gtgtccaacg    9120
ccaagcggct gagaggcggc gtgagattcg tggacgaagt gccaaggggc ctgaccggca    9180
agatcgacgg cagggccatc cgggagatcc tgaagaaacc cgtggccaag atgtgattaa    9240
ttgatcgata cagcagcaat tggcaagctg cttacataga aggcgcgccg tttaaacggc    9300
cggccttaat taagtaacga tacagcagca attggcaagc tgcttacata gaactcgcgg    9360
cgattggcat gccgctttaa aattttatt ttattttttct tttcttttcc gaatcggatt    9420
ttgttttaa tatttcaaaa aaaaaaaaaa aaaaaaaaaa aaaaaaaaaa aaaaaa         9476

<210> SEQ ID NO 20
<211> LENGTH: 1647
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: Red Firefly reporter gene - rFF

<400> SEQUENCE: 20
atggaaaata tggaaaacga cgagaacatc gtggtgggcc ccaagccctt ctaccccatc      60
gaggaaggca gcgccggcac ccagctgcgg aagtacatgg aaagatacgc caagctgggc     120
gccattgcct tcaccaacgc cgtgaccggc gtggactaca gctacgccga gtacctggaa     180
aagagctgct gcctgggcaa ggctctgcag aactacggcc tggtggtgga cggccggatc     240
gccctgtgca gcgagaactg cgaggaattc ttcatccccg tgatcgccgg cctgttcatc     300
ggcgtgggcg tggctcccac caacgagatc tacaccctgc gggagctggt gcacagcctg     360
ggcatcagca agcccaccat cgtgttcagc agcaagaagg gcctggacaa agtcatcacc     420
gtgcagaaaa ccgtgaccac catcaagacc atcgtgatcc tggacagcaa ggtggactac     480
cggggctacc agtgcctgga caccttcatc aagcggaaca ccccccctgg cttccaggcc     540
agcagcttca gaccgtgga ggtggaccgg aaagaacagg tggccctgat catgaacagc     600
agcggcagca ccggcctgcc caagggcgtg cagctgaccc acgagaacac cgtgacccgg     660
ttcagccacg ccaggacc catctacggc aaccaggtgt ccccggcac cgccgtgctg        720
accgtggtgc cctccaccca cggcttcggc atgttcacca ccctgggcta cctgatctgc     780
ggcttccggg tggtgatgct gaccaagttc gacgaggaaa ccttcctgaa aaccctgcag     840
```

```
gactacaagt gcacctacgt gattctggtg cccaccctgt tcgccatcct gaacaagagc    900
gagctgctga acaagtacga cctgagcaac ctggtggaga tcgccagcgg cggagccccc    960
ctgagcaaag aagtgggaga ggccgtcgcc aggcggttca atctgcccgg cgtgcggcag   1020
ggctacggcc tgaccgagac aaccagcgcc atcatcatca cccccgaggg cgacgacaag   1080
cctggagcca gcggcaaggt ggtgcccctg ttcaaggcca agtgatcga cctggacacc   1140 aagaagagcc tgggccccaa cagacggggc gaagtgtgcg tgaagggccc catgctgatg   1200
aagggctacg tgaacaaccc cgaggccacc aaagagctga tcgacgaaga gggctggctg   1260
cacaccggcg acatcggcta ctacgacgaa gagaagcact tcttcatcgt ggaccggctg   1320
aagagcctga tcaagtacaa gggctatcag gtgcccctg ccgagctgga aagcgtcctg   1380
ctgcagcacc ccagcatctt cgacgccggc gtggccgggg tgccagatcc tgtggccggc   1440
gagctgcctg cgccgtggt ggtgctggaa tccggcaaga acatgaccga aaagaagtg   1500 atggactacg tcgccagcca ggtgtccaac gccaagcggc tgagaggcgg cgtgagattc   1560
gtggacgaag tgccaaaggg cctgaccggc aagatcgacg caggcccat ccgggagatc   1620 ctgaagaaac ccgtggccaa gatgtga                                      1647

<210> SEQ ID NO 21
<211> LENGTH: 729
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: EGFP

<400> SEQUENCE: 21
atgggaagag ccggcgtgag caagggcgag gagctgttca ccggggtggt gcccatcctg     60
gtcgagctgg acggcgacgt aaacggccac aagttcagcg tgtccggcga gggcgagggc    120
gatgccacct acggcaagct gaccctgaag ctgatctgca ccaccggcaa gctgcccgtg    180
ccctggccca ccctcgtgac cacccctggc tacggcctgc agtgcttcgc ccgctacccc    240
gaccacatga agcagcacga cttcttcaag tccgccatgc ccgaaggcta cgtccaggag    300
cgcaccatct tcttcaagga cgacggcaac tacaagaccc gcgccgaggt gaagttcgag    360
ggcgacaccc tggtgaaccg catcgagctg aagggcatcg acttcaagga ggacggcaac    420
atcctggggc acaagctgga gtacaactac aacagccaca acgtctatat caccgccgac    480
aagcagaaga acggcatcaa ggccaacttc aagatccgcc acaacatcga ggacggcggc    540
gtgcagctcg ccgaccacta ccagcagaac acccccatcg gcgacggccc cgtgctgctg    600
cccgacaacc actacctgag ctaccagtcc gccctgagca agaccccaa cgagaagcgc    660 gatcacatgg tcctgctgga gttcgtgacc gccgccggga tcactctcgg catggacgag    720
ctgtacaag                                                           729

<210> SEQ ID NO 22
<211> LENGTH: 1707
<212> TYPE: DNA
<213> ORGANISM: Artificial Sequence
<220> FEATURE:
<223> OTHER INFORMATION: Synthetic polynucleotide
<220> FEATURE:
<221> NAME/KEY: misc_feature
<223> OTHER INFORMATION: HA Influenza A virus
      A-VietNam-1203-2004 (H5N1) - GenBank
```

<400> SEQUENCE: 22

```
atggagaaaa tagtgcttct ttttgcaata gtcagtcttg ttaaaagtga tcagatttgc      60
attggttacc atgcaaacaa ctcgacagag caggttgaca caataatgga aaagaacgtt     120
actgttacac atgcccaaga catactggaa aagaaacaca acgggaagct ctgcgatcta     180
gatggagtga agcctctaat tttgagagat tgtagcgtag ctggatggct cctcggaaac     240
ccaatgtgtg acgaattcat caatgtgccg aatggtcttc atagtggaga aggccaat      300
ccagtcaatg acctctgtta cccagggat ttcaatgact atgaagaatt gaaacaccta      360
ttgagcagaa taaccatt tgagaaaatt cagatcatcc caaaagttc ttggtccagt       420
catgaagcct cattaggggt gagctcagca tgtccatacc agggaaagtc ctccttttc     480
agaaatgtgg tatggcttat caaaaagaac agtacatacc aacaataaa gaggagctac     540
aataatacca accaagaaga tcttttggta ctgtggggga ttcaccatcc taatgatgcg    600
gcagagcaga caaagctcta tcaaaaccca accacctata tttccgttgg gacatcaaca    660
ctaaaccaga gattggtacc aagaatagct actagatcca agtaaacgg gcaaagtgga    720
aggatggagt tcttctggac aattttaaag ccgaatgatg caatcaactt cgagagtaat    780
ggaaatttca ttgctccaga atatgcatac aaaattgtca gaaaggga ctcaacaatt     840
atgaaagtg aattggaata tggtaactgc aacaccaagt gtcaaactcc aatggggcg     900
ataaactcta gcatgccatt ccacaatata cccctctca ccattgggga atgccccaaa     960
tatgtgaaat caaacagatt agtccttgcg actgggctca gaaatagccc tcaaagagag   1020
agaagaagaa aaaagagagg attatttgga gctatagcag gttttataga gggaggatgg   1080
cagggaatgg tagatggttg gtatgggtac caccatagca atgagcaggg gagtgggtac   1140
gctgcagaca agaatccac tcaaaaggca atagatggag tcaccaataa ggtcaactcg   1200
atcattgaca aaatgaacac tcagtttgag gccgttggaa gggaatttaa caacttagaa   1260
aggagaatag agaattaaa caagaagatg aagacgggt tcctagatgt ctggacttat    1320
aatgctgaac ttctggttct catggaaaat gagagaactc tagactttca tgactcaaat   1380
gtcaagaacc tttacgacaa ggtccgacta cagcttaggg ataatgcaaa ggagctgggt    1440
aacggttgtt tcgagttcta tcataaatgt gataatgaat gtatggaaag tgtaagaaat   1500
ggaacgtatg actacccgca gtattcagaa gaagcgagac taaaaagaga ggaaataagt   1560
ggagtaaaat tggaatcaat aggaatttac caaatactgt caatttattc tacagtggcg   1620
agttccctag cactggcaat catggtagct ggtctatcct tatggatgtg ctccaatggg   1680
tcgttacaat gcagaatttg catttaa                                       1707
```

<210> SEQ ID NO 23
<211> LENGTH: 29
<212> TYPE: DNA
<213> ORGANISM: Artificial Sequence
<220> FEATURE:
<223> OTHER INFORMATION: Synthetic polynucleotide
<220> FEATURE:
<223> OTHER INFORMATION: VEE 5' T-G nt 2 F - Forward Primer

<400> SEQUENCE: 23

```
cgactcacta tagagaggcg gcgcatgag                                       29
```

<210> SEQ ID NO 24
<211> LENGTH: 29
<212> TYPE: DNA
<213> ORGANISM: Artificial Sequence

```
<220> FEATURE:
<223> OTHER INFORMATION: Synthetic polynucleotide
<220> FEATURE:
<223> OTHER INFORMATION: VEE 5' T-G nt 2 R - Reverse Primer

<400> SEQUENCE: 24
ctcatgcgcc gcctctctat agtgagtcg                                    29
```

RECOMBINANT VIRUS REPLICON SYSTEMS AND USES THEREOF

RELATED APPLICATIONS

The present application claims priority to U.S. Provisional Application No. 62/409,228 filed on Oct. 17, 2016, which is herein expressly incorporated by reference in its entirety.

INCORPORATION OF THE SEQUENCE LISTING

The material in the accompanying sequence listing is hereby incorporated by reference into this application. The accompanying sequence listing text file, name SGI011A_SeqListing.txt, was created on Sep. 19, 2017 and is 34 KB.

FIELD

The present disclosure relates to the field of molecular biology, including nucleic acid molecules comprising modified viral replicons and the use of such nucleic acid molecules for production of desired products in suitable host cells in cell culture or in a living body.

BACKGROUND

In recent years, several different groups of animal viruses have been subjected to genetic manipulation either by homologous recombination or by direct engineering of their genomes. The availability of reverse genetics systems for both DNA and RNA viruses has created new perspectives for the use of recombinant viruses, for example, as vaccines, expression vectors, anti-tumor agents, gene therapy vectors, and drug delivery vehicles.

For example, many viral-based expression vectors have been deployed for expression of heterologous proteins in cultured recombinant cells. In particular, the application of modified viral vectors for gene expression in host cells continues to expand. Recent advances in this regard include further development of techniques and systems for production of multi-subunit protein complexes, and co-expression of protein-modifying enzymes to improve heterologous protein production. Other recent progresses regarding viral expression vector technologies include many advanced genome engineering applications for controlling gene expression, preparation of viral vectors, in vivo gene therapy applications, and creation of vaccine delivery vectors.

However, there is still a need for more efficient methods and systems for expressing genes of interest in recombinant expression systems.

SUMMARY

This section provides a general summary of the present application, and is not comprehensive of its full scope or all of its features.

In one aspect, disclosed herein is a nucleic acid molecule including a modified replicon RNA, in which the modified replicon RNA includes a modified 5'-UTR and is devoid of at least a portion of a nucleic acid sequence encoding viral structural proteins. In various embodiments of this aspect and other aspects of the present disclosure, the nucleic acid molecule as disclosed herein can include one or more of the following features. In some embodiments, the modified replicon RNA is a modified alphavirus replicon RNA. In some embodiments, the modified alphavirus replicon RNA includes a modified alphavirus genome. In some embodiments, the modified 5'-UTR includes one or more nucleotide substitutions at position 1, 2, 4, or a combination thereof. In some embodiments, at least one of the nucleotide substitutions is a nucleotide substitution at position 2 of the modified 5'-UTR. In some embodiments, the nucleotide substitutions at position 2 of the modified 5'-UTR is a U→G substitution.

In some embodiments, the nucleic acid molecule includes a modified replicon RNA which is devoid of a substantial portion of the nucleic acid sequence encoding viral structural proteins. In some embodiments, the modified alphavirus genome or replicon RNA as disclosed herein includes no nucleic acid sequence encoding viral structural proteins.

In various embodiments of this aspect and other aspects of the present disclosure, the nucleic acid molecule further includes one or more expression cassettes, wherein each of the expression cassettes includes a promoter operably linked to a heterologous nucleic acid sequence. In some embodiments, the nucleic acid molecule includes at least two, three, four, five, or six expression cassettes. In some embodiments, the promoter of at least one of the expression cassettes is or comprises a 26S subgenomic promoter.

In some embodiments, the heterologous nucleic acid sequence of at least one of the expression cassettes as disclosed herein includes a coding sequence of a gene of interest (GOI). In some embodiments, the GOI encodes a polypeptide selected from the group consisting of a therapeutic polypeptide, a prophylactic polypeptide, a diagnostic polypeptide, a neutraceutical polypeptide, an industrial enzyme, and a reporter polypeptide. In some embodiments, the GOI encodes a polypeptide selected from the group consisting of an antibody, an antigen, an immune modulator, and a cytokine. In some particular embodiments, the coding sequence of the GOI is optimized for expression at a level higher than the expression level of a reference coding sequence.

In some embodiments, the nucleic acid molecule includes a modified replicon RNA comprising a modified genome or replicon RNA of a virus belonging to the *Alphavirus* genus of the Togaviridae family. In some embodiments, the modified genome or replicon RNA is of an alphavirus belonging to the VEEV/EEEV group, or the SF group, or the SIN group. In some embodiments, the alphavirus is selected from the group consisting of Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. In some embodiments, the alphavirus is Venezuelan equine encephalitis virus (VEEV).

Some embodiments provide a nucleic acid molecule which includes a modified alphavirus genome or replicon RNA that is operably linked to a heterologous regulatory element. In some embodiments, the heterologous regulatory element includes a promoter sequence. In some embodiments, the promoter sequence includes a T7 promoter sequence. In some embodiments, the heterologous regulatory element includes a transcriptional termination sequence. In some embodiments, the transcriptional termination sequence is or comprises a T7 termination sequence.

In some embodiments, the nucleic acid molecule as disclosed herein includes a modified alphavirus genome or replicon RNA including a modified alphavirus genome or replicon RNA, wherein the nucleic acid molecule exhibits at least 80% sequence identity to the nucleic acid sequence of SEQ ID NO: 1, wherein the modified alphavirus genome or replicon RNA comprises a U→G substitution at position 2 of the 5'-untranslated region (5'-UTR) and is devoid of at least a portion of the sequence encoding viral structural proteins. In some embodiments, the nucleic acid molecule exhibits at least 90%, at least 95%, at least 96%, at least 97%, at least 98%, at least 99%, or 100% sequence identity to the nucleic acid sequence of SEQ ID NO: 1.

In some embodiments, the nucleic acid molecule as disclosed herein includes a modified alphavirus genome or replicon RNA, wherein the modified alphavirus genome or replicon RNA comprises a 5'-UTR exhibiting at least 80% sequence identity to the nucleic acid sequence of at least one of SEQ ID NOS: 2-18 and a U→G substitution at position 2 of the 5'-UTR, and wherein the modified alphavirus genome or replicon RNA is devoid of at least a portion of the sequence encoding viral structural proteins. In some embodiments, the modified alphavirus genome or replicon RNA comprises a 5'-UTR exhibiting at least 90%, at least 95%, at least 96%, at least 97%, at least 98%, at least 99%, or 100% sequence identity to the nucleic acid sequence of at least one of SEQ ID NOS: 2-18. In certain embodiments, the modified alphavirus genome or replicon RNA is devoid of a substantial portion of the nucleic acid sequence encoding viral structural proteins. In certain embodiments, the modified alphavirus genome or replicon RNA comprises no nucleic acid sequence encoding viral structural proteins.

In one aspect, some embodiments disclosed herein relate to a recombinant cell which includes a nucleic acid molecule described herein. In some embodiments, the recombinant cell is a prokaryotic cell or a eukaryotic cell. In some embodiments, the recombinant cell is an animal cell. In some embodiments, the recombinant cell is a vertebrate animal cell or an invertebrate cell. In some embodiments, the recombinant cell is selected from the group consisting of a pulmonary equine artery endothelial cell, an equine dermis cell, a baby hamster kidney (BHK) cell, a rabbit kidney cell, a mouse muscle cell, a mouse connective tissue cell, a human cervix cell, a human epidermoid larynx cell, a Chinese hamster ovary cell (CHO), a human HEK-293 cell, a mouse 3T3 cell, a Vero cell, a Madin-Darby Canine Kidney Epithelial Cell (MDCK), primary chicken fibroblast cell, a HuT78 cell, an A549 lung cell, a HeLa cell, a PER.C6® cell, a WI-38 cell, a MRC-5 cell, a FRhL-2, and a CEM T-cell. Some embodiments disclosed herein provide a cell culture that includes at least one recombinant cell as disclosed herein.

In one aspect, some embodiments provide a method for producing a polypeptide of interest that involves culturing a host cell comprising a nucleic acid molecule which comprises a modified 5-'UTR and is devoid of at least a portion of a nucleic acid sequence encoding viral structural proteins. In some embodiments, the recombinant cell is a vertebrate cell or an invertebrate cell.

In a further aspect, some embodiments provide a method for producing a polypeptide of interest in a subject that involves administering to the subject a nucleic acid molecule which comprises a modified 5-'UTR and is devoid of at least a portion of a nucleic acid sequence encoding viral structural proteins. In some embodiments, the subject is human, horse, pig, primate, mouse, cattle, swine, sheep, rabbit, cat, dog, bird, fish, goat, donkey, hamster, or buffalo.

Implementations of embodiments of the methods according to the present disclosure can include one or more of the following features. In some embodiments, the modified replicon RNA is a modified alphavirus replicon RNA. In some embodiments, the modified alphavirus replicon RNA includes a modified alphavirus genome. In some embodiments, the modified 5'-UTR includes one or more nucleotide substitutions at position 1, 2, 4, or a combination thereof. In some embodiments, at least one of the nucleotide substitutions is a nucleotide substitution at position 2 of the modified 5'-UTR. In some embodiments, the nucleotide substitutions at position 2 of the modified 5'-UTR is a U→G substitution. In certain embodiments, the modified replicon RNA is devoid of a substantial portion of the nucleic acid sequence encoding viral structural proteins. In some embodiments, the modified alphavirus genome or replicon RNA includes no nucleic acid sequence encoding viral structural proteins.

In some embodiments, the nucleic acid molecule as described herein further includes one or more expression cassettes, wherein each of the expression cassettes includes a promoter operably linked to a heterologous nucleic acid sequence. In some embodiments, the nucleic acid molecule includes at least two, at least three, at least four, at least five, or at least six expression cassettes. In some embodiments, the promoter of at least one of the expression cassettes includes a 26S subgenomic promoter. In some particular embodiments, the promoter of at least one of the expression cassettes includes an alphavirus 26S subgenomic promoter. Preferably, the promoter comprises a Venezuelan equine encephalitis (VEEV) 26S subgenomic promoter. In certain embodiments, the heterologous nucleic acid sequence of at least one of the expression cassettes includes a coding sequence of a gene of interest (GOI). The coding sequence of the GOI, in some embodiments, is optimized for expression at a level higher than the expression level of a reference coding sequence. In some embodiments, the promoter operably linked to the heterologous nucleic acid sequence comprises a heterologous promoter sequence. Suitable heterologous promoters include, but are not limited to, regulatory elements from internal ribosome entry site (IRES) derived from encephalomyocarditis viruses (EMCV), Bovine Viral Diarrhea Viruses (BVDV), polioviruses, Foot-and-mouth disease viruses (FMD), enterovirus 71, or hepatitis C viruses.

In some embodiments, the modified replicon RNA includes a modified genome or replicon RNA of a virus belonging to the *Alphavirus* genus of the Togaviridae family. In some embodiments, the modified genome or replicon RNA is of an alphavirus belonging to the VEEV/EEEV group, or the SF group, or the SIN group. In some embodiments, the alphavirus is selected from the group consisting of Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. In some embodiments, the alphavirus is Venezuelan equine encephalitis virus (VEEV).

In some embodiments, the modified alphavirus genome or replicon RNA is operably linked to a heterologous regulatory element. In some embodiments, the heterologous regulatory element includes a promoter sequence. In some embodiments, the promoter sequence includes a T7 promoter sequence. In some embodiments, the heterologous regulatory element comprises a transcriptional termination sequence. In some embodiments, the transcriptional termination sequence is or comprises a T7 termination sequence.

In some embodiments, the nucleic acid molecule includes a modified alphavirus genome or replicon RNA, wherein the modified alphavirus genome or replicon RNA includes a 5'-UTR exhibiting at least 80% sequence identity to the nucleic acid sequence of SEQ ID NO: 1 and a U→G substitution at position 2 of the 5'-UTR, and wherein the modified alphavirus genome or replicon RNA is devoid of at least a portion of the sequence encoding viral structural proteins. In some embodiments, the nucleic acid molecule exhibits at least 90%, at least 95%, at least 96%, at least 97%, at least 98%, at least 99%, or 100% sequence identity to the nucleic acid sequence of SEQ ID NO: 1. In some embodiments, the nucleic acid molecule includes a modified alphavirus genome or replicon RNA, wherein the modified alphavirus genome or replicon RNA includes a 5'-UTR exhibiting at least 80% sequence identity to the nucleic acid sequence of at least one of SEQ ID NOS: 2-18 and a U→G substitution at position 2 of the 5'-UTR, and wherein the modified alphavirus genome or replicon RNA is devoid of at least a portion of the sequence encoding viral structural proteins. In some embodiments, the modified alphavirus genome or replicon RNA includes a 5'-UTR exhibiting at least 90%, at least 95%, at least 96%, at least 97%, at least 98%, at least 99%, or 100% sequence identity to the nucleic acid sequence of at least one of SEQ ID NOS: 2-18.

In a further aspect, some embodiments disclosed herein provide recombinant polypeptides produced by a method in accordance with one or more embodiments disclosed herein.

In one aspect, some embodiments disclosed herein relate to a composition including a recombinant polypeptide as described herein. In some embodiments, the composition is a pharmaceutical composition comprising a pharmaceutical acceptable carrier. In some embodiments, the composition is a prophylactic composition, a neutraceutical composition, a pharmaceutical composition, or a combination thereof.

In a further aspect, some embodiments disclosed herein relate to a composition including a nucleic acid molecule as disclosed herein. In some embodiments, the composition is a pharmaceutical composition comprising a pharmaceutical acceptable carrier. In some embodiments, the composition is a prophylactic composition, a neutraceutical composition, a pharmaceutical composition, or a combination thereof.

In yet a further aspect, some embodiments disclosed herein relate to a composition including a recombinant cell as described herein. In some embodiments, the composition is a pharmaceutical composition comprising a pharmaceutical acceptable carrier. In some embodiments, the composition is a prophylactic composition, a neutraceutical composition, a pharmaceutical composition, or a combination thereof.

The foregoing summary is illustrative only and is not intended to be in any way limiting. In addition to the illustrative embodiments and features described herein, further aspects, embodiments, objects and features of the application will become fully apparent from the drawings and the detailed description and the claims.

BRIEF DESCRIPTION OF THE DRAWINGS

FIG. 1A shows a sequence alignment of the 5' unstranslated regions (5'-UTRs) from representative alphaviruses: Aura virus (AURAV; SEQ ID NO: 2), Chikungunya virus (CHIKV, SEQ ID NO: 3), O'Nyong-Nyong virus (SEQ ID NO: 4, ONNV), Bebaru virus (SEQ ID NO: 5, BEBV), Semliki Forest virus (SEQ ID NO: 6, SFV), Mayaro virus (SEQ ID NO: 7, MAYV), Getah virus (SEQ ID NO: 8, GETV), Sagiyama virus (SEQ ID NO: 9, SAGV), Ndumu virus (SEQ ID NO: 10, NDUV), Middleburg virus (SEQ ID NO: 11, MIDV), Eastern equine encephalitis virus (SEQ ID NO: 12, EEEV), Fort Morgan virus (SEQ ID NO: 13, FMV), Buggy Creek virus (SEQ ID NO: 14, Buggy), Venezuelan equine encephalitis virus (SEQ ID NO: 15, VEEV), Whataroa virus (SEQ ID NO: 16, WHAV), Sindbis virus (SEQ ID NO: 17, SINV), and Bebaru virus (SEQ ID NO: 18, BEBV). The sequence alignment of FIG. 1A was generated using the program MUSCLE 3.6 with default setting. In the sequence alignment shown herein, a dash in an aligned sequence, which is created by the program MUSCLE 3.6 for optimal alignment, represents a gap, i.e., a lack of nucleotide at that position. As discussed in detail below, several conserved nucleotide residues have been identified in this sequence comparison analysis. Asterisks identify identical nucleotide residues among the aligned sequences. FIG. 1B shows a graphical representation of the consensus sequence as a weighted consensus in which the size of the letter designating a given amino acid is proportional to the conservation of the residue in the different sequences used to generate the motif (the size of the letter denotes a residue's relative frequency at that position among the aligned sequences). The size of the character reflects the information content measured in bits.

Figure 2:
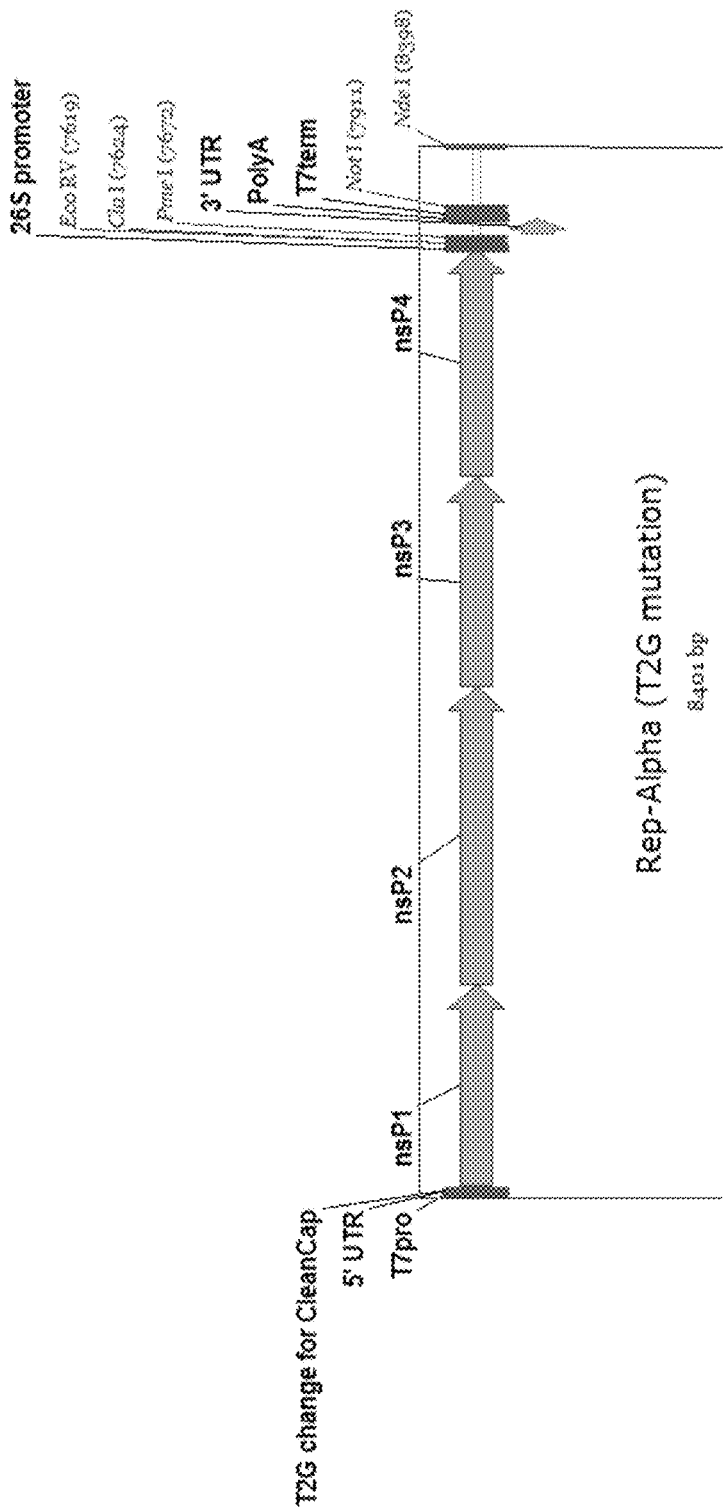
FIG. 2 shows a schematic illustration of the structure of a non-limiting exemplary base monovalent VEEV replicon design, Rep-Alpha, which includes a T7 promoter sequence, a 5'UTR sequence from VEEV having a U2→G substitution as described herein, coding sequence of the nonstructural polypeptides nsp1, nsp2, nsp3, and nsp4 of an alphavirus genome. The base monovalent VEEV replicon Rep-Alpha also contains a 26S subgenomic promoter sequence, 3'UTR sequence, T7 termination sequence, polyadenylation sequence PolyA, and a number of unique restriction sites engineered to facilitate insertion of additional components into the replicon.

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope; the disclosure will be described with additional specificity and detail through use of the accompanying drawings.

DETAILED DESCRIPTION

The present disclosure generally relates to viral expression systems with superior expression potential which are suitable for expressing heterologous molecules such as, for example, vaccines and therapeutic polypeptides, in recombinant cells. For example, some embodiments of the disclosure relate to nucleic acid molecules such as, e.g. expression constructs and vectors, containing a modified replicon RNA which includes a modified 5'-unstranslated region (5'-UTR) and, optionally, at least some of its original viral sequence encoding structural proteins having been deleted. Also included in accordance with some embodiments of the disclosure are viral-based expression vectors including one or more expression cassettes encoding heterologous polypeptide. Accordingly, recombinant cells that are genetically modified to include one or more of the nucleic acid molecules disclosed herein, as well as biomaterials and recombinant products derived from such cells are also within the scope of the application. Further provided in particular aspects of the disclosure are compositions that include one or more of the molecules and/or recombinant cells disclosed herein.

Self-amplifying RNAs (replicons) based on RNA virus (e.g., alphaviruses) can be used as robust expression systems. For example, modifications to the wild-type virus (e.g., alphavirus) 5' untranslated region (UTR) can allow dissection of the key RNA nucleotides that comprise the promoter elements involved in both RNA replication and RNA transcription. Development of enhanced viral (e.g., alphavirus) expression systems by manipulation of the 5' UTR sequence represents an important advancement in replicon platform development. Without being limited by any particular theory, it is believed that a non-limiting advantage of using alphaviruses as viral expression vectors is that they can direct the synthesis of large amounts of heterologous proteins in recombinant host cells. In particular, among other advantages, the alphavirus replicon platform systems disclosed herein, in some embodiments, are capable of expressing up to three times the amount of protein normally expressed from an alphavirus replicon. This improvement is significant given the already naturally high expression levels noted with standard alphavirus replicon systems and that the 5' UTR mutation that imparts this capability was previously considered to be a nearly lethal mutation to alphavirus replication and transcription. For example, polypeptides such as therapeutic single chain antibodies may be most effective if expressed at high levels in vivo. In addition, for producing recombinant antibodies purified from cells in culture (ex vivo), high protein expression from a replicon RNA may increase overall yields of the antibody product. Furthermore, if the protein being expressed is a vaccine antigen, high level expression may induce the most robust immune response in vivo.

In the following detailed description, reference is made to the accompanying drawings, which form a part hereof. In the drawings, similar symbols typically identify similar components, unless context dictates otherwise. The illustrative alternatives described in the detailed description, drawings, and claims are not meant to be limiting. Other alternatives may be used, and other changes may be made, without departing from the spirit or scope of the subject matter presented here. It will be readily understood that the aspects, as generally described herein, and illustrated in the Figures, can be arranged, substituted, combined, and designed in a wide variety of different configurations, all of which are explicitly contemplated and make part of this application.

Unless otherwise defined, all terms of art, notations and other scientific terms or terminology used herein are intended to have the meanings commonly understood by those of skill in the art to which this application pertains. In some cases, terms with commonly understood meanings are defined herein for clarity and/or for ready reference, and the inclusion of such definitions herein should not necessarily be construed to represent a substantial difference over what is generally understood in the art. Many of the techniques and procedures described or referenced herein are well understood and commonly employed using conventional methodology by those of skill in the art.

Some Definitions

The singular form "a", "an", and "the" include plural references unless the context clearly dictates otherwise. For example, the term "a cell" includes one or more cells, comprising mixtures thereof. "A and/or B" is used herein to include all of the following alternatives: "A", "B", "A or B", and "A and B".

The term "about", as used herein, has its ordinary meaning of approximately. If the degree of approximation is not otherwise clear from the context, "about" means either within plus or minus 10% of the provided value, or rounded to the nearest significant figure, in all cases inclusive of the provided value. Where ranges are provided, they are inclusive of the boundary values.

The terms, "cells", "cell cultures", "cell line", "recombinant host cells", "recipient cells" and "host cells" as used herein, include the primary subject cells and any progeny thereof, without regard to the number of transfers. It should be understood that not all progeny are exactly identical to the parental cell (due to deliberate or inadvertent mutations or differences in environment); however, such altered progeny are included in these terms, so long as the progeny retain the same functionality as that of the originally transformed cell.

As used herein, the term "construct" is intended to mean any recombinant nucleic acid molecule such as an expression cassette, plasmid, cosmid, virus, autonomously replicating polynucleotide molecule, phage, or linear or circular, single-stranded or double-stranded, DNA or RNA polynucleotide molecule, derived from any source, capable of genomic integration or autonomous replication, comprising a nucleic acid molecule where one or more nucleic acid sequences has been linked in a functionally operative manner, e.g. operably linked.

The term "gene" is used broadly to refer to any segment of nucleic acid molecule that encodes a protein or that can be transcribed into a functional RNA. Genes may include sequences that are transcribed but are not part of a final, mature, and/or functional RNA transcript, and genes that encode proteins may further comprise sequences that are transcribed but not translated, for example, 5' untranslated regions, 3' untranslated regions, introns, etc. Further, genes may optionally further comprise regulatory sequences required for their expression, and such sequences may be, for example, sequences that are not transcribed or translated. Genes can be obtained from a variety of sources, including cloning from a source of interest or synthesizing from known or predicted sequence information, and may include sequences designed to have desired parameters.

The term "heterologous" when used in reference to a polynucleotide, a gene, or a nucleic acid molecule refers to a polynucleotide, gene, or a nucleic acid molecule that is not derived from the host species. For example, "heterologous gene" or "heterologous nucleic acid sequence" as used herein, refers to a gene or nucleic acid sequence from a different species than the species of the host organism it is introduced into. When referring to a gene regulatory sequence or to an auxiliary nucleic acid sequence used for manipulating expression of a gene sequence (e.g. a 5' untranslated region, 3' untranslated region, poly A addition sequence, etc.) or to a nucleic acid sequence encoding a protein domain or protein localization sequence, "heterologous" means that the regulatory or auxiliary sequence or sequence encoding a protein domain or localization sequence is from a different source than the gene with which the regulatory or auxiliary nucleic acid sequence or nucleic acid sequence encoding a protein domain or localization sequence is juxtaposed in a genome. Thus, a promoter operably linked to a gene to which it is not operably linked to in its natural state (for example, in the genome of a non-genetically engineered organism) is referred to herein as a "heterologous promoter," even though the promoter may be derived from the same species (or, in some cases, the same organism) as the gene to which it is linked. For example, in some embodiments disclosed herein, a coding sequence of a heterologous gene of interest (GOI) is not linked to the EAV replicon sequence in its natural state. In some embodiments, the coding GOI sequence is derived from another organism, such as another virus, bacteria, fungi, human cell (e.g., tumor Ag), parasite (e.g., malaria), etc.)

The terms "nucleic acid molecule" and "polynucleotide" are used interchangeably herein, and refer to both RNA and DNA molecules, including nucleic acid molecules comprising cDNA, genomic DNA, synthetic DNA, and DNA or RNA molecules containing nucleic acid analogs. Nucleic acid molecules can have any three-dimensional structure. A nucleic acid molecule can be double-stranded or single-stranded (e.g., a sense strand or an antisense strand). Non-limiting examples of nucleic acid molecules include genes, gene fragments, exons, introns, messenger RNA (mRNA), transfer RNA, ribosomal RNA, siRNA, micro-RNA, tracrRNAs, crRNAs, guide RNAs, ribozymes, cDNA, recombinant polynucleotides, branched polynucleotides, nucleic acid probes and nucleic acid primers. A nucleic acid molecule may contain unconventional or modified nucleotides. The terms "polynucleotide sequence" and "nucleic acid sequence" as used herein interchangeably refer to the sequence of a polynucleotide molecule. The nomenclature for nucleotide bases as set forth in 37 CFR § 1.822 is used herein.

Nucleic acid molecules can be nucleic acid molecules of any length, including but not limited to, nucleic acid molecules that are between about 3 Kb and about 50 Kb, for example between about 3 Kb and about 40 Kb, between about 3 Kb and about 40 Kb, between about 3 Kb and about 30 Kb, between about 3 Kb and about 20 Kb, between 5 Kb and about 40 Kb, between about 5 Kb and about 40 Kb, between about 5 Kb and about 30 Kb, between about 5 Kb and about 20 Kb, or between about 10 Kb and about 50 Kb, for example between about 15 Kb to 30 Kb, between about 20 Kb and about 50 Kb, between about 20 Kb and about 40 Kb, about 5 Kb and about 25 Kb, or about 30 Kb and about 50 Kb. The nucleic acid molecules can also be, for example, more than 50 kb.

The polynucleotides of the present disclosure can be "biologically active" with respect to either a structural attribute, such as the capacity of a nucleic acid to hybridize to another nucleic acid, or the ability of a polynucleotide sequence to be recognized and bound by a transcription factor and/or a nucleic acid polymerase.

The term "recombinant" or "engineered" nucleic acid molecule as used herein, refers to a nucleic acid molecule that has been altered through human intervention. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination)) of nucleic acid molecules; 2) includes conjoined nucleotide sequences that are not conjoined in nature, 3) has been engineered using molecular cloning techniques such that it lacks one or more nucleotides with respect to the naturally occurring nucleic acid molecule sequence, and/or 4) has been manipulated using molecular cloning techniques such that it has one or more sequence changes or rearrangements with respect to the naturally occurring nucleic acid sequence. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

As used herein, a "substantial portion" of a nucleic acid sequence encoding a viral structural polypeptide can comprise enough of the nucleic acid sequence encoding the viral structural polypeptide to afford putative identification of that polypeptide, either by manual evaluation of the sequence by one skilled in the art, or by computer-automated sequence comparison and identification using algorithms such as BLAST (see, for example, in "Basic Local Alignment Search Tool"; Altschul S F et al., J. Mol. Biol. 215:403-410, 1993). In general, one of skill in the art will recognize that a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 15-30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 10-15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The present disclosure provides nucleic acid molecules which are devoid of partial or complete nucleic acid sequences encoding one or more viral structural polypeptides. The skilled artisan, having the benefit of the sequences as disclosed herein, can readily use all or a substantial portion of the disclosed sequences for purposes known to those skilled in this art. Accordingly, the present application comprises the complete sequences as disclosed herein, e.g., those set forth in the accompanying Sequence Listing, as well as substantial portions of those sequences as defined above.

As will be understood by one having ordinary skill in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

The discussion of the general methods provided herein is intended for illustrative purposes only. Other alternative methods and alternatives will be apparent to those of skill in the art upon review of this application, and are to be included within the spirit and purview of this application.

Alphaviruses

*Alphavirus* is a genus of genetically, structurally, and serologically related viruses of the group IV Togaviridae family which includes at least 30 members, each having single stranded RNA genomes of positive polarity enclosed in a nucleocapsid surrounded by an envelope containing viral spike proteins. Currently, the alphavirus genus comprises among others the Sindbis virus (SIN), the Semliki Forest virus (SFV), the Ross River virus (RRV), Venezuelan equine encephalitis virus (VEEV), and Eastern equine encephalitis virus (EEEV), which are all closely related and are able to infect various vertebrates such as mammalians, rodents, fish, avian species, and larger mammals such as humans and horses as well as invertebrates such as insects. Transmission between species and individuals occurs mainly via mosquitoes making the alphaviruses a contributor to the collection of Arboviruses- or Arthropod-Borne Viruses. In particular, the Sindbis and the Semliki Forest viruses have been widely studied and the life cycle, mode of replication, etc., of these viruses are well characterized. In particular, alphaviruses have been shown to replicate very efficiently in animal cells which makes them valuable as vectors for production of protein and nucleic acids in such cells.

*Alphavirus* particles are enveloped, have a 70 nm diameter, tend to be spherical (although slightly pleomorphic), and have an approximately 40 nm isometric nucleocapsid. FIG. 8 depicts a typical alphavirus genomic structure and genome expression (adapted from Strauss et al., Microbiological Reviews, pp. 491-562, September 1994). *Alphavirus* genome is single-stranded RNA of positive polarity of approximately 11-12 kb in length, comprising a 5' cap, a 3' poly-A tail, and two open reading frames with a first frame encoding the nonstructural proteins with enzymatic function and a second frame encoding the viral structural proteins (e.g., the capsid protein C, E1 glycoprotein, E2 glycoprotein, E3 protein and 6K protein).

The 5' two-thirds of the alphavirus genome encodes a number of nonstructural proteins necessary for transcription and replication of viral RNA. These proteins are translated directly from the RNA and together with cellular proteins form the RNA-dependent RNA polymerase essential for viral genome replication and transcription of subgenomic RNA. Four nonstructural proteins (nsP1-4) are produced as a single polyprotein constitute the virus' replication machinery. The processing of the polyprotein occurs in a highly regulated manner, with cleavage at the P2/3 junction influencing RNA template use during genome replication. This site is located at the base of a narrow cleft and is not readily accessible. Once cleaved, nsP3 creates a ring structure that encircles nsP2. These two proteins have an extensive interface. Mutations in nsP2 that produce noncytopathic viruses or a temperature sensitive phenotypes cluster at the P2/P3 interface region. P3 mutations opposite the location of the nsP2 noncytopathic mutations prevent efficient cleavage of P2/3. This in turn can affect RNA infectivity altering viral RNA production levels.

The 3' one-third of the genome comprises subgenomic RNA which serves as a template for translation of all the structural proteins required for forming viral particles: the core nucleocapsid protein C, and the envelope proteins P62 and E1 that associate as a heterodimer. The viral membrane-anchored surface glycoproteins are responsible for receptor recognition and entry into target cells through membrane fusion. The subgenomic RNA is transcribed from the p26S subgenomic promoter present at the 3' end of the RNA sequence encoding the nsp4 protein. The proteolytic maturation of P62 into E2 and E3 causes a change in the viral surface. Together the E1, E2, and sometimes E3, glycoprotein "spikes" form an E1/E2 dimer or an E1/E2/E3 trimer, where E2 extends from the center to the vertices, E1 fills the space between the vertices, and E3, if present, is at the distal end of the spike. Upon exposure of the virus to the acidity of the endosome, E1 dissociates from E2 to form an E1 homotrimer, which is necessary for the fusion step to drive the cellular and viral membranes together. The alphaviral glycoprotein E1 is a class II viral fusion protein, which is structurally different from the class I fusion proteins found in influenza virus and HIV. The E2 glycoprotein functions to interact with the nucleocapsid through its cytoplasmic domain, while its ectodomain is responsible for binding a cellular receptor. Most alphaviruses lose the peripheral protein E3, while in Semliki viruses it remains associated with the viral surface.

*Alphavirus* replication has been reported to take place in the cytoplasm of the cell. In the first step of the infectious cycle, the 5' end of the genomic RNA is translated into a polyprotein (nsP1-4) with RNA polymerase activity that produces a negative strand complementary to the genomic RNA. In a second step, the negative strand is used as a template for the production of two RNAs, respectively: (1) a positive genomic RNA corresponding to the genome of the secondary viruses producing, by translation, other nsp proteins and acting as a genome for the virus; and (2) subgenomic RNA encoding the structural proteins of the virus forming the infectious particles. The positive genomic RNA/subgenomic RNA ratio is regulated by proteolytic autocleavage of the polyprotein to nsp 1, nsp 2, nsp 3 and nsp 4. In practice, the viral gene expression takes place in two phases. In a first phase, there is main synthesis of positive genomic strands and of negative strands. During the second phase, the synthesis of subgenomic RNA is virtually exclusive, thus resulting in the production of large amount of structural protein.

Previous detailed analyses of the 5'-unstranslated regions (5'-UTR) of alphaviruses have revealed the absolute importance of the extreme 5' nucleotides to support RNA replication and transcription. In particular, as illustrated in FIG. 1, the conservation of an AU dinucleotide at nucleotide positions 1 and 2, respectively, of the 5' UTR sequence is noted among all alphaviruses suggesting the importance of these nucleotides. As used herein, "A1" refers to the conserved A nucleotide at nucleotide position 1 of the 5'-UTR (e.g., an alphavirus 5'-UTR), and "U2" refers to the conserved U nucleotide at nucleotide position 2 of the 5'-UTR (e.g., an alphavirus 5'-UTR). Further, for Venezuelan equine encephalitis virus (VEEV), detailed analysis of the 5' most three nucleotides as well as the stem loop region found immediately following this sequence has been conducted. In particular, the importance of maintaining the U residue at position 2 of the 5' UTR has been determined previously (Kulasegaran-Shylini et al., J. Virol. 83:17 p 8327-8339, 2009a; and Kulasegaran-Shylini et al. J. Virol. 83:17 p 8327-8339, 2009b). Specifically, in vitro transcribed RNA from a full length infectious clone designated (G2)VEE/SINV containing a single U2→G change in the 5' UTR demonstrated a loss of nearly three logs of infectivity compared to in vitro transcribed RNA from a wild type VEE/SINV infectious clone. This report strongly suggests that the U at position 2 is critical to RNA replication and cannot be replaced with a G. However, as described herein in details, a VEEV replicon with a U2→G change in the 5' UTR is, surprisingly and in direct contradiction to this previous report, not only completely capable of robust replication but result in three times the expression potential of a VEEV replicon as compared to a wild-type 5' UTR containing the U residue at position 2.

The extreme 5' and 3' sequences of most RNA viruses are highly constrained and little if any variation is tolerated; most modifications result in highly crippled or lethal outcomes for RNA replication. Kulasegaran-Shylini et al. completed an in-depth analysis of the 5' nucleotide sequences critical to RNA replication for a chimeric VEEV/SINV infectious clone, which is representative of all alphaviruses (Kulasegaran-Shylini et al. 2009a, supra). This report built on analysis carried out over the course of 25 years by many researchers that clearly supports the restriction in RNA sequence variation that can occur at the 5' end of any particular alphavirus. The Kulasegaran-Shylini et al. 2009b paper (J. Virol. 83:17 p 8327-8339, 2009) specifically states/shows that changing nucleotide 2 in the 5' UTR from a U residue to a G residue (U2→G) significantly reduces the viability of that infectious clone RNA. That is, that specific change in the 5'-UTR reduced biologic activity of the infectious clone RNA by nearly 3 orders of magnitude. As disclosed herein, the change in the 5'-UTR (e.g., a U2→G change) incorporated into a VEEV (strain TC-83) replicon RNA not only does not cripple the replication of the replicon but can actually increase the biological activity of the replicon. For example, the replicon comprising the U2→G substitution can, in some embodiments, leads to the expression of a protein of interest as much as three times more than a wild type replicon expressing the same protein. This result is surprising and the increased biologic activity of the replicon carrying the U2→G change could not have been predicted. This modified replicon has the potential to be a superior RNA expression platform to support both vaccine and therapeutic applications.

Conservation of the 5' most 2 nucleotides has been observed across all of the genomic RNA of alphavirus subtypes. The conserved AU dinucleotide (A1 and U2) has also been shown to be critically required for RNA replication (Kulasegaran-Shylini et al. 2009a and 2009b, supra). The demonstration that an alphavirus replicon RNA carrying an AG dinucleotide at the extreme 5' end is not only completely functional but demonstrates enhanced biologic activity is surprising and is completely contrary to the dogma in the field.

As disclosed herein, monogenic or multigenic alphavirus expression systems can be generated by using a modified replicon RNA having expression/translation enhancing activity such as, for example, a replicon RNA containing a modified 5'-UTR. In some embodiments, the viral (e.g., alphavirus) expression systems as described herein are further devoid of a part or the entire coding region for one or more viral structural proteins. For example, the alphavirus expression system may be devoid of a portion of or the entire coding sequence for one or more of the viral capsid protein C, E1 glycoprotein, E2 glycoprotein, E3 protein and 6K protein. In some embodiments, modification of nucleotide at position 2 in a cDNA copy of the Venezuelan equine encephalitis virus (VEEV) 5' UTR sequence from a thymine (T) nucleotide to a guanine (G) nucleotide (T2→G mutation), in the context of a replicon RNA, bestows the replicon with significantly higher protein expression potential compared to a VEEV replicon with a wild-type 5' UTR sequence.

In some embodiments, the level of expression and/or translation enhancement activity of the modified replicon RNAs as disclosed herein is of at least 1.1, 1.2, 1.3, 1.4, 1.5, 1.6, 1.7, 1.8, 1.9, 2 (2-fold), 3, 4, 5, 6, 7, 8, or more times, relative to the expression level detected from a corresponding unmodified replicon, e.g. replicon with a wild-type 5' UTR. Without being limited by any particular theory, enhanced translation can be due to an enhancement of transcription which results in an increased level of transcripts being available for translation and/or can be independent of transcription and be due to for example enhanced ribosome binding. The level of enhancement activity can be measured by any convenient methods and techniques known in the art including, but are not limited to, transcript level, amount of protein, protein activity, etc. (see e.g., Examples 1, 3-5 below).

Nucleic Acid Molecules

In one aspect, novel nucleic acid molecules which include a modified replicon RNA are disclosed herein. For example, a modified replicon RNA can comprise mutation(s), deletion(s), substitution(s), and/or insertion(s) in one or more of the original genomic regions (e.g., open reading frames (ORFs) and/or non-coding regions (e.g., promoter sequences)) of the parent replicon RNA. In some embodiments, the modified replicon RNA includes a modified 5'-untranslated region (5'-UTR). In some embodiments, the modified 5'-UTR includes one or more nucleotide substitutions at position 1, 2, 4, or a combination thereof. In some embodiments, at least one of the nucleotide substitutions is a nucleotide substitution at position 1 of the modified 5'-UTR. In some embodiments, at least one of the nucleotide substitutions is a nucleotide substitution at position 2 of the modified 5'-UTR. In some embodiments, at least one of the nucleotide substitutions is a nucleotide substitution at position 4 of the modified 5'-UTR. In some embodiments, the nucleotide substitutions at position 2 of the modified 5'-UTR is a U→G substitution. In some embodiments, the nucleotide substitution at position 2 of the modified 5'-UTR is a U→A substitution. In some embodiments, the nucleotide substitution at position 2 of the modified 5'-UTR is a U→C substitution.

As used herein, the terms "replicon RNA" refers to RNA which contains all of the genetic information required for directing its own amplification or self-replication within a permissive cell. To direct its own replication, the RNA molecule 1) encodes polymerase, replicase, or other proteins which may interact with viral or host cell-derived proteins, nucleic acids or ribonucleoproteins to catalyze the RNA amplification process; and 2) contain cis-acting RNA sequences required for replication and transcription of the subgenomic replicon-encoded RNA. These sequences may be bound during the process of replication to its self-encoded proteins, or non-self-encoded cell-derived proteins, nucleic acids or ribonucleoproteins, or complexes between any of these components. For the purpose of the present disclosure, an alphavirus-derived replicon RNA molecule typically contains the following ordered elements: 5' viral or defective-interfering RNA sequence(s) required in cis for replication, sequences coding for biologically active alphavirus nonstructural proteins (e.g., nsP1, nsP2, nsP3, and nsP4), promoter for the subgenomic RNA, 3' viral sequences required in cis for replication, and a polyadenylate tract. Further, the term replicon RNA generally refers to a molecule of positive polarity, or "message" sense, and the replicon RNA may be of length different from that of any known, naturally-occurring alphavirus. In some embodiments of the present disclosure, the replicon RNA does not contain the sequences of at least one of structural viral protein; sequences encoding structural genes can be substituted with heterologous sequences. In those instances, where the replicon RNA is to be packaged into a recombinant alphavirus particle, it must contain one or more sequences, so-called packaging signals, which serve to initiate interactions with alphavirus structural proteins that lead to particle formation.

As used herein, "subgenomic RNA" refers to a RNA molecule of a length or size which is smaller than the genomic RNA from which it was derived. The alphavirus subgenomic RNA should be transcribed from an internal promoter, whose sequences reside within the genomic RNA or its complement. Transcription of an alphavirus subgenomic RNA may be mediated by viral-encoded polymerase(s) associated with host cell-encoded proteins, ribonucleoprotein(s), or a combination thereof. In some embodiments of the present disclosure, the subgenomic RNA is produced from a modified replicon RNA as disclosed herein and encodes or expresses one or more gene of interest (GOI). Instead of the native subgenomic promoter, the subgenomic RNA can be placed under control of internal ribosome entry site (IRES) derived from encephalomyocarditis viruses (EMCV), Bovine Viral Diarrhea Viruses (BVDV), polioviruses, Foot-and-mouth disease viruses (FMD), enterovirus 71, or hepatitis C viruses.

Accordingly, in some embodiments, a part or the entire coding sequence for one or more viral structural proteins are absent and/or modified in the nucleic acid molecules disclosed herein. Thus, in some particular embodiments, the modified replicon RNA as disclosed herein includes a modified 5-'UTR and is devoid of at least a portion of a nucleic acid sequence encoding one or more viral structural proteins, for example, devoid of the first one, two, three, four, five, six, seven, eight, nine, ten, or more nucleotides of the nucleic acid sequence encoding the viral structural proteins. In some embodiments, the modified alphavirus genome or replicon RNA can be devoid of about 10%, 20%, 30%, 40%, 50%, 60%, 70%, 80%, 90%, 95%, or more of the sequence encoding one or more of the structural polypeptides E1, E2, E3, 6K, and capsid protein C. In some embodiments, the modified alphavirus genome or replicon RNA is devoid of a substantial portion of or the entire sequence encoding one of or more of the structural polypeptides E1, E2, E3, 6K, and capsid protein C. As used herein, a "substantial portion" of a nucleic acid sequence encoding a viral structural protein comprises enough of the nucleic acid sequence encoding the viral structural protein to afford putative identification of that protein, either by manual evaluation of the sequence by one skilled in the art, or by computer-automated sequence comparison and identification using algorithms such as BLAST (see, for example, Altschul S F et al. 1993, supra). In some embodiments, the modified alphavirus genome or replicon RNA is devoid of the entire sequence encoding one or more of the structural polypeptides E1, E2, E3, 6K, and capsid protein C.

In some particular embodiments of the application, the nucleic acid molecule as disclosed herein includes a modified alphavirus genome or replicon RNA including a modified alphavirus genome or replicon RNA, wherein the nucleic acid molecule exhibits at least 80% sequence identity to the nucleic acid sequence of SEQ ID NO: 1, wherein the modified alphavirus genome or replicon RNA comprises a U→G substitution at position 2 of the 5'-untranslated region (5'-UTR) and is devoid of at least a portion of the sequence encoding viral structural proteins. In some embodiments, the nucleic acid molecule exhibits at least 90%, at least 95%, at least 96%, at least 97%, at least 98%, at least 99%, or 100% sequence identity to the nucleic acid sequence of SEQ ID NO: 1. In some embodiments, the nucleic acid molecule exhibits 100% sequence identity to the nucleic acid sequence of SEQ ID NO: 1.

In some embodiments, the nucleic acid molecule as disclosed herein includes a modified alphavirus genome or replicon RNA, wherein the modified alphavirus genome or replicon RNA comprises a 5'-UTR exhibiting at least 80% sequence identity to the nucleic acid sequence of at least one 5'-UTR disclosed herein and a U→G substitution at position 2 of the 5'-UTR, and wherein the modified alphavirus genome or replicon RNA is devoid of at least a portion of the sequence encoding viral structural proteins. In some embodiments, the modified alphavirus genome or replicon RNA comprises a 5'-UTR exhibiting at least 80% sequence identity to at least one of the sequences set forth in SEQ ID NOS: 2-18. In some embodiments, the modified alphavirus genome or replicon RNA comprises a 5'-UTR exhibiting at least 90%, at least 95%, at least 96%, at least 97%, at least 98%, at least 99%, or 100% sequence identity to at least one of the sequences set forth in SEQ ID NOS: 2-18. In some embodiments, the modified alphavirus genome or replicon RNA comprises a 5'-UTR exhibiting 100% sequence identity to at least one of the sequences set forth in SEQ ID NOS: 2-18 of the Sequence Listing.

Nucleic acid molecules having a high degree of sequence identity (e.g., at least 85%, at least 90%, at least 95%, at least 96%, at least 97%, at least 98%, at least 99%, or 100% to the nucleic acid sequence of a 5'UTR disclosed herein can be identified and/or isolated by using the sequences identified herein (e.g., SEQ ID NOS: 1-18) or any others alphavirus 5'UTR as they are known in the art, for example, the sequences having GenBank/NCBI accession numbers J02363, NC_001547, U38305, L04653, NC_001449, U38304, X04129, NC_003215, and the TR339 genomic sequence (Klimstra et al., J. Virol. 72:7357, 1988; McKnight et al., J. Virol. 70:1981, 1996), by genome sequence analysis, hybridization, and/or PCR with degenerate primers or gene-specific primers from sequences identified in the respective alphavirus genome. As used herein "sequence identity" refers to the extent to which two optimally aligned polynucleotide are invariant throughout a window of alignment of components, e.g., nucleotides. An "identity fraction" for aligned segments of a test sequence and a reference sequence is the number of identical components which are shared by the two aligned sequences divided by the total number of components in reference sequence segment, e.g., the entire reference sequence or a smaller defined part of the reference sequence.

Some embodiments disclosed herein relate to nucleic acid molecules comprising a modified replicon RNA, wherein the modified replicon RNA comprises a modified alphavirus base sequence such as, e.g. a 5'UTR, having translation enhancing activity. Such modified replicon RNAs can be used to achieve enhanced levels of expression of a heterologous nucleic acid sequence (e.g., DNA or cDNA) coding for a desired product. In some embodiments, the modified replicon RNAs are used to achieve enhanced levels of expression of a heterologous nucleic acid sequence (e.g., DNA or cDNA) coding for a desired product after introduction of the modified replicons in a cell which can be, for example, a cell in cell culture or can be a cell in a living body.

In addition, in some embodiments, the nucleic acid molecules can include a modified alphavirus genome or replicon RNA containing one or more attenuating mutations so as to increase the safety of virus manipulation and/or administration. The phrase "attenuating mutation" as used herein means a nucleotide mutation or an amino acid encoded in view of such mutation which result in a decreased probability of causing disease in its host (i.e., a loss of virulence), in accordance with standard terminology in the art, whether the mutation be a substitution mutation or an in-frame deletion or insertion mutation. Attenuating mutations may be in the coding or non-coding regions (e.g. 5'UTR) of the alphavirus genome. As known by those skilled in the art, the phrase "attenuating mutation" excludes mutations or combinations of mutations which would be lethal to the virus. Further, those skilled in the art will appreciate that some attenuating mutations may be lethal in the absence of a second-site suppressor mutation(s).

The molecular techniques and methods by which these new nucleic acid molecules were constructed and characterized are described more fully in the Examples herein of the present application. In the Examples section, the Venezuelan equine encephalitis virus (VEEV) has been used to illustrate the compositions and methods disclosed herein.

In some embodiments, the nucleic acid molecules are recombinant nucleic acid molecules. As used herein, the term recombinant means any molecule (e.g. DNA, RNA, polypeptide), that is, or results, however indirect, from human manipulation. As non-limiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector. As non-limiting examples, a recombinant nucleic acid molecule: 1) has been synthesized or modified in vitro, for example, using chemical or enzymatic techniques (for example, by use of chemical nucleic acid synthesis, or by use of enzymes for the replication, polymerization, exonucleolytic digestion, endonucleolytic digestion, ligation, reverse transcription, transcription, base modification (including, e.g., methylation), or recombination (including homologous and site-specific recombination) of nucleic acid molecules; 2) includes conjoined nucleotide sequences that are not conjoined in nature; 3) has been engineered using molecular cloning techniques such that it lacks one or more nucleotides with respect to the naturally occurring nucleotide sequence; and/or 4) has been manipulated using molecular cloning techniques such that it has one or more sequence changes or rearrangements with respect to the naturally occurring nucleotide sequence.

In some embodiments, the nucleic acid molecules disclosed herein are produced using recombinant DNA technology (e.g., polymerase chain reaction (PCR) amplification, cloning, etc.) or chemical synthesis. Nucleic acid molecules as disclosed herein include natural nucleic acid molecules and homologs thereof, including, but not limited to, natural allelic variants and modified nucleic acid molecules in which one or more nucleotide residues have been inserted, deleted, and/or substituted, in such a manner that such modifications provide the desired property in effecting a biological activity as described herein.

A nucleic acid molecule, including a variant of a naturally-occurring nucleic acid sequence, can be produced using a number of methods known to those skilled in the art (see, for example, Sambrook et al., In: Molecular Cloning, A Laboratory Manual, 2nd Edition, Cold Spring Harbor Press, Cold Spring Harbor, N.Y. (1989)). The sequence of a nucleic acid molecule can be modified with respect to a naturally-occurring sequence from which it is derived using a variety of techniques including, but not limited to, classic mutagenesis techniques and recombinant DNA techniques, such as but not limited to site-directed mutagenesis, chemical treatment of a nucleic acid molecule to induce mutations, restriction enzyme cleavage of a nucleic acid fragment, ligation of nucleic acid fragments, PCR amplification and/or mutagenesis of selected regions of a nucleic acid sequence, recombinational cloning, and chemical synthesis, including chemical synthesis of oligonucleotide mixtures and ligation of mixture groups to "build" a mixture of nucleic acid molecules, and combinations thereof. Nucleic acid molecule homologs can be selected from a mixture of modified nucleic acid molecules by screening for the function of the protein or the replicon encoded by the nucleic acid molecule and/or by hybridization with a wild-type gene or fragment thereof, or by PCR using primers having homology to a target or wild-type nucleic acid molecule or sequence.

In various embodiments disclosed herein, the nucleic acid molecule disclosed herein can include one or more of the following feature. In some embodiments, the modified replicon RNA is a modified alphavirus replicon RNA. In some embodiments, the modified alphavirus replicon RNA includes a modified alphavirus genome. In some embodiments, the modified 5'-UTR includes one or more nucleotide substitutions at position 1, 2, 4, or a combination thereof. In certain embodiments, at least one of the nucleotide substitutions is a nucleotide substitution at position 2 of the modified 5'-UTR. In some particular embodiments, the nucleotide substitutions at position 2 of the modified 5'-UTR is a U→G substitution.

In some embodiments disclosed herein, the modified alphavirus genome or replicon RNA is operably linked to a heterologous regulatory element. As used herein, "regulatory element", "regulatory sequence", or "regulatory element sequence" refers to a nucleotide sequence located upstream (5'), within, or downstream (3') of a coding sequence such as, for example, a polypeptide-encoding sequence or a functional RNA-encoding sequence. Transcription of the coding sequence and/or translation of an RNA molecule resulting from transcription of the coding sequence are typically affected by the presence or absence of the regulatory element. These regulatory elements may comprise promoters, cis-elements, enhancers, terminators, or introns. One of skill in the art will appreciate that the regulatory elements described herein may be present in a chimeric or hybrid regulatory expression element. In some embodiments, the heterologous regulatory element is, or comprises, a promoter sequence. The heterologous promoter sequence can be any heterologous promoter sequence, for example, a SP6 promoter, a T3 promoter, or a T7 promoter, or a combination thereof. In some particular embodiments, the promoter sequence includes a T7 promoter sequence.

Further, in some embodiments, the modified alphavirus genome or replicon RNA can include one or more heterologous transcriptional termination signal sequences. The term "transcriptional termination signal", "terminator" or "terminator sequence" or "transcription terminator", as used interchangeably herein, refers to a regulatory section of genetic sequence that causes RNA polymerase to cease transcription. The heterologous transcriptional termination signal sequences can generally be any heterologous transcriptional termination signal sequences, and for example, SP6 termination signal sequence, a T3 termination signal sequence, a T7 termination signal sequence, or a variant thereof. Accordingly, the nucleic acid molecules according to some embodiments of the disclosure can include at least one of the one or more heterologous transcriptional termination signal sequences selected from the group consisting of a SP6 termination signal sequence, a T3 termination signal sequence, a T7 termination signal sequence, or a variant thereof. In some particular embodiments, the transcriptional termination sequence includes a T7 termination signal sequence.

In some embodiments, the nucleic acid molecules disclosed herein can include one or more expression cassettes. In principle, the nucleic acid molecules disclosed herein can generally include any number of expression cassettes. In some particular embodiments, the nucleic acid molecules disclosed herein can include at least two, at least three, at least four, at least five, or at least six expression cassettes. As used herein, the term "expression cassette" refers to a construct of genetic material that contains coding sequences and enough regulatory information to direct proper transcription and/or translation of the coding sequences in a recipient cell, in vivo and/or ex vivo. The expression cassette may be inserted into a vector for targeting to a desired host cell and/or into a subject. Further, the term expression cassette may be used interchangeably with the term "expression construct". In some embodiments, the term "expression cassette" refers to a nucleic acid construct that includes a gene encoding a protein or functional RNA operably linked to regulatory elements such as, for example, a promoter and/or a termination signal, and optionally, any or a combination of other nucleic acid sequences that affect the transcription or translation of the gene.

The term "operably linked", as used herein, denotes a functional linkage between two or more sequences. For example, an operably linkage between a polynucleotide of interest and a regulatory sequence (for example, a promoter) is functional link that allows for expression of the polynucleotide of interest. In this sense, the term "operably linked" refers to the positioning of a regulatory region and a coding sequence to be transcribed so that the regulatory region is effective for regulating transcription or translation of the coding sequence of interest. In some embodiments disclosed herein, the term "operably linked" denotes a configuration in which a regulatory sequence is placed at an appropriate position relative to a sequence that encodes a polypeptide or functional RNA such that the control sequence directs or regulates the expression or cellular localization of the mRNA encoding the polypeptide, the polypeptide, and/or the functional RNA. Thus, a promoter is in operable linkage with a nucleic acid sequence if it can mediate transcription of the nucleic acid sequence. Operably linked elements may be contiguous or non-contiguous.

The basic techniques for operably linking two or more sequences of DNA together are familiar to the skilled worker, and such methods have been described in a number of texts for standard molecular biological manipulation (see, for example, Maniatis et al., "Molecular Cloning: A Laboratory Manual" 2nd ed. Cold Spring Harbor Laboratory Press, Cold Spring Harbor, N.Y.; and Gibson et al., Nature Methods 6:343-45, 2009).

Accordingly, the nucleic acid molecules as provided herein can find use, for example, as an expression vector that, when including a regulatory element operably linked to a heterologous nucleic acid sequence, can affect expression of the heterologous nucleic acid sequence. In some embodiments, the heterologous nucleotide sequence includes a coding sequence of a gene of interest (GOI). In some embodiments, the coding sequence of the GOI is optimized for expression at a level higher than the expression level of a reference coding sequence. In some embodiments, the reference coding sequence is a sequence that has not been optimized. In some embodiments, the optimization of the GOI coding sequence can include sequence optimization. With respect to sequence-optimization of nucleotide sequences, degeneracy of the genetic code provides the possibility to substitute at least one base of the protein encoding sequence of a gene with a different base without causing the amino acid sequence of the polypeptide produced from the gene to be changed. Hence, the nucleic acid molecules of the present application may also have any base sequence that has been changed from any polynucleotide sequence disclosed herein by substitution in accordance with degeneracy of the genetic code. References describing codon usage are readily publicly available. In some embodiments, polynucleotide sequence variants can be produced for a variety of reasons, e.g., to optimize expression for a particular host (e.g., changing codon usage in the alphavirus mRNA to those preferred by other organisms such as human, hamster, mice, or monkey).

The polypeptide encoded by a GOI can generally be any polypeptide, and can be, for example a therapeutic polypeptide, a prophylactic polypeptide, a diagnostic polypeptide, a neutraceutical polypeptide, or an industrial enzyme. In some embodiments, the GOI encodes a polypeptide selected from the group consisting of an antibody, an antigen, an immune modulator, and a cytokine.

In some embodiments, the coding sequence of the GOI is optimized for a desired property. In some embodiments, the coding sequence of the GOI is optimized for expression at a level higher than the expression level of a reference coding sequence.

In some embodiments, the modified genome or replicon RNA disclosed herein is a genome or replicon RNA of an alphavirus, such as a genome or replicon RNA of a viral species belonging to the *Alphavirus* genus of the Togaviridae family. In some embodiments, the modified genome or replicon RNA is of an alphavirus belonging to the VEEV/EEEV group, or the SF group, or the SIN group (for review, see, e.g. Strauss and Strauss. Microbiol. Rev. 58:3 p 492-562, 1994). Non-limiting examples of SF group alphaviruses include Semliki Forest virus, O'Nyong-Nyong virus, Ross River virus, Middelburg virus, Chikungunya virus, Barmah Forest virus, Getah virus, Mayaro virus, Sagiyama virus, Bebaru virus, and Una virus. Non-limiting examples of SIN group alphaviruses include Sindbis virus, Girdwood S.A. virus, South African Arbovirus No. 86, Ockelbo virus, Aura virus, Babanki virus, Whataroa virus, and Kyzylagach virus. Non-limiting examples of VEEV/EEEV group alphaviruses include Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), and Una virus (UNAV).

Non-limiting examples of alphavirus species includes Eastern equine encephalitis virus (EEEV), Venezuelan equine encephalitis virus (VEEV), Everglades virus (EVEV), Mucambo virus (MUCV), Pixuna virus (PIXV), Middleburg virus (MIDV), Chikungunya virus (CHIKV), O'Nyong-Nyong virus (ONNV), Ross River virus (RRV), Barmah Forest virus (BF), Getah virus (GET), Sagiyama virus (SAGV), Bebaru virus (BEBV), Mayaro virus (MAYV), Una virus (UNAV), Sindbis virus (SINV), Aura virus (AURAV), Whataroa virus (WHAV), Babanki virus (BABV), Kyzylagach virus (KYZV), Western equine encephalitis virus (WEEV), Highland J virus (HJV), Fort Morgan virus (FMV), Ndumu (NDUV), and Buggy Creek virus. Virulent and avirulent alphavirus strains are both suitable. In some particular embodiments, the modified genome or replicon RNA is of a Sindbis virus (SIN), a Semliki Forest virus (SFV), a Ross River virus (RRV), a Venezuelan equine encephalitis virus (VEEV), or an Eastern equine encephalitis virus (EEEV). In some embodiments, the modified genome or replicon RNA is of a Venezuelan equine encephalitis virus (VEEV).

Recombinant Cells

In one aspect, some embodiments disclosed herein relate to a method of transforming a cell that includes introducing into a host cell, such as an animal cell, a nucleic acid molecule as provided herein, and selecting or screening for a transformed cell. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. In some embodiments, the nucleic acid molecule is introduced into a host cell by an electroporation procedure or a biolistic procedure.

In a related aspect, some embodiments relate to recombinant host cells, for example, recombinant animal cells that include a nucleic acid molecule described herein. The nucleic acid molecule can be stably integrated in the host genome, or can be episomally replicating, or present in the recombinant host cell as a mini-circle expression vector for a stable or transient expression. Accordingly, in some embodiments disclosed herein, the nucleic acid molecule is maintained and replicated in the recombinant host cell as an episomal unit. In some embodiments, the nucleic acid molecule is stably integrated into the genome of the recombinant cell. Stable integration can be completed using classical random genomic recombination techniques or with more precise genome editing techniques such as using guide RNA directed CRISPR/Cas9, or DNA-guided endonuclease genome editing NgAgo (*Natronobacterium gregoryi* Argonaute), or TALEN genome editing (transcription activator-like effector nucleases). In some embodiments, the nucleic acid molecule present in the recombinant host cell as a mini-circle expression vector for a stable or transient expression.

In some embodiments, host cells can be genetically engineered (e.g. transduced or transformed or transfected) with, for example, a vector construct of the present application that can be, for example, a vector for homologous recombination that includes nucleic acid sequences homologous to a portion of the genome of the host cell, or can be an expression vector for the expression of any or a combination of the genes of interest. The vector can be, for example, in the form of a plasmid, a viral particle, a phage, etc. In some embodiments, a vector for expression of a polypeptide of interest can also be designed for integration into the host, e.g., by homologous recombination. The vector containing a polynucleotide sequence as described herein, e.g., nucleic acid molecule comprising a modified alphavirus genome or replicon RNA, as well as, optionally, a selectable marker or reporter gene, can be employed to transform an appropriate host cell.

The methods and compositions disclosed herein may be deployed for genetic engineering of any species, including, but not limited to, prokaryotic and eukaryotic species. Suitable host cells to be modified using the compositions and methods according to the present disclosure can include, but not limited to, algal cells, bacterial cells, heterokonts, fungal cells, chytrid cells, microfungi, microalgae, and animal cells. In some embodiments, the animal cells are invertebrate animal cells. In some embodiments, the vertebrate animal cells are mammalians cells. Host cells can be either untransformed cells or cells that have already been transfected with at least one nucleic acid molecule.

The methods and compositions disclosed herein can be used, for example, with subject and/or host cells that are important or interesting for aquaculture, agriculture, animal husbandry, and/or for therapeutic and medicinal applications, including production of polypeptides used in the manufacturing of vaccine, pharmaceutical products, industrial products, chemicals, and the like. In some embodiments, the compositions and methods disclosed herein can be used with host cells from species that are natural hosts of alphaviruses, such as rodents, mice, fish, birds, and larger mammals such as humans, horses, pig, monkey, and apes as well as invertebrates. Particularly preferred species, in some embodiments of the application, are vertebrate animal species and invertebrate animal species. In principle, any animal species can be generally used and can be, for example, human, dog, bird, fish, horse, pig, primate, mouse, cattle, swine, sheep, rabbit, cat, goat, donkey, hamster, or buffalo. Non-limiting examples of suitable bird species include chicken, duck, goose, turkey, ostrich, emu, swan, peafowl, pheasant, partridge, and guinea fowl. In some particular embodiments, the fish species is a salmon species. Primary mammalian cells and continuous/immortalized cells types are also suitable. Non-limiting examples of suitable animal host cells include, but not limited to, pulmonary equine artery endothelial cell, equine dermis cell, baby hamster kidney (BHK) cell, rabbit kidney cell, mouse muscle cell, mouse connective tissue cell, human cervix cell, human epidermoid larynx cell, Chinese hamster ovary cell (CHO), human HEK-293 cell, mouse 3T3 cell, Vero cell, Madin-Darby Canine Kidney Epithelial Cell (MDCK), primary chicken fibroblast cell, a HuT78 cell, A549 lung cell, HeLa cell, PER.C6® cell, WI-38 cell, MRC-5 cell, FRhL-2, and CEM T-cell. In some embodiments, the host cell is baby hamster kidney cell. In some embodiments, the baby hamster kidney cell is a BHK-21 cell.

Techniques for transforming a wide variety of the above-mentioned host cells and species are known in the art and described in the technical and scientific literature. Accordingly, cell cultures including at least one recombinant cell as disclosed herein are also within the scope of this application. Methods and systems suitable for generating and maintaining cell cultures are known in the art.

Methods for Producing Polypeptides

The host cells of the present disclosure, such as a prokaryotic or eukaryotic host cell, can be used to produce (i.e., express) a molecule of interest such as, e.g., a polypeptide, encoded in an open reading frame of a gene of interest (GOI) as disclosed herein. Thus, the present application further provides methods for producing a molecule of interest such as, e.g., a polypeptide, using the host cells of the disclosure, which can be, for example, cells in cell culture or can be cells in a living body.

Accordingly, some embodiments disclosed herein provides methods for producing a polypeptide of interest in a host cell. Such method includes the cultivation of a recombinant host cell, including a nucleic acid molecule according to any one of the preceding aspects and embodiments. In some embodiments, the methods includes culturing the host cell of invention (into which a recombinant expression vector encoding the molecule of interest has been introduced) in a suitable medium such that the molecule of interest is produced. In some embodiments, the methods further include isolating the molecule of interest from the medium or the host cell.

In another aspect, some embodiments relate to methods for producing a polypeptide of interest in a subject, including administering to the subject a nucleic acid molecule according to any one of the preceding aspects and embodiments.

Suitable host cells and/or subjects for use in the methods and compositions disclosed herein include, but are not limited to, prokaryotic and eukaryotic species. Suitable host cells to be modified using the compositions and methods according to the present disclosure can include, but not limited to, algal cells, bacterial cells, heterokonts, fungal cells, chytrid cells, microfungi, microalgae, and animal cells. In some embodiments, the animal cells are invertebrate animal cells. In some embodiments, the vertebrate animal cells are mammalians cells. Host cells can be either untransformed cells or cells that have already been transfected with at least one nucleic acid molecule. Accordingly, biological samples, biomass, and progeny of a recombinant cell according to any one of the preceding aspects and embodiments are also within the scope of the present application. Thus, as discussed in more detail below, polypeptides produced by a method according to this aspect of the application are also within the scope of this application.

In some embodiments, the recombinant cell is an animal cell. Therapeutic protein production in small and large scale is important field of development in pharmaceutical industry, because proteins produced in animal cells are believe to generally have proper processing, post-translational modification and therefore have adequate activity for treatment of the physiological condition. In principle, any animal species can be generally used and can be, for example, human, dog, bird, fish, horse, pig, primate, mouse, cattle, swine, sheep, rabbit, cat, goat, donkey, hamster, or buffalo. Non-limiting examples of suitable bird species include chicken, duck, goose, turkey, ostrich, emu, swan, peafowl, pheasant, partridge, and guinea fowl. In some particular embodiments, the fish species is a salmon species. Primary mammalian cells and continuous/immortalized cells types are also suitable. Non-limiting examples of suitable animal host cells include, but not limited to, pulmonary equine artery endothelial cell, equine dermis cell, baby hamster kidney (BHK) cell, rabbit kidney cell, mouse muscle cell, mouse connective tissue cell, human cervix cell, human epidermoid larynx cell, Chinese hamster ovary cell (CHO), human HEK-293 cell, mouse 3T3 cell, Vero cell, Madin-Darby Canine Kidney Epithelial Cell (MDCK), primary chicken fibroblast cell, a HuT78 cell, A549 lung cell, HeLa cell, PER.C6® cell, WI-38 cell, MRC-5 cell, FRhL-2, and CEM T-cell. In some embodiments, the host cell is baby hamster kidney cell. In some embodiments, the baby hamster kidney cell is a BHK-21 cell.

Recombinant Polypeptides

Some embodiments disclosed herein relate to recombinant polypeptides produced by a method in accordance with one or more embodiments described herein. The recombinant polypeptides of the present application generally can be any recombinant polypeptides and can be, for example, one or more of therapeutic polypeptides, prophylactic polypeptides, diagnostic polypeptides, neutraceutical polypeptides, industrial enzymes, and reporter polypeptides. In some embodiments, the recombinant polypeptides can be one or more of antibodies, antigens, immune modulators, and cytokines. In some embodiments, the polypeptide of interest may have therapeutic or prophylactic activity.

Compositions

Some embodiments disclosed herein relate to a composition comprising any of the recombinant polypeptides described herein. The composition can be, for example, a neutraceutical composition, a prophylactic composition, a pharmaceutical composition comprising a pharmaceutically acceptable carrier, or a mixture thereof. In some embodiments, the compositions of the present application can be used as a vaccine.

Some embodiments disclosed herein relate to a composition including any of the nucleic acid molecules described herein. The composition can be, for example, a neutraceutical composition, a prophylactic composition, a pharmaceutical composition comprising a pharmaceutically acceptable carrier, or a mixture thereof. In some embodiments, the compositions of the present application can be used as a vaccine.

Some embodiments disclosed herein relate to a composition including any of the recombinant cells described herein. The composition can be, for example, a neutraceutical composition, a prophylactic composition, a pharmaceutical composition comprising a pharmaceutically acceptable carrier, or a mixture thereof. In some embodiments, the compositions of the present application can be used as a vaccine.

As used herein, the term "pharmaceutically-acceptable carrier" means a carrier that is useful in preparing a pharmaceutical composition or formulation that is generally safe, non-toxic, and neither biologically nor otherwise undesirable, and includes a carrier that is acceptable for veterinary use as well as human pharmaceutical use. In some embodiments, a pharmaceutically acceptable carrier as simple as water, but it can also include, for example, a solution of physiological salt concentration. In some embodiments, a pharmaceutically acceptable carrier can be, or may include, stabilizers, diluents and buffers. Suitable stabilizers are for example SPGA, carbohydrates (such as dried milk, serum albumin or casein) or degradation products thereof. Suitable buffers are for example alkali metal phosphates. Diluents include water, aqueous buffers (such as buffered saline), alcohols and polyols (such as glycerol). For administration to animals or humans, the composition according to the present application can be given inter alia intranasally, by spraying, intradermally, subcutaneously, orally, by aerosol or intramuscularly.

All publications and patent applications mentioned in this disclosure are herein incorporated by reference to the same extent as if each individual publication or patent application was specifically and individually indicated to be incorporated by reference.

No admission is made that any reference cited herein constitutes prior art. The discussion of the references states what their authors assert, and the inventors reserve the right to challenge the accuracy and pertinence of the cited documents. It will be clearly understood that, although a number of information sources, including scientific journal articles, patent documents, and textbooks, are referred to herein; this reference does not constitute an admission that any of these documents forms part of the common general knowledge in the art.

The discussion of the general methods given herein is intended for illustrative purposes only. Other alternative methods and alternatives will be apparent to those of skill in the art upon review of this disclosure, and are to be included within the spirit and purview of this application.

EXAMPLES

Additional alternatives are disclosed in further detail in the following examples, which are not in any way intended to limit the scope of the claims.

Example 1

General Experimental Procedures

In Vitro Transcription

In vitro transcription (IVT) reactions were performed using 1 µg of DNA template prepared as described above, in a 20 µl reaction over a one hour incubation at 37° C. (NEB cat. no. E2065S). 1 Unit of DNase I, provided by the supplier was then added directly to the IVT reaction, and incubated at 37° C. for an additional 15 mins. Reactions were then placed on ice, and purified using the manufactures suggested method (Qiagen Cat. no. 74104). Purified RNA was then quantified using a NanoDrop 2000c UV-Vis Spectrophotometer. RNA was visualized by electrophoresis through 0.8% Agarose gels (Life Technologies Cat. no. G5018-08) and compared with Millennium RNA Marker (Ambion Cat. No. AM7150), prior to proceeding with electroporation.

Plasmid DNA templates were purified (Qiagen Cat. no. 12163) from 300 mL of saturated *E. coli* TransforMax Epi300 (Epicentre Cat. no. EC300105) cultures grown in LB broth media (Teknova Cat. no. L8000 06) supplemented with 50 ng/ml carbamicilin (Teknova Cat. no. NC9730116). Plasmid DNA was linearized by Not-I digestion (New England Biolabs NEB cat. no. R3189S) for one hour at 37° C. Linearized template DNA was then re-purified (Zymo Cat. no. D4003), and analyzed by 0.8% agarose gel (Life Technologies Cat. no. G5018-08) against a commercial 2-log DNA ladder (New England Biolabs, NEB Cat. no. N3200S). The presence of a single band was confirmed in each sample, corresponding to the expected fragment size of the linear DNA template, prior to proceeding with in vitro transcription.

Transfection and Analysis

In a typical cell transfection experiment, replicon RNA was introduced into BHK-21 cells by electroporation using the SF Cell Line Nucleofector™ kit for the 4D-Nucleofector™ System (Lonza). BHK-21 cells were harvested using 0.25% trypsin and washed once with cold PBS. Cells were resuspended in SF Buffer at a cell density of $1\times10^6$ cells per 20 µL electroporation reaction. Three micrograms of RNA was electroporated into cells in triplicate in a 16-well cuvette strip and incubated at room temperature for 10 minutes. Electroporated cells were recovered into plates containing Dulbecco's Modified Eagle Medium containing 10% fetal bovine serum, followed by incubation for 16-18 h at standard cell culture conditions.

Intracellular analyses of replicon transfection efficiency and protein production were performed by flow cytometry. Transfected BHK-21 cells were fixed and permeabilized using fix/perm concentrate and permeabilization buffer (eBioscience). Cells were incubated with antibodies for double-stranded RNA production (J2 anti-dsRNA IgG2A monoclonal antibody, English & Scientific Company) conjugated with R-Phycoerythrin (Innova Biosciences). Antigen production was assessed by additional incubation with antigen-specific antibodies conjugated with PE-Cy5 (Innova Biosciences) (e.g. antibodies for green Renilla, red Firefly, HA, or RSV-F0 (Abcam)). Cells were then washed once and analyzed using a FACSAria™ Fusion Cell Sorter (BD Biosciences) or FACSAria™ II Cell Sorter (BD Biosciences). Transfected BHK-21 cells stained with single colors for compensation controls were run prior to sample collection. Data was collected using FACSDiva (BD Biosciences) and further analyzed using FlowJo software. Initial gating was performed to exclude dead cells and debris using forward and side scatter plots. Further gating was conducted to identify cell populations that were positive for both dsRNA (R-PE-positive) and protein expression (PE-Cy5-positive or FITC-positive for GFP expression). Frequencies and mean fluorescence intensities were collected and utilized for construct comparison and optimization.

Example 2

5'-UTR Sequence Modifications

This Example describes the results of experiments where 5'-UTR sequences were modified to enhance expression of the genes of interest encoded in a VEEV replicon RNA vector. Site directed mutagenesis (SDM) was carried out on a plasmid containing a cDNA copy of a VEEV replicon vector. SDM primers were designed to change the thymine (T) residue at position 2 of the 5' UTR to a G residue In these experiments, VEEV replicons each expressing the rFF luciferase gene, the A Vietnam 1203 influenza hemagglutinin gene (HA) or the green fluorescent protein (GFP) gene, were used as templates to carry out site-directed mutagenesis. The nucleotide T at position 2 in the 5' UTR of the wild-type VEEV (strain TC-83) sequence was changed to G. Primers "VEE 5' T→G nt 2 F" and "VEE 5' T→G nt 2 R" were used to introduce the nucleotide 2 change via a site-directed mutagenesis kit from Agilent. The primers were designed through the Agilent's website. Positive clones were identified and a representative clones expressing the rFF, HA and GFP were sequence-confirmed to be completely correct.

SDM primers to make Alpha-R-T2G replicons are as follows.
Forward primer: VEE 5' T→G nt 2 F (SEQ ID NO: 23): cgactcactatagaGaggcggcgcatgag.
Reverse primer: VEE 5' T→G nt 2 R (SEQ ID NO: 24): ctcatgcgccgcctCtctatagtgagtcg.

After sequence confirmation of T2→G change in the VEEV replicon cDNA, RNA was generated by in vitro transcription using T7 RNA polymerase on linearized plasmid DNA. The in vitro transcribed RNA was purified and used to electroporated BHK-21 cells. Both replication and GOI expression were monitored by FACS using anti-dsRNA specific and GOI-specific antibodies, respectively. Replication efficiency and GOI expression from U2→G VEEV replicons were compared directly to wild type VEEV replicons expressing the same GOI. The sequence of Alpha-R-rFF-T2G replicon comprising a red Firefly reporter gene is provided as SEQ ID NO: 19 in the Sequence Listing with the T7 promoter and a polyA tail with 40 A residues. The mutated nucleotide at position 2 following the T7 promoter sequence is also indicated.

Example 3

U2→G Substitution in the 5'UTR does not Affect Biologic Activity of Modified VEEV-HA Replicon This Example describes the results of experiments assessing impact of an U2→G substitution in the 5' UTR of a modified alphavirus replicon on expression of an A Vietnam 1203 influenza hemagglutinin gene (HA) reporter gene.

In order to demonstrate that an alphavirus replicon containing a U2→G change in the 5' UTR can indeed express protein, replicon RNA was transcribed in vitro from a vector carrying a U2→G change in the 5' UTR (U2→G VEEV-HA). As a positive control for expression, RNA was transcribed in vitro from a vector carrying a wild-type 5' UTR (WT VEEV-HA). Baby hamster kidney (BHK-21) cells were electroporated with 3 μg of either U2→G VEEV-HA RNA of wild-type VEEV-HA RNA. An example of flow cytometry analysis for this comparison is shown in FIG. 1. The cells were analyzed by FACS with an HA-specific antibody to demonstrate both the presence of expressed HA protein and the relative amount of HA expressed on a per cell basis (mean fluorescence intensity—MFI). There is no loss of biologic activity from a replicon RNA carrying the U2→G 5' UTR change relative to the activity detected from a replicon with a wild-type 5' UTR.

The experimental data presented in this Example indicate that not only can the U2→G VEEV-HA replicon express HA protein but the expression level is equivalent to that of the wild-type VEEV-HA replicon. This result is unexpected considering that the VEEV/SINV infectious clone carrying the same U2→G 5' UTR change had nearly a three log loss in biological activity; here we show no reduction at all in biologic activity for a replicon carrying the U2→G 5' UTR change.

Example 4

U2→G Substitution in the 5'UTR Enhances Expression of GFP Reporter by 3 Folds

This Example describes the results of experiments assessing impact of an U2→G substitution in the 5' UTR of a modified alphavirus replicon on expression of a green fluorescence protein (GFP) reporter gene.

In order to demonstrate that expression from an alphavirus replicon containing a U2→G change in the 5' UTR is not restricted to any particular GOI, replicon vectors expressing the GFP gene were compared in a similar manner. Replicon RNA was transcribed in vitro from a vector carrying a U2→G change in the 5' UTR (U2→G VEEV-GFP). As a positive control for expression, RNA was transcribed in vitro from a vector carrying a wild-type 5' UTR (WT VEEV-GFP). BHK cells were electroporated with 3 μg of either U2→G VEEV-GFP RNA or wild-type VEEV-GFP RNA. An example of flow cytometry analysis for this comparison is shown in FIG. 2. The cells were analyzed for GFP expression by FACS to demonstrate both the presence of expressed GFP protein and the relative amount of GFP expressed on a per cell basis (mean fluorescence intensity—MFI). Not only is there is no loss of biologic activity from a replicon RNA carrying the U2→G 5' UTR but the U2→G 5' UTR change actually enhanced expression by 3 fold relative to the expression detected from a replicon with a wild-type 5' UTR.

Once again the experimental data presented in this Example indicate that a replicon vector carrying the U2→G 5' UTR change can express protein (this time GFP). Perhaps even more unexpected than simple protein expression is that the U2→G VEEV-GFP replicon expressed three times more GFP than that of the wild-type VEEV-GFP replicon. Once more, the expected loss in biologic activity anticipated due to the U2→G change in the 5' UTR was not realized and this result demonstrated that the U2→G change in the 5' UTR can actually significantly enhance GOI replicon expression.

Example 5

U2→G Substitution in the 5'UTR Enhances Expression of rFF Reporter by 2 Folds

This Example describes the results of experiments assessing impact of an U2→G substitution in the 5' UTR of a modified alphavirus replicon on expression of a red Firefly (rFF) reporter gene.

Figure 3:
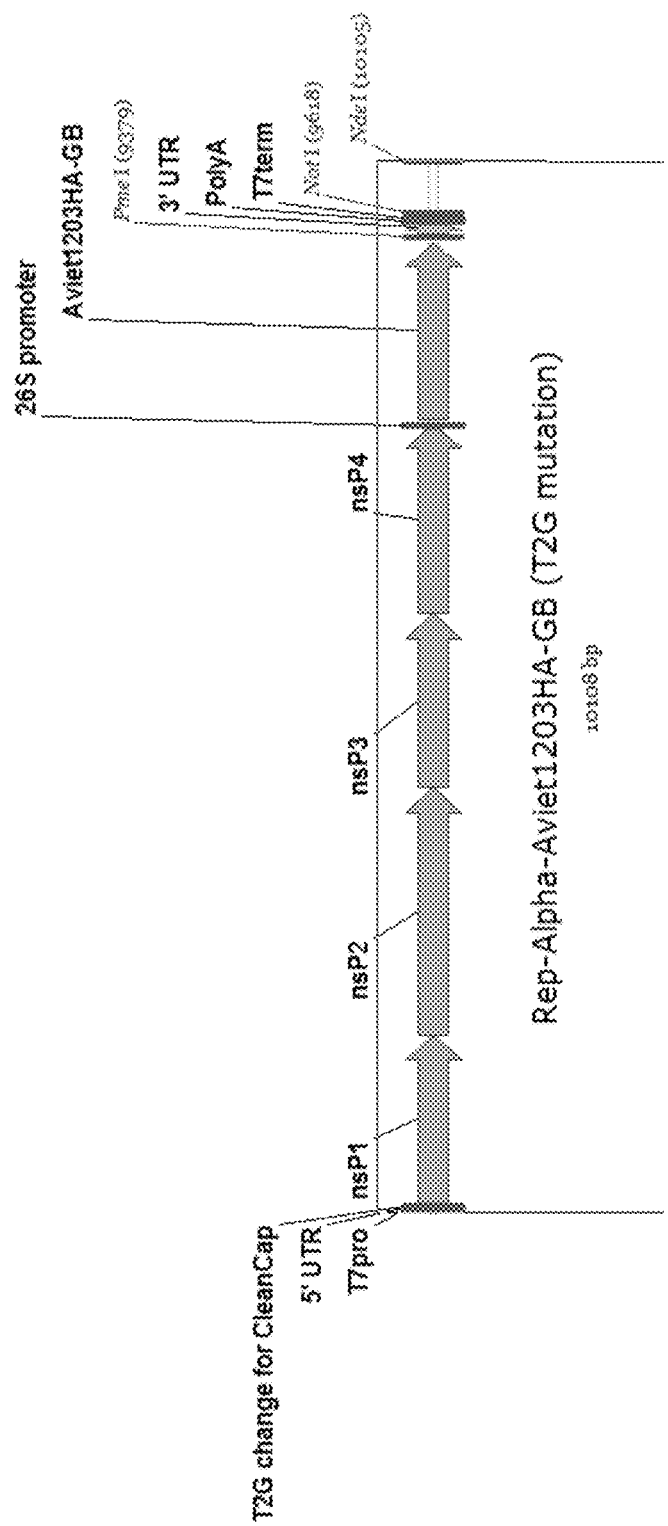
FIGS. 3 and 4 graphically depicts the structures of two non-limiting exemplary monovalent VEEV replicon designs, in which the gene of interest (GOI) operably incorporated into the vector was an A Vietnam 1203 HA gene (FIG. 3) and an enhanced green fluorescence protein (eGFP) reporter gene (FIG. 4), respectively.
Figure 4:
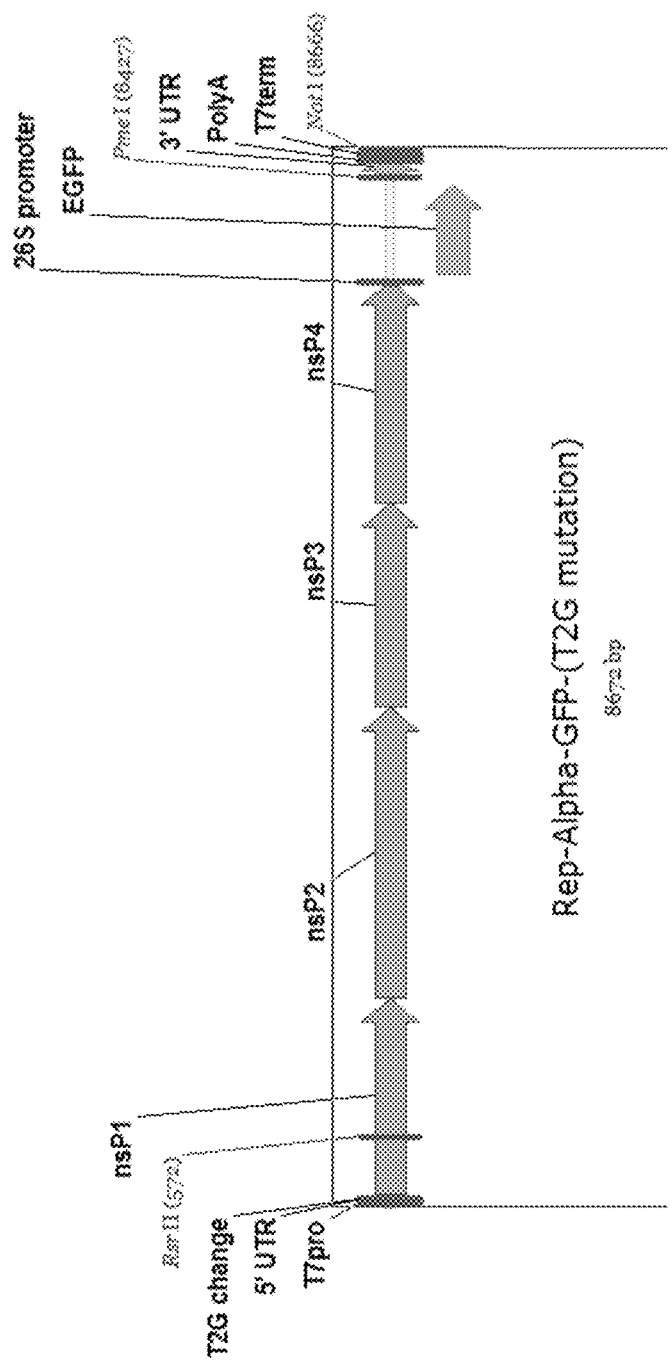
Figure 5:
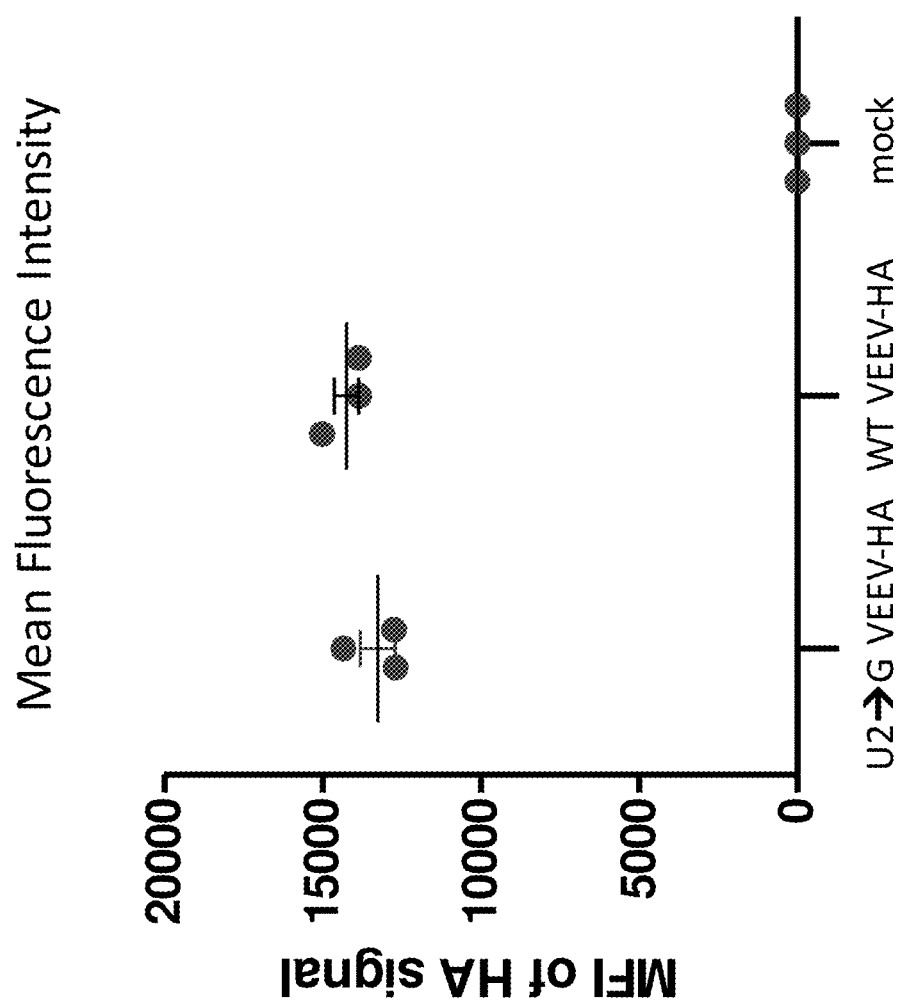
FIG. 5 graphically summarizes the results of exemplary experiments illustrating that a U2→G modification at position 2 of the 5'UTR in a modified VEEV-HA replicon does not affect biological activity of the modified replicon. Flow cytometry analysis (FACS) was performed on cells electroporated with a modified U2→G VEEV-HA replicon expressing an influenza hemagglutinin-HA gene (also see FIG. 3 for structural organization of the replicon). A wild-type VEEV-HA replicon, i.e. containing a U residue at position 2, was used as control.
Figure 6:
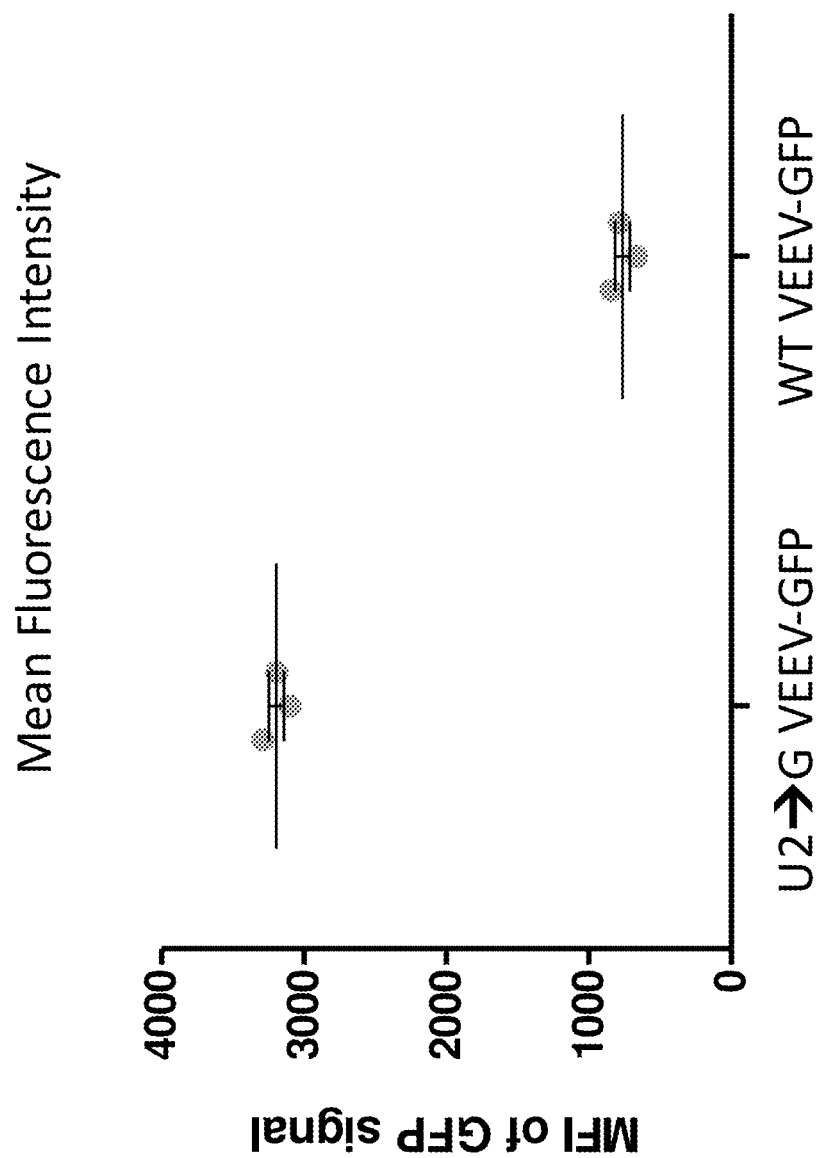
FIG. 6 graphically summarizes the results of an exemplary flow cytometry analysis performed to demonstrate that expression from an alphavirus replicon carrying a U2→G modification in the 5'UTR is not restricted to any particular gene of interest (GOI). In this experiment, the modified alphavirus replicon was engineered to express a green fluorescent protein (GFP) reporter gene (also see FIG. 4 for structural organization of the replicon). The U2→G modification in the 5'UTR of the modified VEEV-GFP replicon was shown to enhance expression of GFP gene by 3-fold relative to the expression detected from a wild-type control replicon.
Figure 7:
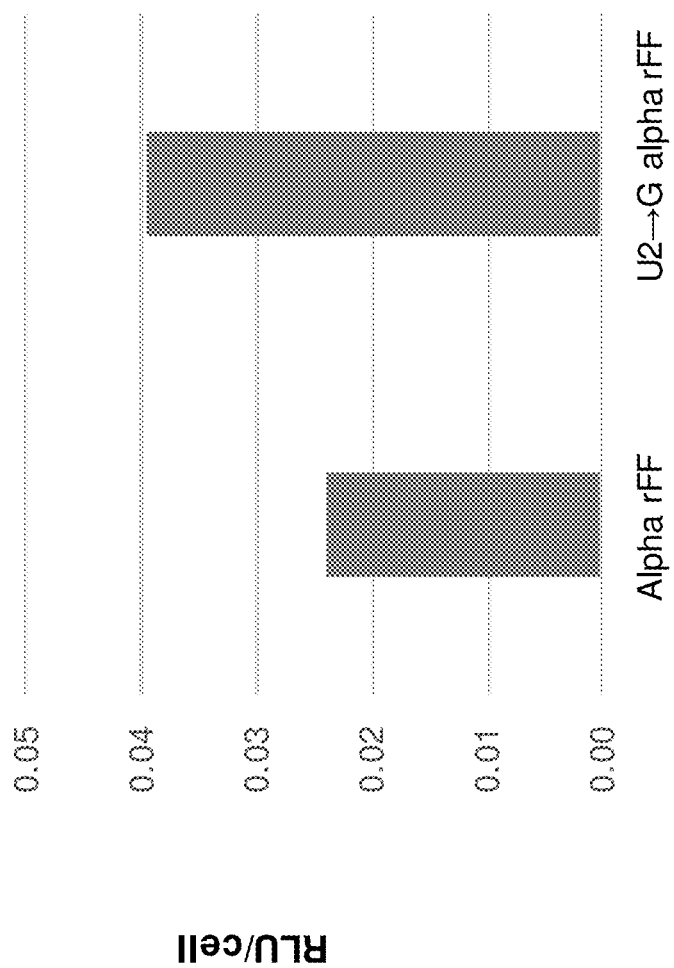
FIG. 7 graphically summarizes the results of yet another exemplary flow cytometry analysis assessing expression of a red Firefly reporter gene from a modified VEEV replicon. In this experiment, the U2→G modification in the 5'UTR of the modified VEEV-rFF replicon was shown to enhance expression of the red Firefly gene by 2-fold relative to the expression detected from a wild-type control replicon.
Figure 8:
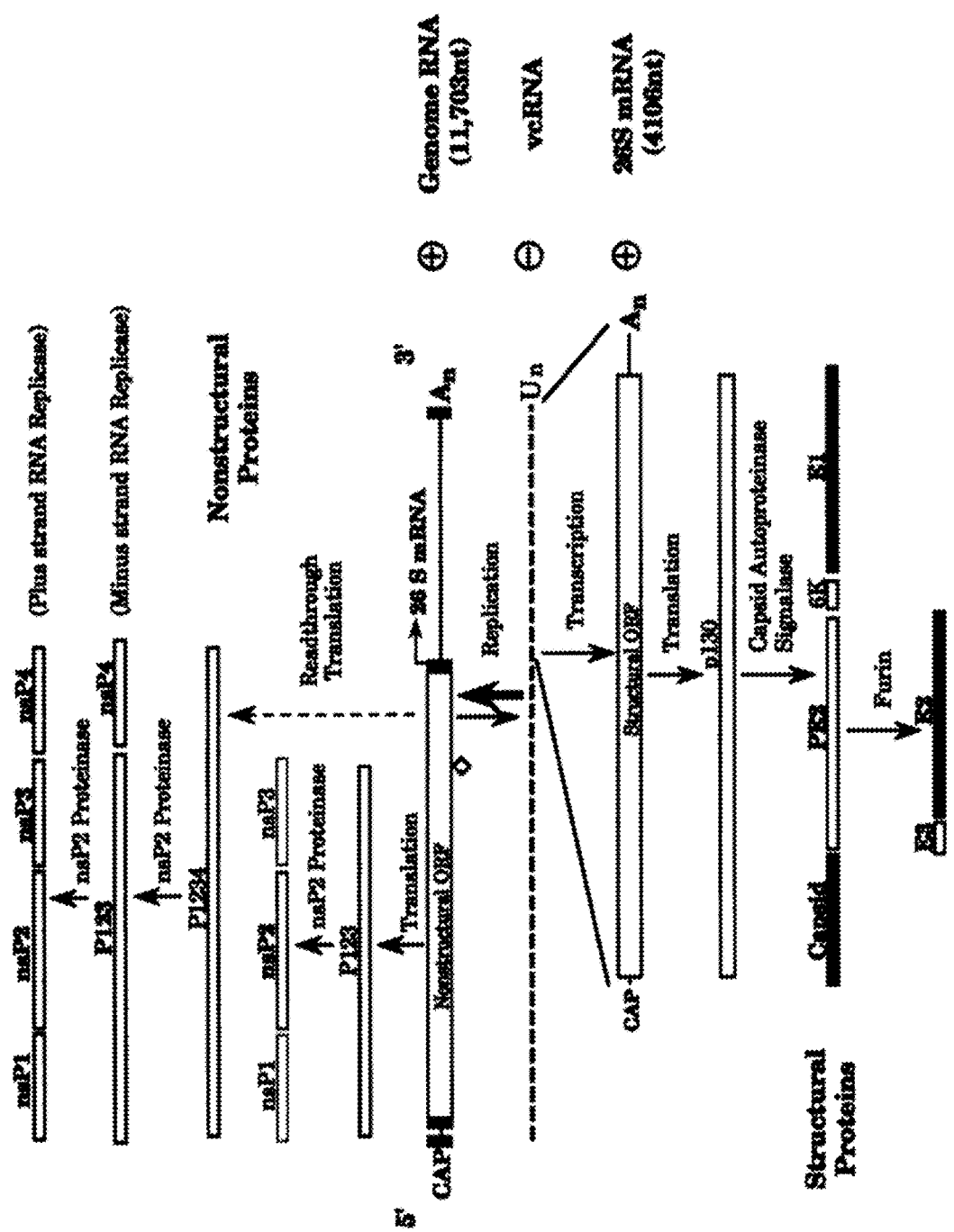
FIG. 8 schematically depicts a non-limiting exemplary alphavirus genomic structure and genome expression (adapted from Strauss et al., Microbiological Reviews, pp. 491-562, September 1994). Genome organization of a SIN virus is shown. The names of the nonstructural genes and structural protein genes are given. Referenced to the nomenclature of the genes and proteins can be found in Strauss et al., supra, 1994. The 49S genomic RNA is illustrated schematically in the center, with its translated ORF shown as an open box. Small black boxes are conserved sequence elements; the open diamond denotes the leaky opal termination codon. The nonstructural polyproteins and their processed products are shown above. Termination at the opal codon produces P123, whose major function in replication is believed to be as a proteinase that acts in trans to process the polyproteins in active RNA replicases; this proteinase domain is found in the nsP2 region. Readthrough of the opal stop codon produces P1234, which can form an active replicase. The 26S subgenomic mRNA is expanded below to show the structural ORF and its translation products. Polypeptides present in the virion are shaded. vcRNA is the minus-strand complement of the genomic RNA.

In these experiments, another example of expression from an alphavirus replicon containing a U2→G change in the 5' UTR, replicon vectors expressing the rFF gene were compared in a similar manner. Replicon RNA was transcribed in vitro from a vector carrying a U2→G change in the 5' UTR (U2→G VEEV-rFF). As a positive control for expression, RNA was transcribed in vitro from a vector carrying a wild-type 5' UTR (WT VEEV-rFF). BHK cells were electroporated with 3 µg of either U2→G VEEV-rFF RNA or wild-type VEEV-rFF RNA. An example of luciferase protein expression is shown in FIG. 3. In this experiment, the ability of an alphavirus replicon modified to carry a U2→G change in the 5' UTR (U2→G alpha rFF) was compared to an alphavirus replicon that had a wild-type 5' UTR (Alpha rFF). BHK cells were electroporated with an equivalent amount of in vitro transcribe RNA from either replicon and then the cells were analyzed for rFF luciferase expression. The amount of luciferase (expressed as relative light units (RLU)) expressed on a per cell basis is presented. Not only is there is no loss of biologic activity from a replicon RNA carrying the U2→G 5' UTR but the U2→G 5' UTR change actually enhanced expression by approximately 2 fold relative to the expression detected from a replicon with a wild-type 5' UTR.

Once again the experimental data presented in this Example indicate that a replicon vector carrying the U2→G 5' UTR change can express protein (this time rFF). Perhaps even more unexpected than simple protein expression is that the U2→G VEEV-rFF replicon expressed~two times more rFF than that of the wild-type VEEV-rFF replicon. Once more, the expected loss in biologic activity anticipated due to the U2→G change in the 5' UTR was not realized and this result demonstrated that the U2→G change in the 5' UTR can actually significantly enhance GOI replicon expression.

Example 6

Multivalent VEEV Replicon Designs

This Example describes experiments performed to construct and evaluate multivalent VEEV replicons, which are subsequently deployed for expression of at least two different polypeptides in recombinant cells. In some experiments, the multivalent VEEV replicon includes in 5' to 3' order (i) a 5' sequence required for nonstructural protein-mediated amplification, (ii) a nucleotide sequence encoding VEEV nonstructural proteins nsP1, nsP2, nsP3, and nsP4, (iii) at least two promoters each of which is operably linked to a heterologous nucleic acid sequence, wherein the heterologous nucleic acid sequence replaces one or all of the VEEV structural protein genes, (iv) a 3' sequence required for nonstructural protein-mediated amplification, and (v) a polyadenylate tract.

While particular alternatives of the present disclosure have been disclosed, it is to be understood that various modifications and combinations are possible and are contemplated within the true spirit and scope of the appended claims. There is no intention, therefore, of limitations to the exact abstract and disclosure herein presented.

What is claimed is:

1. A nucleic acid molecule comprising a modified alphavirus replicon RNA, wherein the modified replicon RNA comprises a modified 5'-UTR of an alphavirus and sequences coding for biologically active alphavirus nonstructural proteins, and is devoid of at least a portion of a nucleic acid sequence encoding viral structural proteins, wherein the modified 5'UTR comprises a U to G nucleotide substitution at position 2.

2. The nucleic acid molecule of claim 1, wherein the modified alphavirus replicon further comprises a subgenomic promoter RNA, 3' viral sequences required in cis for replication, and a polyadenylate tract.

3. The nucleic acid molecule of claim 1, wherein the modified alphavirus replicon RNA is devoid of a substantial portion of the nucleic acid sequence encoding viral structural proteins.

4. The nucleic acid molecule of claim 1, further comprising one or more expression cassettes, wherein each of the one or more expression cassettes comprises a promoter operably linked to a heterologous nucleic acid sequence.

5. A composition comprising the nucleic acid molecule of claim 4, and a pharmaceutically acceptable carrier.

6. The nucleic acid molecule of claim 1, wherein the modified alphavirus replicon RNA is modified from an alphavirus belonging to the *Alphavirus* genus of the Togaviridae family.

7. The nucleic acid molecule of claim 6, wherein the alphavirus belongs to the VEEV/EEEV (Venezuelan equine encephalitis virus/Eastern equine encephalitis virus) group, or the SF (Semliki Forest) group, or the SIN (Sindbis) group.

8. The nucleic acid molecule of claim 7, wherein the alphavirus is VEEV.

9. The nucleic acid molecule of claim 1, wherein the modified replicon RNA is operably linked to a heterologous regulatory element.

10. A recombinant cell comprising the nucleic acid molecule of claim 1, wherein the recombinant cell is a prokaryotic or a eukaryotic cell.

11. A composition comprising the recombinant cell of claim 10, and a pharmaceutically acceptable carrier.

12. A composition comprising the nucleic acid molecule of claim 1, and a pharmaceutically acceptable carrier.

13. A nucleic acid molecule encoding the nucleic acid molecule of claim 1.

14. A recombinant cell comprising the nucleic acid molecule of claim 13, wherein the recombinant cell is a prokaryotic or a eukaryotic cell.

15. A method for producing a polypeptide of interest, comprising culturing a host cell comprising a nucleic acid molecule which comprises a modified alphavirus replicon RNA encoding the polypeptide of interest, wherein the modified alphavirus replicon RNA comprises a modified 5-'UTR of an alphavirus and sequences coding for biologically active alphavirus nonstructural proteins, and is devoid of at least a portion of a nucleic acid sequence encoding viral structural proteins, wherein the modified 5'-UTR comprises a U to G nucleotide substitution at position 2.

16. The method of claim 15, wherein the modified alphavirus replicon RNA is modified from an alphavirus belonging to the *Alphavirus* genus of the Togaviridae family.

17. A method for producing a polypeptide of interest in a subject, comprising administering to the subject a nucleic acid molecule comprising a modified alphavirus replicon RNA encoding the polypeptide of interest, wherein the modified alphavirus replicon RNA comprises a modified 5-'UTR of an alphavirus and sequences coding for biologically active alphavirus nonstructural proteins, and is devoid of at least a portion of a nucleic acid sequence encoding viral structural proteins, wherein the modified 5'-UTR comprises a U to G nucleotide substitution at position 2.

18. The method of claim 17, wherein the subject is a human, horse, pig, primate, mouse, cattle, swine, sheep, rabbit, cat, dog, bird, fish, goat, donkey, hamster, or buffalo.

* * * * *